(12) United States Patent
Adams et al.

(10) Patent No.: US 10,016,525 B2
(45) Date of Patent: Jul. 10, 2018

(54) ANTIMICROBIAL COMPOSITIONS FOR USE IN WOUND CARE PRODUCTS

(71) Applicant: Agienic, Inc., Tucson, AZ (US)

(72) Inventors: Lori L. Adams, Tucson, AZ (US); Nicholas R. Krasnow, Tucson, AZ (US); Anoop Agrawai, Tucson, AZ (US); Donald R. Uhlmann, Tucson, AZ (US)

(73) Assignee: Agienic, Inc., Tucson, AZ (US)

( * ) Notice: Subject to any disclaimer, the term of this patent is extended or adjusted under 35 U.S.C. 154(b) by 0 days.

(21) Appl. No.: 14/720,388

(22) Filed: May 22, 2015

(65) Prior Publication Data

US 2016/0220728 A1 Aug. 4, 2016

Related U.S. Application Data

(63) Continuation-in-part of application No. 14/089,146, filed on Nov. 25, 2013, now Pat. No. 9,155,310, and a continuation-in-part of application No. 13/685,379, filed on Nov. 26, 2012, now abandoned, which is a continuation-in-part of application No. 13/480,367, filed on May 24, 2012, now abandoned.

(60) Provisional application No. 61/800,122, filed on Mar. 15, 2013, provisional application No. 61/820,561, filed on May 7, 2013, provisional application No. 61/881,318, filed on Sep. 23, 2013, provisional application No. 61/582,322, filed on Dec. 31, 2011, provisional application No. 61/519,523, filed on May 24, 2011.

(51) Int. Cl.

| | | |
|---|---|---|
| A61K 33/34 | (2006.01) | |
| A61K 33/18 | (2006.01) | |
| A61Q 17/00 | (2006.01) | |
| A61K 8/20 | (2006.01) | |
| A61L 15/18 | (2006.01) | |
| A61L 26/00 | (2006.01) | |
| C08K 3/16 | (2006.01) | |
| A61L 15/46 | (2006.01) | |
| A61K 8/25 | (2006.01) | |
| A61Q 3/02 | (2006.01) | |
| A61K 8/02 | (2006.01) | |
| C09D 5/14 | (2006.01) | |
| C09K 8/524 | (2006.01) | |
| C09K 8/54 | (2006.01) | |
| A01N 59/20 | (2006.01) | |
| A61K 8/73 | (2006.01) | |

(52) U.S. Cl.
CPC .............. *A61L 15/46* (2013.01); *A01N 59/20* (2013.01); *A61K 8/0279* (2013.01); *A61K 8/0283* (2013.01); *A61K 8/20* (2013.01); *A61K 8/25* (2013.01); *A61K 8/736* (2013.01); *A61K 33/18* (2013.01); *A61K 33/34* (2013.01); *A61L 15/18* (2013.01); *A61L 26/0066* (2013.01); *A61Q 3/02* (2013.01); *A61Q 17/005* (2013.01); *C09D 5/14* (2013.01); *C09K 8/524* (2013.01); *C09K 8/54* (2013.01); *A61K 2800/412* (2013.01); *A61L 2300/102* (2013.01); *A61L 2300/106* (2013.01); *A61L 2300/404* (2013.01); *A61L 2400/12* (2013.01); *C08K 3/16* (2013.01)

(58) Field of Classification Search
None
See application file for complete search history.

(56) References Cited

U.S. PATENT DOCUMENTS

| | | | | |
|---|---|---|---|---|
| 5,261,421 A | * | 11/1993 | Milner | .................. A61B 42/10 128/898 |
| 8,563,020 B2 | | 10/2013 | Uhlmann et al. | |
| 2006/0141015 A1 | * | 6/2006 | Tessier | .................. A01N 59/16 424/443 |
| 2006/0269485 A1 | | 11/2006 | Friedman et al. | |
| 2007/0254044 A1 | | 11/2007 | Karadikar et al. | |
| 2008/0033329 A1 | * | 2/2008 | Downs | ................ A61F 13/0273 602/41 |
| 2008/0199502 A1 | * | 8/2008 | Tessier | .................. A01N 25/02 424/405 |
| 2009/0202456 A1 | | 8/2009 | Prencipe et al. | |
| 2011/0252580 A1 | * | 10/2011 | Miller | .................... D06M 11/42 8/190 |
| 2012/0301531 A1 | * | 11/2012 | Uhlmann | ................ A01N 59/16 424/405 |

FOREIGN PATENT DOCUMENTS

| | | | | |
|---|---|---|---|---|
| CA | 2776363 A1 | * | 4/2011 | ............. A61L 31/16 |
| WO | WO 0247737 A1 | * | 6/2002 | ....... A61F 13/00063 |

OTHER PUBLICATIONS

D. Church et al., "Burn Wound Infections," Clinical Microbiology Reviews, vol. 19, No. 2, Apr. 2006, p. 403-434.*
R. Edwards et al., "Bacteria and wound healing," Currrent Opinion in Infectious Diseases 2004, 17:91-96.*
A. Pramanik et al., "A novel study of antibacterial activity of copper iodide nanoparticle mediated by DNA and membrane damage," Colloids and Surfaces B: Biointerfaces 96 (2012) 50-55.*
K. Paudel et al., "Challenges and opportunities in dermal/transdermal delivery," Ther Deliv. Jul. 2010; 1(1): 109-131.*
Ibrahim, S.A., et al, Food Chemistry, vol. 109 (2008) p. 137-143.
Thomas, S., et.al., Wound care, vol. 12(8) (2003) p. 305-308.
Davidson J.R., Veterinary Clinics of N. America, Small Animal Practice, vol. 45 (2015) p. 537-564.

(Continued)

*Primary Examiner* — Tracy Vivlemore
*Assistant Examiner* — Monica A Shin
(74) *Attorney, Agent, or Firm* — Rothwell, Figg, Ernst & Manbeck, P.C.

(57) ABSTRACT

Compositions having antimicrobial activity contain surface functionalized particles comprising an inorganic copper salt which has low water solubility. These types of inorganic salts may also be introduced in porous particles to yield antimicrobial compositions. The compositions may optionally comprise additional antimicrobial agents, salts with high water solubility, organic acids, salts of organic acids and their esters. The above compositions can be incorporated in a variety of wound care products to provide antimicrobial properties.

11 Claims, 11 Drawing Sheets

(56) References Cited

OTHER PUBLICATIONS

Longaker, M., et.al., Annals of Surgery, 210(5), (1989) p. 667-672.
Burns J.L., et.al., Clinical Plastics Surgery, vol. 30 (2003) p. 47-56.
Gethin, G., Wounds UK, vol. 3(3) (2007) p. 52-56.
Lipp C. Et al, J. Of Wound Care, vol. 19(6) (2010) p. 220-226.
Zhong, T., et .al., Wood and Fiber Science, vol. 25(2), (2013) p. 305-308.
Corinne K Cusumano, et al., Sci Transl Med 3, 109ra115 (2011) (DOI: 10.1126/scitranslmed.3003021 "Treatment and Prevention of Urinary Tract Infection with Orally Active FimH Inhibitors".
Thurston-Enriquez, J.A. et.al., "Chlorine Inactivation of Adenovirus Type 40 and Feline Calicivirus", Appl. Environ. Microbiol. vol. 69 No. 7, (2003) p. 3979-3985.
Black et al. "Determination of Ct values for chlorine resistant enteroviruses," J. Environ. Sci. Health A Tox. Hazard Subst. Environ. Eng. 44: (2009) p. 336-339.
Bidawid et al. "A feline kidney cell line-based plaque assay for feline calcivirus, a surrogate for Norwalk virus", J. Virol. Methods vol. 107, (2003) p. 163-167.

\* cited by examiner

**Germination of *Bacillus cereus* spores under defined growth conditions**

- ■ 24 Hour Incubation at 25°C
- □ 24 Hour Incubation at 37°C

Y-axis: OD600 (0 to 2.5)
X-axis: Intial, Control, Cul-PVP

FIGURE 3

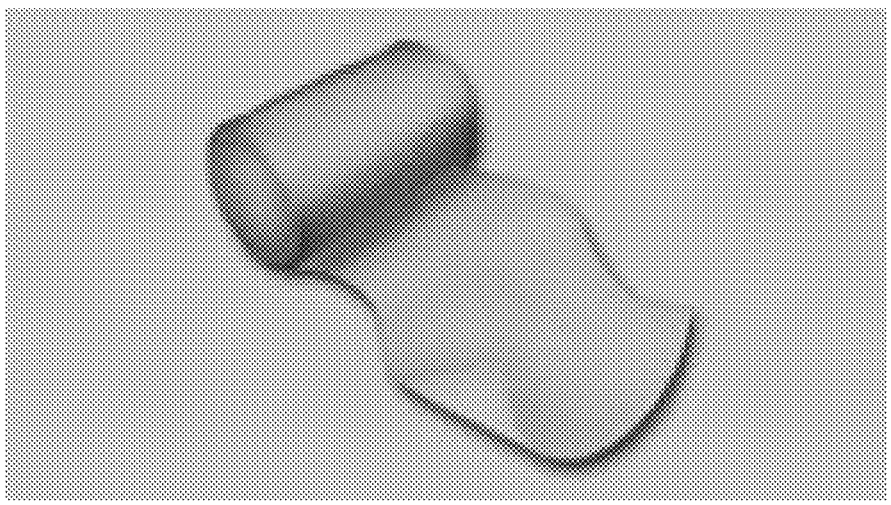
Figure 7: Antimicrobial wound care bandage
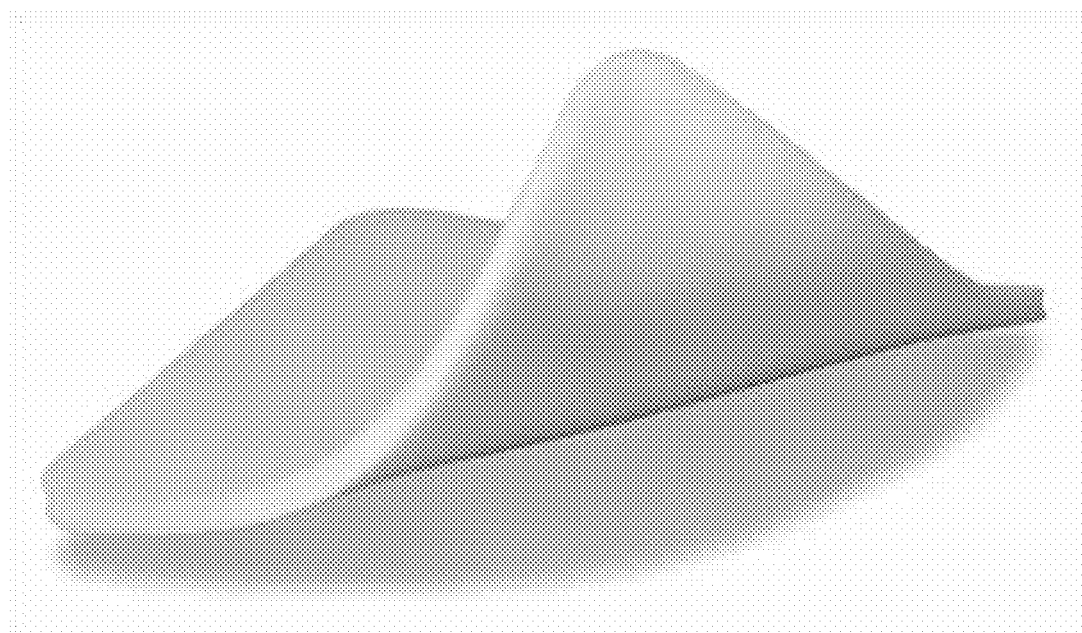
Figure 8: Antimicrobial wound care foam product

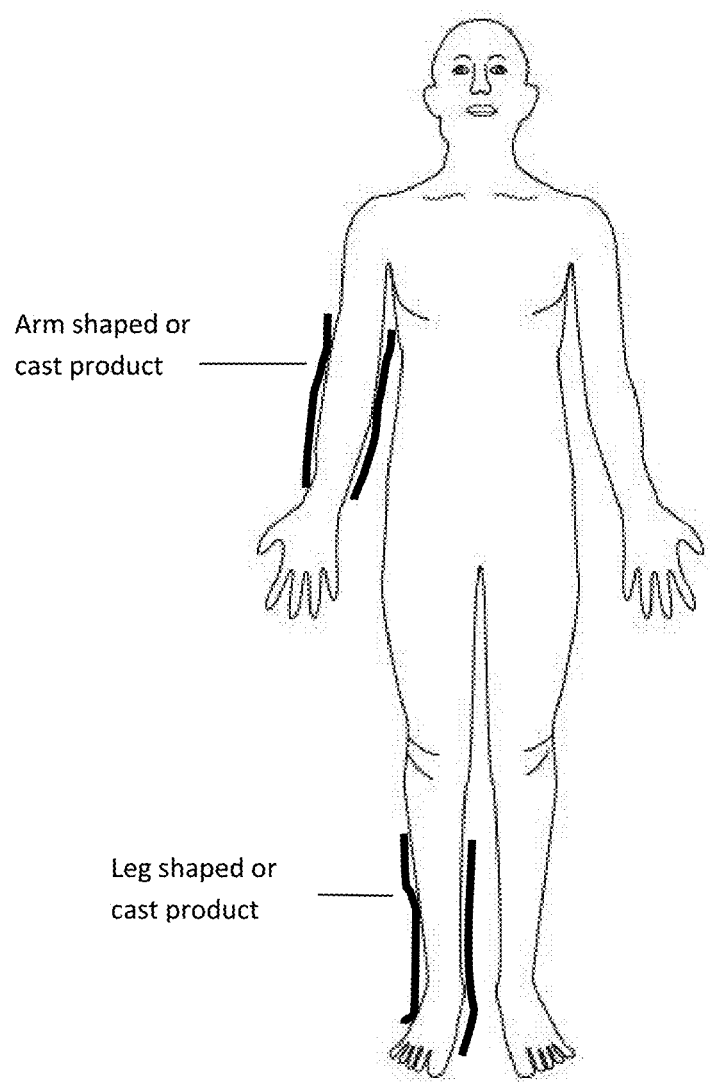
Figure 9: Various shaped or cast antimicrobial products for wounds

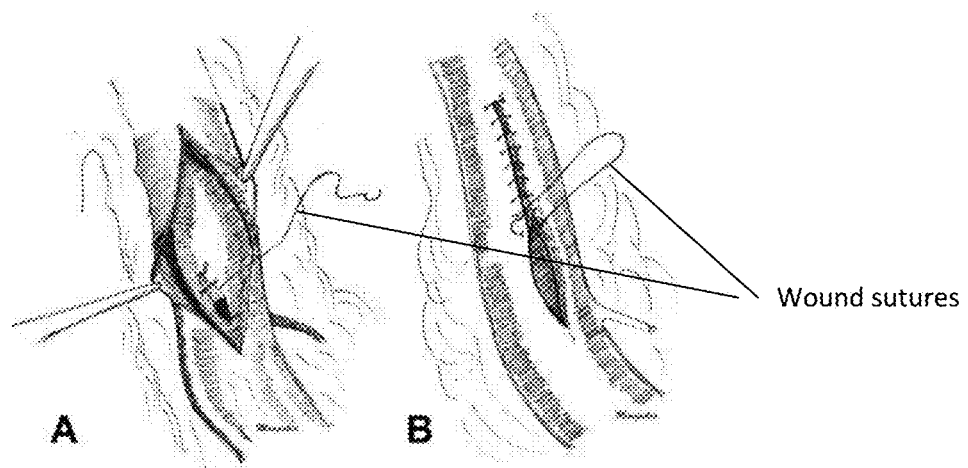
Figure 10: Antimicrobial wound sutures
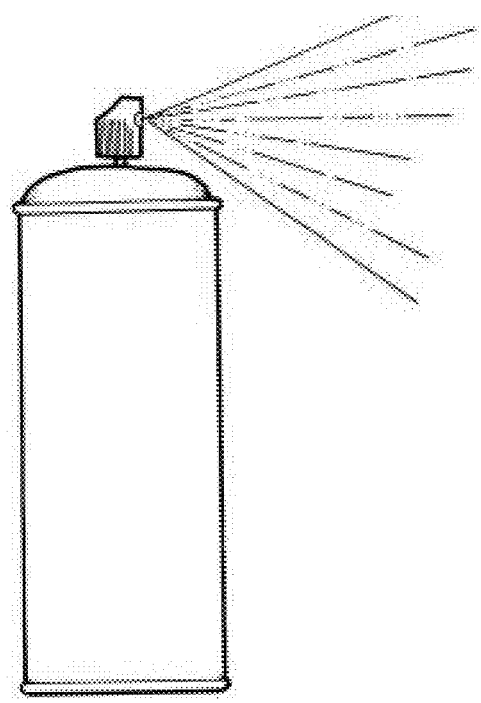
Figure 11: Spray can with antimicrobial wound lotion or an antimicrobial sprayable bandage

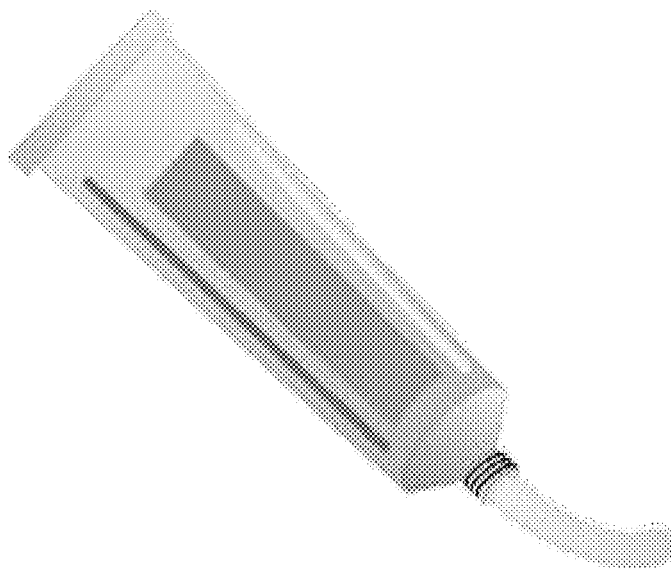
Figure 12: Antimicrobial wound treatment cream
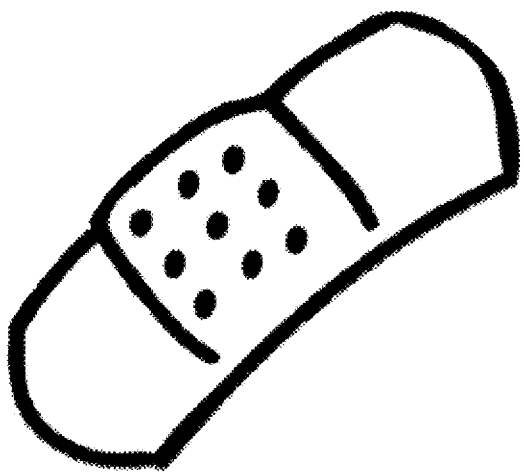
Figure 13: Antimicrobial and flexible wound dressing Left: Functionalized cuprous oxide; from top 1000x, 100x, 10x dilutions.

Right: Non-functionalized cuprous oxide; from top 1000x, 100x, 10x dilutions.

ANTIMICROBIAL COMPOSITIONS FOR USE IN WOUND CARE PRODUCTS

CROSS REFERENCE TO RELATED APPLICATIONS

This application is a continuation-in-part of U.S. application Ser. No. 14/089,146 filed on Nov. 25, 2013, which application is related to and claims priority from U.S. Provisional Patent Application Ser. Nos. 61/800,122 filed on Mar. 15, 2013; 61/820,561 filed on May 7, 2013, and 61/881,318 filed on Sep. 23, 2013; which application Ser. No. 14/089,146 is a continuation in part of and claims priority to U.S. patent application Ser. No. 13/685,379 filed on Nov. 26, 2012 (now abandoned), which application Ser. No. 13/685,379 in turn is a continuation in part of and claims priority to U.S. patent application Ser. No. 13/480,367, filed May 24, 2012 (now abandoned), which application Ser. No. 13/480,367 in turn claims priority to U.S. Provisional Patent Application Ser. No. 61/519,523, filed May 24, 2011, and U.S. Provisional Patent Application Ser. No. 61/582,322 filed Dec. 31, 2011; The contents of all of the foregoing applications are incorporated herein by reference in their entirety.

FIELD OF THE INVENTION

The invention relates to antimicrobial compositions comprising surface functionalized particles of low water solubility inorganic copper salts, or such copper salts infused into porous particles, their preparation, combinations of these particles with other additives and antimicrobial materials, and application of the compositions for wound care.

BACKGROUND OF THE INVENTION

The antimicrobial effect of various metals and their salts have been known for centuries. Their germicidal effects increased their value in utensils and as jewelry. The exact mechanism of the germicidal effect of silver is still not entirely understood, although theories exist. One of these is the "oligodynamic effect," which qualitatively explains the effect on some microorganisms, but cannot explain antiviral effects. Silver is widely used in topical gels and impregnated into bandages because of its wide-spectrum antimicrobial activity.

Oligodynamic effects are demonstrated by other metals, specifically gold, silver, copper, zinc, and bismuth. Copper and copper alloys and compounds have long been used as a biostatic surface to line the bottoms of ships to protect against barnacles and mussels. Bacteria will not grow on a copper surface because it is biostatic. Copper alloys have become important netting materials in the aquaculture industry because they are antimicrobial and prevent biofouling and have strong structural and corrosion-resistant properties in marine environments. Organic compounds of copper are useful for preventing fouling of ships' hulls. Copper alloy touch surfaces have recently been investigated as antimicrobial surfaces in hospitals for decreasing the transmission of nosocomial infections.

Numerous scientific investigations have focused on the antimicrobial characteristics of the metallic copper and copper alloys, and have concluded that multiple mechanisms may be responsible for copper's antimicrobial effect, including increased production of reactive oxygen species such as singlet oxygen and hydroxide radicals, covalent binding of copper metal to reactive sites in enzymes and co-factors, interference with lipid bilayer transport proteins, and interaction of copper ions with moieties of microorganisms analogous to what have been proposed for silver ions.

The focus of the present invention is on low water solubility copper salts in wound care products such as wound closure products, wound dressings, lotions and gels, etc, wherein the compositions may be added to or incorporated in articles of manufacture which result in imparting these products antimicrobial properties. The materials of this invention have very high efficacy against a broad range of bacteria, viruses, molds and fungi, etc. These products include liquids and solids, wherein the solids include coatings.

SUMMARY OF THE INVENTION

The present inventors have made the surprising discovery that antimicrobial compositions comprising particles comprising certain low water solubility copper salts when combined with organic acids, their derivatives and their salts result in high antimicrobial activity. These compositions can be used for various wound care applications and can be combined with certain low water solubility silver salts or silver metal. Preferably, the pH of these compositions is between 1.5 and 8, and more preferably between 3 and 6 and most preferably between 3 and 4.5. When aqueous solutions containing compositions of this invention are used to incorporate them in solid products, the pH of these solutions should be in this range. When formulated in accordance with the teachings herein, these materials result in surprisingly effective broad-spectrum, fast-acting antimicrobial agents. These agents have much greater efficacy against a broad range of microbes or human pathogens, including bacteria, mycobacteria, viruses, molds and fungi, etc. than previously-known wound dressing materials.

The surface functionalized particles of these salts are preferably preformed so that these can be made uniformly and consistently. These are then added to or blended with other ingredients to form the desired compositions. That is, the surface functionalized salt particles are formed before they are added to the end-product or the formulation used to make the end-product or the article of manufacture. Similarly, porous particles with antimicrobial materials deposited into the pores are preformed prior to their incorporation in the end-product or the formulation used to make the end-product also exhibit exceptional antimicrobial properties. The functionalized salt particles or the porous particles may undergo additional chemical or physical reactions once they are added to the end-product or to the formulation used to make the end-product. Preforming of particles ensures easier uniform dispersion during the preparation of the compositions and also in the end product and their size is not dependent on the other compositional ingredients. A preferred size of the surface functionalized particles is below about 1,000 nm, preferably below about 300 nm. In some applications, an alternative to surface functionalized particles is use of porous particles with nanopores in which such low solubility salts are deposited. Amongst copper salts, cuprous salts are preferred due to their superior antimicrobial efficacy. A preferred class of cuprous salts is the group of cuprous halides, of which a particularly preferred salt is copper iodide, where both copper and halide ions provide antimicrobial characteristics.

The preferred organic acids are hydroxy acids, amino acids, acetic acid, ascorbic acid, erythorbic acid and hyaluronic acid. Further, α (alpha) and β (beta) hydroxy acids are preferred. Some of the preferred hydroxy acids are citric acid, glutamic acid, lactic acid, malic acid, tartaric acid, glycolic acid, mandelic acid, benzoic acid, salicyclic acid, hydroxy propionic acid and hydroxy butyric acid. Some of the preferred amino acids are aspartic acid, glutamic acid, arginine and lysine. The preferred organic salts are those that are formed of these acids using cations of sodium, potassium, calcium, copper and silver. One may use more than one acid or a salt in the compositions. When one uses a particular acid in a composition, then one may use a salt of the same or a different acid. Organic acid derivatives also include reactive products of carboxylic acid groups reacted by condensation reactions, e.g., with other carboxylic acids, anhydrides, polyols, amines, isocyanates, etc.

The surface functionalization agents used for the low water solubility salts, are those which are compatible with water and preferably have a minimum molecular weight of about 60 and more preferably at least about 80. Preferred materials for functionalization agents are surfactants, water soluble polymers and the same organic acids, their derivatives and salts which were listed earlier as additives to these compositions. Some of the preferred polymers are carboxymethylcellulose (CMC), Chitosan, polyvinylpyrrolidone (PVP) and copolymers of any of these polymers.

The above compositions may be combined with several other materials and matrices to form a complete formulation for a wound dressing. Several of these materials and matrices are discussed later. Typically the antimicrobial materials are suspended in a matrix material. The matrix material works as a carrier in which the antimicrobial materials are suspended temporarily or may act also as a binder in the finished product. The carrier is usually removed after application of the wound product. Typically the binder is a polymer or forms a polymer (e.g., by crosslinking or polymerization or physical association of oligomers and/or monomers). Some examples of polymeric binders are carboxymethylcellulose, chitosan, polyethylene oxide, PVP or copolymers and derivatives of any of these; and preferred examples of carriers are water and non-toxic alcohols and their mixtures.

The antimicrobial wound care products may be of several types—solids (including foams, textiles and coatings), gels, or liquids. Some of these are supports or bandages, where the antimicrobial compositions are applied to a substrate or a structure, or incorporated in the fibers of the wound care product. The substrate or the structure may be rigid or flexible, and the antimicrobial composition may be combined with other ingredients for wound healing and protection. The bandage may comprise several layers, one or more of which may carry the antimicrobial composition. The antimicrobial composition may also be a part of a cream or a lotion which is directly applied to the wounds as a topical treatment, and such treatments may be in a hydrophilic or a hydrophobic matrix (e.g., in petroleum jelly). One may also form a sprayable bandage, where the composition with other ingredients is sprayed onto a wound, and upon drying a protective bandage (or protective coating) is formed which may be removed later or it may degrade gradually (i.e. it naturally undergoes degradation) over a period of time as the wound heals. Wound care encompasses many applications such as minor cuts and abrasions, severe injuries, chemical interactions, burns, lesions and openings in skin caused by other problems—e.g., diabetes and other internal/external infections, surgical procedures, etc.

These and other features of the present invention will become apparent from the following detailed description and the accompanying drawings

BRIEF DESCRIPTION OF THE DRAWINGS

FIG. 3: Efficacy of antimicrobial materials of current invention against bacterial spores;

FIG. 7: Wound care bandage;

FIG. 8: Wound care foam bandage;

FIG. 9: Cast for hard tissue repair;

FIG. 10: Sutures for closing wounds;

FIG. 11: Sprayable bandage or sprayable wound care lotion;

FIG. 12: Wound care cream;

FIG. 13: Flexible adhesive bandage;

DETAILED DESCRIPTION OF EMBODIMENTS OF THE INVENTION

Introduction

Figure 1:
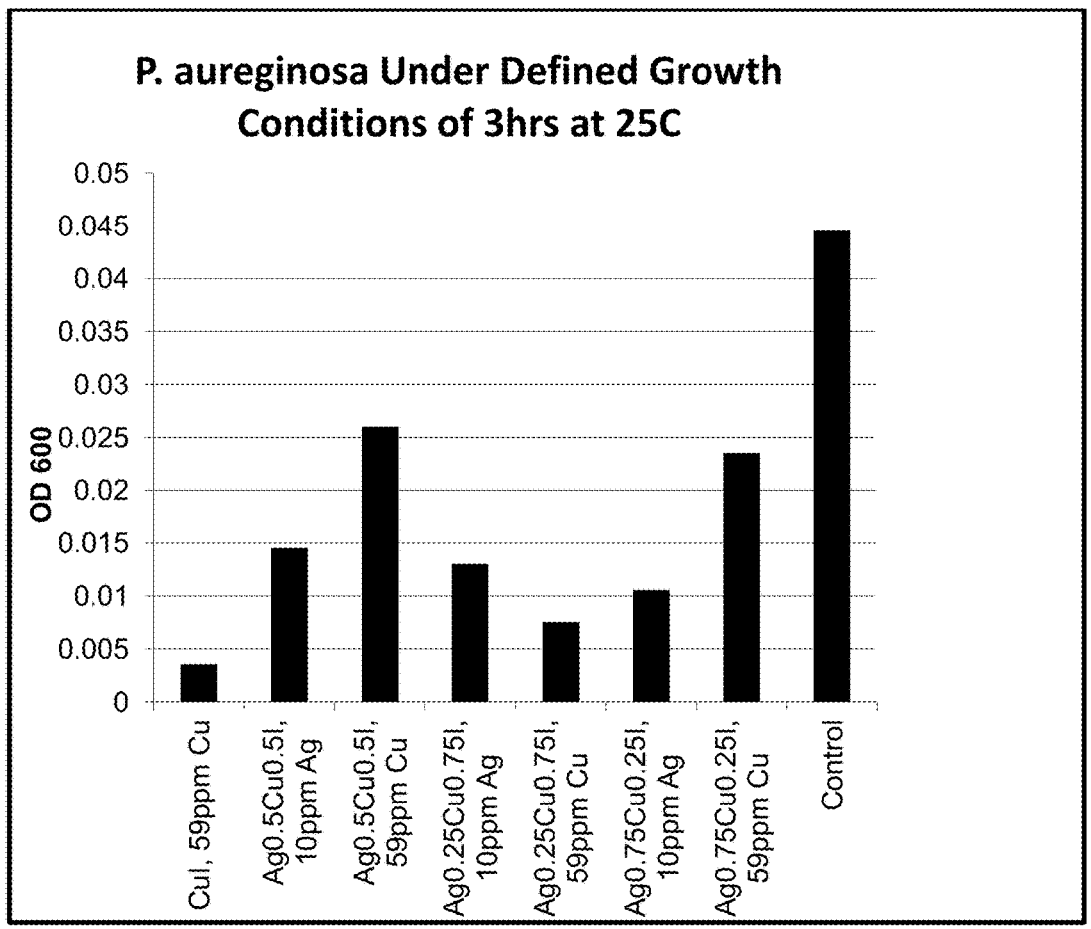
FIG. 1: is a plot of Optical Density (OD, Y-axis) against *P. aeruginosa* growth and/or inhibition by copper iodide particles and Ag—CuI mixed metal halides, and a control.

The present invention is concerned broadly with compositions and particles of low water solubility oligodynamic metals and their compounds, especially low water solubility copper salts, and with combinations of such compositions and particles with other known antimicrobials. These compositions may be added to articles of manufacture which result in antimicrobial products. These articles of manufacture include liquids and solids, wherein the solids include coatings and wound dressings. The present inventors have made the surprising discovery that particles of certain metal salts, especially low water solubility copper salts, when used along with organic acids, their specific derivatives and their salts in wound care products have very high efficacy against a broad range of bacteria, viruses, molds and fungi, etc. In addition, wound dressings containing these materials are also capable of killing bacteria in pre-formed biofilms. Low water solubility salts are those which have a room temperature water solubility of less than about 100 mg/liter, and more preferably less than about 15 mg/liter.

In particular, it has been discovered that the copper salts, particularly cuprous halide salts, and in particular copper iodide ("CuI"), when formulated in accordance with the teachings herein, are surprisingly effective as broad-spectrum, fast-acting antimicrobial agents. One method of incorporating the metal salts is by preparing them as surface functionalized particles. The average size of the particles is preferably less than about 1,000 nm, and more preferably less than about 300 nm. One preferred range is between 100 and 300 nm to obtain a good dispersion but to avoid difficulties associated with the definition of nano sized particles used by regulatory agencies such as US Environmental Protection Agency and US Food and Drug Administration. In some applications, a size between 3 and 100 nm is preferred where this size is required to achieve desired binding and transportation properties.

The salts may also be incorporated in porous particles with nanopores. The particle size of the porous particles is in the range of 1-20 µm, with a pore size in the range of 2 to 100 nm, and preferably in the range of 4 to 20 nm. The porous particles may also contain the organic acids and/or their salts. For both the functionalized and porous particles, the ions from the salts are available for producing the antimicrobial effect. The salts are those materials which in an aqueous environment result in an ionic dissociation so that metal ions and the corresponding anions are released.

Compositional Details

Salts of Low Water Solubility

The copper salt embodiments of the present invention include low water solubility copper salts, both inorganic and organic copper salts, preferably cuprous salts and more preferably cuprous halide salts. By way of exemplification the following copper compounds are illustrative but not limiting: Copper(I) iodide; Copper(I) chloride; Copper(I) oxide; Copper(II) oxide, Copper(I) acetate; Copper(I) sulfide; and Copper(I) thiocyanate. In some cases, surface functionalized low water solubility silver salts may also be added to the above compositions and may even be processed along with the copper salts. In that case, some of the preferred silver salts are silver iodide, silver chloride, silver sulfadiazine and silver oxide.

Low water solubility products are preferred as it is important that these salts impart antimicrobial properties by releasing a small number of ions, but are not solubilized by water and/or body fluids so that they are not absorbed in significant quantities into the body. Although the recommended dietary requirements for copper are 950 µg to about 2 mg for adults (and none is established for silver), but there could be a significant load of these salts in wound care products, which should preferably not be internalized in the human body (or an animal body for pet wound care products). Further, low solubility salts continue to release ions for long periods of time which conveys antimicrobial properties for hours, days and even weeks.

Halide salts are particularly preferred, since in addition to the metal ions (e.g., copper and silver), these salts also contain anions which have antimicrobial affects. For example, chlorine, bromine and iodine ions are used as antimicrobial agents in several cleaning and medical applications. As discussed later, the source of preferred metal halides may also be natural compounds. These minerals may also be used instead of synthesized halides, and formed into surface functionalized particles for use in antimicrobial applications. Some examples of minerals with their principal compositions as copper halides are Nantokite (CuCl) and Marshite (CuI). When silver salts are added as minerals, one may use Iodagyrite (AgI), Bromargyrite (AgBr), Chlorargyrite (AgCl) and Iodian Bromian Chlorargyrite (Ag(I, Br, Cl)).

U.S. Pat. No. 5,019,096 teaches the use of several antimicrobial agents in antimicrobial medical products including wound dressings. The agents which were not water soluble were ground in particles of size below 5 µm and then introduced in the products. This type of introduction is inefficient as one may not use most of the material since only ions from the surface are released leaving the core intact. Further, to distribute particles uniformly this requires large amounts of antimicrobial material, and such particles are difficult to keep suspended in low viscosity fluids.

Published US patent application 20070254044 understood that introducing non-water soluble silver containing materials was a challenge. They suggested using a soluble silver salt and a soluble salt of another material to be mixed in the formulation so that due to an exchange of ions between the two salts, insoluble amorphous silver salt particles (or salts with low solubility) were formed in-situ and were spreadable. Further, a soluble salt is formed as a result of this reaction. This method also introduces additional salts in the formulation, and the kinetics of formation of low solubility salts can vary depending on the other formulation components, viscosity, etc., thus requiring an optimization of each such formulation—which is cumbersome.

Copper salts have a range of water solubility characteristics. It is preferred that the copper salts of the present invention have low water solubility so that they will have slow and predictable copper cation release characteristics. In some formulations, it may be desirable to also add cupric (Cu(II)) or other more water soluble salts so that some fraction of Cu ions are available immediately. Further, Cu(I) cations have shown higher efficacy as compared to Cu(II) against the various microbes tested. At room temperature, copper salts of low water solubility are those which have a water solubility at room temperature of less than about 100 mg/liter. More preferred copper salts have water solubility less than about 15 mg/liter. In many applications lower water solubility is important, particularly where antimicrobial products come in contact with body fluids and water and long-term efficacy is required.

The human body regulates the concentrations of several elements (labeled as micronutrients). Interestingly both elements of copper iodide, i.e., copper and iodine, belong to this class of elements. On the one hand, the low solubility of copper iodide allows one to make products with high antimicrobial efficacy where such efficacy is retained for a long time; and due in part to body regulative functions, these ions are not toxic at the levels at which they are effective as antimicrobial agents.

For many (but not all) applications, the appearance and color of the coatings or the bulk products is important. For these applications, the antimicrobial material should not change the appearance significantly. For those applications, it is preferred that the additives do not change significantly the coloration of the product to which they are added. For many applications, the coloration of these materials may be assessed by looking at the color of bulk powders. In general, for applications where appearance is important, the color of the bulk powder (i.e., the color of the copper salt powders as received, for example, color of CuI powder as received prior to functionalization) should preferably meet certain requirements as discussed below relating to the L*a*b* color coordinates. Some of the products where this is important are creams (including creams with antimicrobial properties which are used for treatment of acne), and even including those creams and products used for antimicrobial personal care products (e.g., roll-on deodorants).

An L* value of 100 (maximum) indicates a completely white color and a value of 0 indicates a completely black color. Increasing negative values of a* indicate increasing green color and increasing positive values indicate red. Increasing negative values of b* indicate increasing blue color and increasing positive values indicate yellow. For a product with the additive and without the additive the difference in any one of the values of L*, a*, or b* should be less than ±5 units and more preferably less than about ±2 units. Sometimes we have also seen that for a low degree of color, the color of the bulk metal salt powder should preferably have a L* value greater than 65, and more preferably greater than 70, and most preferably greater than 80 when measured on a color scale of L*a*b*. The desirable values of a* and b* are dependent on L* value, and should be as close to zero as possible. As a rough guideline, when the L* value is 65, the a* and the b* values are preferably within ±5; when the L* value is 70, the a* and the b* values are preferably within ±15; when the L* value is 75, the a* and the b* values are preferably within ±20; and when the L* value is 80 or greater, the a* and the b* values are preferably within ±25 as long as these values are within the L*a*b* color sphere. Color may also be measured for functionalized particles in the dry powdered stat; and it is preferred that the powders exhibit low coloration along the above established guidelines. Table 1 indicates color coordinates of several metal salt powders.

TABLE 1

Color coordinates of as received powders

| Material | Source, Catalogue number | L* | a* | b* |
|---|---|---|---|---|
| BISMUTH (III) IODIDE | Sigma Aldrich, 341010 | 0.01 | 0.09 | 0.02 |
| GOLD (I) IODIDE | Sigma Aldrich, 398411 | 76.6 | −1.98 | 34.55 |
| SILVER BROMIDE | Sigma Aldrich, 226815 | 45.02 | −20.55 | 42.49 |
| SILVER IODIDE | Sigma Aldrich, 204404 | 78.05 | −7.13 | 20.28 |
| SILVER CHLORIDE | Sigma Aldrich, 227927 | 72.46 | 4.01 | 5.05 |
| COPPER (I) BROMIDE | Sigma Aldrich, 254185 | 42.02 | −29.36 | −3.45 |
| COPPER (I) IODIDE | Sigma Aldrich, 205540 | 72 | 2.54 | 10.85 |
| COPPER (I) CHLORIDE | Sigma Aldrich, 229628 | 76.35 | −4.46 | 14.93 |
| COPPER (I) THIOCYANATE | Sigma Aldrich, 298212 | 76.17 | 0.46 | 8.79 |

In wound care applications and many personal care applications, another important parameter is skin staining caused by use of these products. Wherever possible this staining should be minimized and should preferably be non-observable to the naked eye.

The silver halides also have a drawback in that the materials tend to exhibit coloration when exposed to light such as the sun. Hence for those products where exposure to light such as sunlight is anticipated, these halides may desirably be doped with other materials so as to reduce the darkening. One way of accomplishing this is to make compounds such as mixed metal halides (or doping one metal halide with another metal halide) to reduce discoloration but still preserve low color, low water solubility and other desirable attributes. Another approach involves forming silver halide particles with mixed anions. Additional aspects of mixed metal halides are also discussed in the section below. Yet another approach is to make compositions when functionalization agents are materials with strong UV absorption, or add antimicrobial compositions to those matrices which absorb UV. It should be noted that while some of the copper halides may also exhibit mild discoloration on exposure to light, the extent of such discoloration is markedly less than that of the silver halides, and any such discoloration which can also be reduced by doping. In addition, attractive economics of the material are also very important for a variety of applications. The cost of copper compounds, such as the preferred copper halides of the present invention, is notably smaller than that of silver compounds of equivalent chemistry (e.g., CuI compared to AgI).

Further embodiments of the present invention are directed to mixed-metal halides. In one embodiment, two different metal ion salts with different halide ions are mixed (e.g., mixing CuI and AgBr). In another embodiment, novel halide salts containing more than a single cation, or containing more than a single anion or containing more than a single cation and more than a single anion can be employed. In the mixed-metal halides of the present invention, at least one of the cations is copper metal cation. More preferably, all of the mixed-metal cations are oligodynamic metal cations. Embodiments include silver-copper halide, gold-copper halide, etc. For example, a metal halide of two metals with a common anion may be expressed as $M_1$-$M_2$(X), where $M_1$ is the first metal, $M_2$ is the second metal and X is the halide anion. Another combination is $M_1$-$M_2$($X_1$-$X_2$), where $X_1$ and $X_2$ are different halogen anions. Most preferred embodiments include silver-copper halides.

Embodiments may include halogens such as iodide, bromide and chloride. A preferred embodiment is Iodide. Some exemplary embodiments are (Cu—Ag)I, (Cu—Ag)Cl, (Cu—Ag)(Br—I), (Cu—Ag)(I—Cl), Ag(Cl—I) and Cu(Cl—I). The stoichiometric proportion in the mixed metal halides between the various anion and the cations may be any which can be formed and is suitable for the application. In some cases particles with solid solutions of several metal halides may be formed as taught in U.S. Pat. No. 8,563,020, the teachings of which on antimicrobial solid solution compounds and resulting products is incorporated herein by reference. In one embodiment, the particles preferably have more than 21% by weight of copper salts with a solubility of less than 100 mg/liter; more preferably the particles should have more than 51% by weight of such copper salts and most preferably these salts should be about more than 71% by weight.

In a further embodiment, these compositions, particularly compositions comprising copper halides especially copper iodide, may be combined with known antibiotics or other antimicrobial or antifungal agents. Such agents include other oligodynamic metals and their salts, other copper salts with different solubility characteristics, and the broad range of other antimicrobial and antifungal agents not based on metal cations. A partial list of such agents is provided in section entitled "Formation of wound care products and other ingredients"

One may also combine particles of different sizes/composition/solubilities to control the delivery rate and the longevity of the antimicrobial efficacy of the products in which such particles are incorporated. As an example, one may combine particles about 300 nm in size with those that are smaller than 30 nm, or one may combine particles larger than 300 nm in size with those that are smaller than 300 nm, etc.

For many applications, cost is an important issue. Addition of precious metals or their salts to the compositions of this invention can make antimicrobial materials less attractive economically. Since the copper salts of the present invention have shown high efficacy against a variety of microbes and are less costly than the silver salts, for many applications mixing copper halides with silver, gold, platinum or other precious metals and their salts is not necessary. If needed for specific applications, the precious metals and their salts may be utilized in much lower concentrations than if they were not combined with the copper salts.

Functionalizing Agents

An important embodiment of the present invention is the functionalization of the low water solubility metal salt particles. In functionalizing the surfaces of the particles, molecules are attached either chemically or physically to these surfaces. These functionalizing agents are preferably present while the particles are being formed, either during chemical synthesis, or during physical grinding (when the particles are being ground to a finer size from larger particles). The amount of surface functionalizing agent increases with decreasing particle size in proportion to the overall change in surface area exposed for functionalizing. Any ratio of the relative amounts of the metal salt particles and the functionalizing material may be used. Typically these are present in a weight ratio (metal salt:functionalizing agent) in a range of about 1000:1 to about 1:100 and more preferably a range of about 100:1 to 1:20. Using higher molecular weight functionalization agents helps to weaken this interaction between the particles and helps dispersion. It is preferred that the molecular weight of the surface functionalizing agent be at least 60, preferably at least 80 and more preferably at least 100. The functionalization materials may also be polymeric. When such particles are incorporated in a matrix, the matrix may itself comprise the material used for functionalization.

There are several reasons for functionalization of the particles and either one or more of these may apply for a particular application. One purpose of the functionalizing agents is to reduce the inter-particle interaction so that they disperse more easily into the matrix or medium into which they are incorporated. Related to this is the increased stability of dispersions of the particles in liquid media. Another important function of the functionalizing agents is to enhance their compatibility with the matrix, e.g., promoting adhesion with solid matrices. Another important function of the functionalizing agents is to increase the antimicrobial activity of the composition. Yet another important function of the functionalizing agents is to control the physical characteristics (solubility, transportation, etc.) or chemical reactivity of the particles in the matrix. The functionalization materials may also enhance the processability i.e., formation of the particles and/or improve processability of the compositions in which these particles are incorporated. The choice of functionalization agent(s) is dependent on the application or end-use and also its compatibility with the composition of the antimicrobial particles. In addition the choice of this agent is also dependent on the solvent system used to form these particles.

More specifically, the following surface functionalization attributes can be classified in any of the above categories; preventing particles from agglomeration (e.g., promoting suspension stability, particularly in liquid products and in liquid coating formulations) and enabling particles to attach to various surfaces of an object. The functionalization may also protect the particles by keeping the physical and chemical properties of the product in which the particles are incorporated from changing in a way that is undesirable. The functionalization may also assist in enhancing the antimicrobial action such as by facilitating the release of ions or the rate of release of ions generated from the particles and making these available for antimicrobial action. The functionalization agent may also assist in attaching the particles to the microbes or assist in the transportation of the ions or the particles themselves to the interior of the microbes.

The functionalization materials enhance processability by attaching to the surfaces of the newly formed particles efficiently so that these disperse in the medium and additional energy in processing is devoted to making new particle surfaces rather than wasting energy in breaking agglomerates of newly formed and nonfunctionalized particles (e.g., in a grinding process where the desired particle size can be achieved more efficiently when appropriate functionalization agents are present, i.e., in less time and/or with less use of energy). When these particles are incorporated in compositions (e.g., in polymers or coating compositions or liquid suspensions), these disperse easily and remain well suspended with lower inputs of effort. For example, a first functionalization material may be a polymer (e.g., homopolymer or copolymer of polyacrylamide, PVP, polyethylene oxide), and the second one is a monomer or a surfactant (e.g., reactive acid, silane, anionic surfactant such as SLS).

The antimicrobial properties for particles of this invention for comparative purposes may be determined in an aqueous suspension containing these particles. Such testing may be carried out with metal concentrations (e.g., Cu concentration present as CuI particles) of 60 ppm.

On exposure to the functionalized particles of the present invention, the populations of typical bacteria will be reduced by at least factor of 1000 ($Log_{10}$ 3) in one hour. In most cases, the reduction in bacterial populations in this time period will be at least a factor of 10,000 ($Log_{10}$ 4); and reductions as large as a factor of 100,000 ($Log_{10}$ 5) are commonly observed on exposure to the functionalized particles of the present invention. Even in periods as short as five minutes, reductions in bacterial populations of at least a factor of 10 ($Log_{10}$ 1) are obtained; and reductions larger than a factor of 1000 ($Log_{10}$ 3) are often observed. Even bacteria which are difficult to kill with antibiotics and other antimicrobial materials (e.g., silver)—such as *Acetinobacter baumannii* which has recently spread in US from the wounded veterans from Gulf—have been found to be susceptible to the present inventive materials, with reductions in bacterial populations similar to those cited here. In the case of mycobacteria, which undergo mitosis at a much slower rate than typical bacteria, reductions in bacterial populations of at least a factor of 1000 ($Log_{10}$ 3) are also obtained on exposure to the functionalized particles of the present invention, but in a longer period of 24 hours. For fungus, reduction of microbial populations of at least 100 ($Log_{10}$2) are observed in 24 hours. For viruses reduction of microbial populations of at least 1,000 ($Log_{10}$3) are observed in one hour. For yeasts reduction of microbial populations of at least 1,000 ($Log_{10}$3) are also observed with the particles of present invention in one hour. Even in periods as short as five minutes, reductions in yeast populations of at least a factor of 10 ($Log_{10}$1) are obtained; and reductions larger than a factor of 1000 ($Log_{10}$3) are often observed There are several methods to measure efficacy of the materials in wound dressings. In one method biofilms are formed, and then it is determined if a contact with a wound care product will kill the bacteria in the preformed biofilms. Since the bacteria are protected by a mucus substance, this is a challenging test to pass. The biofilms are typically grown over a time period of 24 hours and then incubated with the wound dressing for a period of 24 hours or less. Before and after the incubation bacterial populations are measured. These populations typically show a reduction in bacterial populations of at least a factor of 1000 ($Log_{10}$3), and routinely reductions of 10 million or more ($Log_{10}$7) are observed. In another method, the efficacy of a wound dressing is determined using zone of inhibition (ZOI) method. In Zone of inhibition (ZOI) testing, a volume of bacterial solution was pipetted onto the surface of a tryptic soy agar (TSA) plate and spread with a sterile glass rod until it was almost completely absorbed into the agar. The gauze samples (e.g., about 1 cm in diameter) are placed onto the agar surface and gently pressed with tweezers until complete wetting occurred between the TSA and the gauze. The plates were inverted and incubated at 37° C. overnight (~16 hours). After 16 hours, the plates were examined for a halo or a clear ringed area (ZOI) around the wound dressing, the rest of the area acquires an opaque look due to bacterial growth. The size (width) of this ZOI ring is an indication of the efficacy of the antimicrobial material. This ring should be at least 1 mm in width, and for many of the wound dressings of this invention, ZOI widths of 3 mm or more have been observed.

Another measure of bacterial reduction efficacy involves inoculating a solid wound care product (such as a dressing) with a bacterial solution. Then after one hour of incubation the product is subjected to a clear growth medium and incubated at 37° C.±2° C. If the bacteria are not killed by the antimicrobial material incorporated in the product during this period, then these will grow and soon make the solution turbid or cloudy. The longer the solution remains clear, the fewer bacteria or spores are present which are able to germinate and/or grow. It is preferred that this trait is shown for both Gram negative and Gram positive bacteria.

Besides contributing to the antimicrobial effectiveness of the particles of the present invention, the functionalization also contributes importantly to the stability of dispersions of the particles and facilitates the formation of particle-containing materials with exceptionally uniform distributions of particles. The stability of particle dispersions in liquid media is measured under certain time and temperature conditions and the chemistry of the liquid. In aqueous solutions, the behavior (e.g., non-settling and agglomeration) may be measured at room temperature over one day, one week or one month or even longer, with the specifics be determined by the intended use of the materials. The measurement conditions for any of the properties are specific to the end-use; but in all cases, use of selected functionalization agents provides enhanced stability of particles dispersions. Uniform particle dispersion in solid media is also attained by functionalization so that reproducible and superior properties are obtained with the use of smaller amounts of antimicrobial agents.

Both synthetic and natural polymers may be used for functionalization. The natural polymers include carbohydrates (starch and polysaccharides such as alginates) and its components (amylose and amylopectin), chitosan, glycogen and protein based polymers. Synthetic polymers include polyvinyl pyrrolidone (PVP) and their copolymers. PVP copolymers means all polymers which have any segments of polymerized vinyl pyrrolidone, e.g., block copolymers, graft copolymers, alternating copolymers, random copolymers, etc. Some of the preferred copolymers are those which have both hydrophobic and hydrophilic sequences, particularly for use in hydrophobic petroleum jelly based creams. Preferred comonomers for PVP copolymers are caprolactum, olefins and vinyl acetate. Examples of PVP/Polyolefin copolymers with varying amount of hydrphobicity are Ganex® WP-660, Ganex® V-516 and Ganex® P904LC available from Ashland (New Milford, Conn.). More examples of other synthetic polymeric surface functionalization agents include polyvinyl acetate, poly(vinyl alcohol) (PVA), polyamides (nylons, polyacrylamides), polyacrylic/methacrylic acid, copolymers of acrylic acid (including methacrylic acid), soluble cellulosics (e.g., carboxy methyl cellulose—hydrofiber and hydrocolloids), polyacrylamide, polyethylene glycols and polypropylene glycols or oxides (and their polymers and copolymers), polyolefins modified with maleic anhydride (e.g., OREVAC® polymers from Arkema Group, King of Prussia, Pa.) polymers with alcoholic groups, urethanes and epoxies. As taught in several places in this specification, block and graft (including comb like polymers) copolymers are suitable under a variety of circumstances as they can provide good compatibility and dispersion characteristics. One may also use biodegradable polymers and copolymers such as polylactic-PLA acid and poly glycolic acid-PGA comprising polymers. One may find that using PLA, PGA or polyacrylic acid in wound product formulation may reduce or eliminate the need of an organic acid, i.e., these polymers also substitute for the organic acid component.

Each of the above polymers may have a range of molecular weights, typically in the range of about 1,500 and 1,000,000 Daltons, although molecular weights less than 200,000 are preferred, and molecular weights less than 100,000 are most preferred. Several polymeric and/or non-polymeric functionalization agents may be used together in the same formulation.

When using block or graft copolymers, one may advantageously use those materials where sections (blocks, grafts, etc) in the copolymer have different properties in terms of ionic characteristics or their attraction/compatibility with water or organic solvents. For example, one block or graft may be hydrophobic or ionic, and another block or another graft or the main polymer chain may be hydrophilic or non-ionic, etc. Some examples of copolymers which may be used for functionalization are polyethylene glycol (PEG) and polypropylene glycol (PPG) dimethicones, sodium laureth-13 carboxylate, copolymer of methyl vinyl ether and maleic anhydride, bisamino PEG/PPG 41/3 aminoethyl PG-propyl dimethicone, amine functionalized silicones (amidomethicone) and block copolymers of PEG and PPG (e.g., triblock copolymer with various block lengths such as Pluronics™ available from BASF, Germany). Some of the block copolymers with hydrophilic and hydrophobic blocks are also considered as non-ionic surfactants as discussed below.

Embodiments of the invention also make use of surfactants for surface modification. Surfactants represent an important class of functionalization agents as they form a bridge or a link between the particles and hydrophobic or hydrophilic surfaces or media. The term surfactants includes nonionic, cationic, anionic and amphoteric surfactants, some specific examples being Brij®, Tween® (polysorbate), Triton® X-100, Igepal®, Merpol® (all of these registered products being available from Sigma Aldrich, Milwaukee, Wis.), benzethonium, benzalkonium, dimethyldialkylonium, alkylpyridinium and alkyltrimethylammonium cations with any anion, e.g., bromide, chloride, acetate or methyl sulfate, silicone-ethylene oxide/propylene oxide copolymers (e.g., OFX-0190, OFX-0193 and OFX-5329 from Dow Corning, Midland, Mich.), Sodium dodecyl sulfate (SDS), sodium capryl sulfonate, sodium lauryl sulfate, sodium laureth sulfate, cetyltrimethylammonium chloride or cetyltrimethylammonium bromide (all available from Sigma-Aldrich Co, Milwaukee, Wis.), silicone surfactants, fluorosurfactants (e.g., Novec surfactants from 3M (St. Paul, Minn.) such as FC-4430, FC-4432, FC-4434 and FC-5120), salts of organic acids. Other surfactants include fatty alcohol ethoxylates, alkyl phenol athoxylates, phosphate esters, acetylene diols (e.g., ethoxylated acetylene diols), salts of polyacrylic acid (e.g., sodium salts of polyacrylic acid) and soy lecithin. Anionic, amphoteric and nonionic surfactants are preferred, and anionic and non-ionic surfactants are most preferred. Natural or bio-engineered surfactants may also be used. For example supercharged proteins are found in protein caspid layers of viruses which self assemble like surfactants. These types of proteins when used as functionalizing agents or other surfactants may also disrupt and/or attach more effectively to the viral shells.

One may also use surfactants (including emulsifiers) to form emulsions of hydrophobic polymers and other materials (e.g., oils), wherein such emulsions are then used to modify the surfaces of the particles. Some examples include polyurethane emulsions, acrylic emulsions, fluorosilicone emulsions and epoxy emulsions. This method is particularly suitable where particles are made by grinding of larger particles of the antimicrobial materials in a liquid comprising a polymeric emulsion. The particles formed are functionalized by this emulsion. Alternatively, one may grind the antimicrobial material in presence of a surfactant and then add this to the polymeric emulsion. Optionally, the functionalized particles may be dried as a powder and then added to a polymeric emulsion. This emulsion may then be used to prepare a wound care product.

Use of mildly reducing characteristics are desirable when cuprous halides (e.g., CuI, CuBr, CuCl) or other cuprous salts are used as antimicrobial materials. These may be used along with other functionalization agents or be used as functionalization agents themselves. In the presence of mild reducing agents (or mild antioxidants), $Cu^+$ ions are prevented from oxidizing to $Cu^{++}$ ions. This is desirable because $Cu^+$ ions have superior antimicrobial properties. Acids in appropriate strength and/or concentration may also be used for this purpose. Examples of acids include mineral acids (e.g., hydrochloric acid, nitric acid, sulfuric acid), or organic acids including hydroxy and amino acids. Examples of some of the preferred reducing acids include acetic acid, ascorbic acid, citric acid, glutamic acid, lactic acid, tartaric acid, glycolic acid, malic acid, sorbic acid, erythorbic acid, thiodipropionic acid, sulfamic acid, adipic acid, gallic acid, alginic acid, caprylic acid, linoleic acid, cinammic acid, succinic acid and alkylbenzene sulfonic acids, such as dodecyl benzene sulfonic acid. Examples of non-acidic reducing agents include alcohols, polyols and aldehydes of the organic materials listed above, and some specific examples also include sugars, glucose, xylitol, sorbose, cinnamonaldehyde, etc.

Salts of many of the above acids (particularly containing cations of lithium, sodium, potassium, calcium, zinc, silver and copper) and esters of organic salts of the above acids may also be used and may be used as functionalization agents or combined with additional functionalization agents. Some examples of alkali salts of are mono, di and tri-sodium citrates, sodium ascorbate, sodium sorbate, sodium cinnamonate, sodium lactate, sodium palmitate, sodium oleate, sodium formate, calcium diacetate, sodium gluconate, sodium carboxy methyl cellulose, sodium caseinate zinc gluconate and zinc stearate. Some of these salts stabilize the $Cu^+$ ions and act as buffers to maintain the pH in a desired range.

Some examples of esters of the organic acids are lauryl gallate, ascorbic acid palmitate and various isomers of tocopheryl esters such as $\alpha$ tocopheryl succinate. When materials having low water solubility and compatibility with aqueous media are required, these materials may be used in conjunction with surfactants. One has to be careful in using excess/strong acids as they may also reduce $Cu^+$ to $Cu^\circ$ which may impart undesirable color or even cause precipitation. One may use hydrophillic acids and salts for hydrophilic systems and may use hydrophobic esters of the same acids in hydrophobic matrices, for example, ascorbic acid and gallic acid and their salts with lithium, sodium or potassium are water soluble and ascorbic acid palmitate and lauryl gallate are hydrophobic.

Functionalization agents may also provide other useful functions to a formulation. As an example, the functionalization agents may also have antimicrobial properties (such as many cationic surfactants, phenoxy ethanol, 1-2 octane diol, etc.). As other examples, salts of arginine and acidic polymers have been suggested for use in toothpastes for promoting oral hygiene (US 2009/0202456), and chitosans and curcumin have been suggested for use as antimicrobial materials; and all of these may be used as functionalizing agents.

Functionalization agents may have UV stabilization and/or UV absorption properties (e.g., benzophenones, benzotriazoles, acrylic esters and triazines), which can reduce photochromism or photooxidation, and may also have antioxidant properties as discussed earlier (e.g., ascorbic acid, butylated hydroxytoluene, furanones). The agents may also be dyes to impart certain colors or fluorescence properties. One may add more than one of the surface functionalizing agents with different attributes. This allows products to be made economically with low added cost. As will be discussed later, some of the processing technologies disclosed herein are particularly suitable for achieving this in a facile way.

Well dispersed fine particles in liquids or solids (including coatings, lotions, creams, etc.) provide enhanced interaction with microbes, and result in effective antimicrobial products requiring lower concentrations of the antimicrobial agents. For particles a few nanometers in size, the surface functionalization can also influence their transportation into the interior of the microbes, such as penetration through the lipid layers. Functionalizing agents can also facilitate interaction/adherence of nanoparticles to the surface of a microbe. These include surfactants, amino acids and combinations of amino acids and/or surfactants with peptides, polypeptides and carbohydrates.

Particles with appropriate functionalization may also impart unique characteristics and allow unique treatment methods. For example, materials under illumination or humid conditions or anaerobic conditions can exhibit modifications in their antimicrobial activity. As a specific example, a wound care cream or dressing may be applied uniformly to a skin patch, and then specific areas within this patch may be treated with radiation (such as UV, visible or IR light or ultrasound, etc). The functionalization agent may be selected so that it interacts with this radiation—e.g., it may absorb the radiation and locally heat the particles and/or skin and release the antimicrobial agent locally and may even drive the antimicrobial material deeper into the skin in a short period during treatment. After the treatment, excess cream or the dressing may be removed.

It has also been found that when certain amino acids are used to functionalize the surfaces of the oligodynamic metal-containing nanoparticles, enhanced antimicrobial activity is obtained. Some of the preferred amino acids include aspartic acid, leucine and lysine, although numerous other amino acids can also have efficacy. Also useful are combinations of amino acids, dipeptides, tripeptides and polypeptides.

Use of proper functionalization agents and formulation additions may also facilitate delivery of the antimicrobial particles to the interior of biofilms so that the embedded microbes can be destroyed, and can help delay or prevent the formation of biofilms. This can be very important in several applications, such as wound dressings, and represents an important and valuable aspect of the present technology.

Indeed it is remarkable that cation-based antimicrobial agents can be rendered effective against microbes in biofilms which provide an anion-rich environment. In contrast, if solutions of cations are employed against microbes in biofilms, it is found that large fractions of the cations never get to interact with the microbes in the biofilms as they complex with anionic species in the biofilms.

Other embodiments of functionalizing agents include carbohydrates such as mono- and di-saccharides and their derivatives, enzymes, glycols and alcoholic esters (e.g., Schercemol™ and Hydramol™ esters from Lubrizol (Wickliffe, Ohio)). Still other embodiments of functionalizing agents employ ligand-specific binding agents. For example, functionalization using autoinducer or quorum sensing molecules (e.g., N-undecanoyl-L-Homoserine lactone and N-heptanoyl-L-Homoserine lactone) may facilitate the delivery of the antimicrobial materials through biofilms. These may be selected from siderphores, e.g., enterobactin, which can provide superior affinity to the microbial cell walls. When these and other suitably selected functionalization agents are attached to antimicrobial particles which are larger than the channels in microbial cell walls), they can provide close microbe-particle attachment to them so that the ions released from the particles are transported into the microbial interiors more effectively. For example, some of the anionic or other fatty acid containing surfactants when used as functionalization agents may help the particles to attach to or disrupt mycolic acid containing layers in the cell membrane of the pathogen.

In some cases, the functionalization agents may use a multiple tier approach, where the particles are functionalized using a first material, and then this mixture is treated with a formulation containing a second material, where the second material may further functionalize the particles by interacting with the still-exposed particle surface or reacting/interacting with the end groups of the first functionalization material (i.e. the first functionalization material can behave as a linker). This sequence may be repeated multiple times. To serve as linkers, the preferred materials are surfactants or those which have at least two reactive or interactive sites on the material. Some examples of linkers are monomers with functionality equal or greater than two. Some specific examples are silanes (including silanated quats), isocyanates (e.g., diisocyantes), polyols (e.g., diols such as ethyelene diol and polyethylene oxide diol), polyacids (diacids such as adipic acid, sebaccic acid), materials with reactive hydroxyl and acid groups along with vinyl groups (e.g., acrylic polyols, methacrylic polyols), etc.

Yet other examples include cecropin, caprylic acid and monocaprylin. As another specific example, it has been demonstrated (Corinne K. Cusumano, et al., Sci Transl Med 3, 109ra115 (2011) (DOI: 10.1126/scitranslmed.3003021 "Treatment and Prevention of Urinary Tract Infection with Orally Active FimH Inhibitors") that mannoside compounds are effective in preventing uropathogenic *E. coli* infections in women by inhibiting the ability of the bacteria to bind to epithelial cells of the bladder via FimH receptors. One may use such compounds to modify the surfaces of particles of this invention to target *E. coli* with specificity—i.e., using mannoside compounds as functionalizing agents, In another embodiment, mannoside compounds may be included within the coatings used in urinary tract catheters.

Using functionalization agents, one may target specific microbes responsible for particular pathogenic infections. There is an abundant and expanding literature on receptors on cell surfaces to which microbes bind; and utilizing tailored compounds as functionalizing agents which interfere with such binding can readily be carried out. Beyond this, one of ordinary skill will be able to identify various ligand-target combinations to design any manner of ligand-specific targeting agents to use as functionalizing agents for the particles of the present invention. An example is affinity-based targeting mechanisms such as using certain inherent properties of microbes' external structures to target the metal halide nanoparticles. For example, the peptidoglycan layer of Gram-positive bacteria is a polymer of sugars and peptides which generally has a negative charge. Other polymers, such as PVP or PEG will be attracted to the peptidoglycan surface on the basis of hydrophobic interactions, and once there, will stick to and deliver the stabilized metal halide particles to the surfaces of the microbes, which in turn will deliver the antimicrobial-active ionic species. Likewise, Mannose-binding lectin (MBL) and/or Lipopolysaccharide binding protein (LBP) may be included as functionalizing agents. MBL recognizes certain carbohydrate patterns on microbial surfaces and LBP binds to lipopolysaccharide, which comprises a large fraction of the outer membrane of Gram-negative bacteria.

Another embodiment of functionalizing agents includes mercapto and thiol functionalizing agents in addition to the above-cited functionalizing agents. Thiol modifying agents useful for functionalizing the antimicrobial nanoparticles include aminothiol, thioglycerol, thioglycine, thiolactic acid, thiomalic acid, thiooctic acid and thiosilane. Combinations of thiol modifying agents can also be used in the present invention.

For some applications, particularly in preparing functionalized antimicrobial particles for wound care, cosmetic and personal care products, one may also use oils and extracts for surface modification derived from natural sources or synthetic methods. These may be used as functionalization agents or as additional additives as described later. These may also impart additional antimicrobial properties, promote healing, reduce itch, reduce pain, etc. Some examples include oils and extracts from *eucalyptus*, neem, cinnamon, clove and tea tree. One may prepare emulsions of these oils by adding a surfactant and then using these emulsions in preparing the functionalized particles. This preparation may be done in an aqueous medium, and then water may be removed if desired. More examples of functionalizing agents are glycerin, benzyl alcohol, stearyl alcohol, polyethylene glycol or polypropylene glycol diester of stearic acid, sorbitol, cetyl alcohol, carrageenans, disteearyldiammonium chloride, aloe leaf extract, cetearyl olivate, sorbitan olivate, caprylic/capric triglyceride, soyabean oil, olive oil, safflower oil, butylene glycol, potato extract, barley extract, sea-weed extract, wheat germ oil, cocamidopropyl betaine, sodium hyaluroate, algae extract, cholestrol, sucralose, witch hazel extract, hydrogenated lecithin, cyclomethicone, aqualine, linolic aciddimethicone copolyol and xanthan gum.

A judiciously selected surface functionalization of this type may also protect the particles from undesired interactions with their environments. This protection helps to maintain the particle integrity for longer in environments where the chemical and/or physical composition of the particles may be degraded in absence of such protection. This protection may allow the particles to be dispersed in media where the pH of the medium may degrade the particles, or where a chemical reaction may render them ineffective, or the particle material oxidation state may change due to high temperature, etc. By tailoring the chemistry and the porosity of these functionalization layers, it is also possible to control the release rate of the antimicrobially-active species from the particles. Further, the release properties may change depending on the functionalization agent. For example, the functionalization agent may soften with temperature or increase in porosity with increasing humidity, or under certain chemical and/or physical conditions or stimuli the functionalization agent may stop the passage of antimicrobial ions, or the functionalization agent may degrade or change its properties to allow antimicrobial material to be released at a greater rate.

Organic Acids and Salts

The formulations for wound dressings comprise both the particles with antimicrobial characteristics and at least one of organic acids and salts of organic acids. As discussed earlier, these acids and their salts may also be used as surface functionalization agents or used as co-functionalization agents (i.e., mixed or combined with other functionalization agents). Salts also include other compounds of these acids produced by hydrolysis/condensation reactions, such as those by reacting them with alcohols (to form esters) and amines. These acids and salts provide an enhancement in the antimicrobial characteristic of the surface functionalized particles. Mechanistically, this may happen by stabilizing the oxidation state of the antimicrobial ions (e.g., reducing the reactivity of cuprous ions from copper salts to oxidize to the cupric state, since cuprous ions demonstrate higher antimictrobial efficacy) or facilitating the release of the antimicrobial ions, or even the production of a synergistic antimicrobial effect. The use of these materials also helps in controlling the pH in the media (wound product) which comes in contact with the wound. A desired range of pH of wound dressings or creams (for aqueous based systems) is in the range between about 1.5 and 8, more preferably between about 3 and 6, and most preferably between about 3 and 4.5. The pH of the wound dressings may be measured by the pH of the aqueous suspensions used to make the product (e.g., making a wound dressing product by soaking or treating gauze or a substrate with this liquid).

The organic acids are chosen from the class of hydroxy acids and amino acids. In addition, acetic acid, ascorbic acid erythorbic acid, and hyalauronic acid may also be used. Of the hydroxy acids, α hydroxy acids are more preferred, although in some cases one may also use β hydroxyl acids. Preferred acids are glutamic acid, malic acid, lactic acid, tartaric acid, glycolic acid, mandelic acid, benzoic acid, hydroxy propionic acid and hydroxy butyric acid. The preferred salts of these acids are those which are formed using cations of sodium, potassium, calcium, copper, zinc and silver. Some of the preferred amino acids are aspartic acid, glutamic acid, arginine and lysine. In some cases mineral acids (e.g., HCl) may be used to control the pH, and organic salts may be used as buffering agents.

One may combine several of these acids and salts, e.g. an hydroxy acid may be combined with a salt of a different acid, or this may be further combined with an amino acid. The weight ratio of the organic acids and the salts together to the weight of the functionalized particles may cover a considerable range depending on the application. A preferred range for wound dressings is 20:1 to about 2:1, with a more preferred range of about 10:1 to 4:1. These ratios also assure that one uses the lowest amount of the functionalized metal halide particles to provide the greatest antimicrobial effect.

Porous and other Types of Particles

Other embodiments of the invention are directed to compositions having antimicrobial activity comprising a metal compound in an alternative form, where a porous particle is used as a carrier for the antimicrobial metal compound, where such compound is infused in the pores of the porous carrier particles. The terms "porous particle" and "porous carrier particle" are used interchangeably herein. The porous particles should preferably have interconnected pores. A preferred size of the porous carrier particle is below about 100 μm, more preferably below about 20 μm, and most preferably below about 5 μm. The average pore size (average pore diameter) of the carrier particles should be less than about 100 nm, preferably less than about 50 nm, and most preferably less than about 20 nm. Low solubility salts, such as antimicrobial metal halides are preferred materials for this infusion. Preferred antimicrobial materials which are infused in the pores are preferably low water solubility copper salts. In addition one may also infuse low water solubility silver salts, metallic silver and/or metallic copper in the same particles or another set of particles which may be mixed with particles containing copper salts. Of these, the low water solubility copper halides are preferred, and the most preferred halide is copper iodide. It is preferred that the surfaces of the porous particles (including the pore surfaces) are hygroscopic (an abundance of silanol or other hydroxyl groups on the surface leads to hygroscopic materials). This allows one to infuse the antimicrobial materials into these pores using aqueous solutions.

The porous particles may be of any composition, and may comprise organic or inorganic materials including polymers, metal oxides, carbon, etc. Polymeric materials may be thermoplastic or thermosetting types (crosslinked). One preferred class of porous carrier particles that can be used are "wide pore" silicas. The porous carrier particles may be of any shape, e.g., spherical, irregular, angular, cylindrical, etc. For example, SILIASPHERE™ silicas from Silicycle (Quebec, Canada) may be used. The preferred silicas have an average pore size (average pore diameter) in the range of 2 to 100 nm, more preferably about 4 to 20 nm. Another class of porous particles includes precipitated silicas, such as Zeothix™ and Zeofree™ from Huber Corporation (Atlanta, Ga.) and Sipernat™ from Evonik Industries (Evonik Degussa Corporation, Parsippany, N.J.).

The porous carrier particles containing antimicrobial compositions in their pores can then be incorporated into various products such as wound care creams, lotions, coatings and dressings. Since the size of the porous particles is larger as compared to surface functionalized particles, such particles are more suitable for solids and high viscosity products such as coatings and creams as they can remain suspended uniformly in these matrices. The porous particles need not be spherical, and can have other shapes such as plates, tubular bodies, etc. For example, a natural tubular material that is mined may be used for this purpose. These are called Halloysite clays and are available from Applied Minerals (New York, N.Y.). These clay tubes are typically between 0.5-3.0 microns in length, with an exterior diameter in the range of 50-70 nanometers and an internal diameter (lumen) in the range of 15-30 nanometers. In addition to imparting antimicrobial properties, the use of these clays in plastics in low concentrations can also lead to enhancements in modulus, strength and abrasion resistance.

The porous materials with metal compounds deposited in them are very different from materials where antimicrobial metal ions (e.g., silver and copper) are introduced in zeolitic or other matrices by ion-exchange mechanisms. Ion-exchange materials are typical synthetic or natural zeolites, bentonite clays, hydroxyapatites and zirconium phosphates, etc. Such ion exchange materials are crystalline, and as part of their crystal structure they contain molecular channels with a size generally less than 1 nm (although special ion exchange materials with larger pore sizes are available).

Also present in these crystal structures and easily accessible from their pores are labile cations (e.g., sodium, potassium, etc.), which can be ion exchanged with other ions such as silver and copper without collapsing the crystal structure and maintaining the electrical neutrality of the ion-exchanged material. Ion exchange is conducted using solutions of salts with high water solubility. For example, when conducting cationic ion exchange, the cations from the salt in the solution are exchanged with the cations already present in the ion exchange medium. For example, a zeolite or an ion-exchange porous material may contain sodium ions in the framework of the crystalline porous material. As an example, when this is exposed to a solution of silver nitrate in water (silver nitrate is highly soluble in water and results in silver and nitrate ions), the sodium ions in the zeolite will be replaced or exchanged with silver ions, so that gradually the aqueous medium will get more concentrated with sodium ions. After the process, the ion exchanged porous particles are washed to remove soluble salts and now have a fraction of sodium ions replaced by silver ions. The ion-exchanged materials are new compounds, i.e., new compounds are formed where in their molecular formula some of the cations have been replaced. Deposition of free metals or compounds does not result in formation of a new compound, but simply a mixture or a composite of the host matrix and the deposited material. Further, zeolites and the other ion exchange type materials are crystals with well-defined molecular channels. On the contrary, the preferred porous materials used in the present invention are amorphous and usually inexpensive, and their pores are typically larger and irregular.

In contrast to this, the salt or compound deposition process of the present invention is different and does not involve ion-exchange. The antimicrobial salt is deposited in pores of selected porous particles. For example, if one wants to deposit a copper salt or a silver salt, then both the anions and the cations of the salt are deposited. Further, the deposition process does not require that some other ion must be exchanged from the porous material. This deposition may be done from solutions which are aqueous or non-aqueous. When porous particles are soaked in these solutions, they absorb a part of the solution. The particles are then removed by filtration or centrifugation, etc. When these particles are dried, the solvent leaves and the solute or the metal compound is left behind in the pores or on the pore surfaces. In the present invention, compounds or salts (both cations and anions) are deposited in the channels (pores) of the porous materials. With this method, it is easy to deposit more than one type of antimicrobial salt or compound. One can also mix the materials of this invention (i.e., porous materials comprising deposited metal salts) with other antimicrobial materials to form the desired antimicrobial formulations. The other antimicrobial materials include the surface functionalized particles described earlier or even the ion exchanged materials. The products for wound care formed using these antimicrobial compositions may have additional ingredients as listed and described in the section "Formation of wound care products and other ingredients".

Ion exchanged materials also function in a different way during their use. When these are placed in service then they only release cations when these cations are replaced by other cations from the surrounding atmosphere. For example, an ion exchanged silver zeolite will only release silver ions when from the surroundings of the ion-exchanged particle it is able to receive an ion to replace silver, e.g., sodium, potassium, etc. With the deposited compounds of the present invention, no such substitution/replacement is necessary; and deposited CuI can release both $Cu^+$ and $I^-$ ions with no replacement.

For deposition of metal compounds within porous particles, an example of a procedure is provided. The metal compound is dissolved in an aqueous or a non-aqueous solvent and the porous particles are added so that the solution permeates the pores of the particle. For example, CuI is soluble in acetonitrile and also in dimethylformamide (DMF). This infusion of solution into the pores may be assisted by applying vacuum to the solution so as to extract air from within the particles to allow the solution to penetrate the pores more effectively. The particles are then removed (e.g. by centrifugation, filtering, etc.) while the pores still contain the solution. As the solvent is removed, the metal compound deposits in the pores or on the particle pore surfaces.

Solvent selection plays an important role in the use of porous carrier particles for delivery of inorganic metal compounds. Since an important part of the process is to ensure that solutions easily soak into the pores of the porous particles, it is required that the surfaces of the pores are compatible with the solvents used to form these solutions. In one embodiment, when the surfaces of the pores have hydrophilic properties, solvents with high dielectric constant such as water, ethanol, methanol, acetonitrile, dimethylformamide, etc., are easily wicked into the pores by capillary forces. The rate of release of ions can be tailored by varying the size of the porous particles, particle shape and pore geometry (including pore size). In general, smaller particle sizes and larger pore sizes will result in increased rates of ion release. The elongated or irregular particle shapes for the same particle volume and pore size as compared with spherical particle shapes will also result in higher ion release rate. One may mix different size particles and also particles with different pore sizes to tailor release properties to suit both short term and long term release of ions/antimicrobial salts in final use. These porous particles have high surface area, preferably greater than about 20 $m^2/g$, and more preferably greater than about 100 $m^2/g$.

In another process embodiment, non-water soluble (or low water solubility) metal halides may be formed or synthesized in the pores of the porous particles. As an example, low water solubility silver salt, such as AgI may be formed using aqueous solutions. A first aqueous solution is formed using silver nitrate (source of silver cations). The porous carrier particles are treated with this solution and removed once the pores are filled with this solution. The porous particles may be optionally dried to leave silver nitrate deposits in the pores. The treated particles are then treated with a second solution comprising sodium iodide (sodium iodide is used as a source of iodide anions). When the second salt solution permeates the pores of the particles and comes in contact with silver nitrate, AgI is formed due to the interaction between the two salts. Due to the low water solubility of AgI, it precipitates within the pores. The porous particles are removed and dried. These may also be washed in water to remove any soluble salts. Most of the insoluble AgI is expected to be physically trapped within the pores and is not removed by simple washing. The reaction between silver nitrate and sodium iodide is shown below.

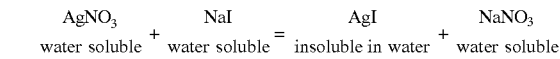

After drying, these porous particles may then be subjected to another series of similar treatments to precipitate more of the target metal or metal compound, or to precipitate a second compound or metal in the pores (e.g., depositing CuI or CuCl in pores which previously have been treated to deposit AgCl or AgI). To form CuI, one may substitute copper acetate monohydrate for silver nitrate. One may also form antimicrobial particles by mixing different types of porous particles comprising different compositions of metals and metal compounds. Optionally, if incorporation of surface functionalization agents is also required in these pores, because they may facilitate the release of antimicrobial material, then at least one of the initial solutions of water soluble salts may also include these surface functionalization agents. One particular embodiment comprises forming antimicrobial compositions by mixing two or more types of particles with different antimicrobial materials trapped in their pores. These formulations may then be added to products in order to form products with exceptional antimicrobial properties.

In a process embodiment of the present invention, one may also form antimicrobial porous particles with deposits of silver or copper metal or any of their alloys. Porous particles with these deposits can then be used to make antimicrobial products. The infusion of metals, such as silver metal in a porous carrier particle is generally performed by starting with an aqueous solution of a metal salt (e.g. silver nitrate with the surface modifiers (if used) dissolved therein) in water. The porous particles are added to this solution so as to infuse the solution into the pores. The porous carrier particles are then removed (e.g., by centrifugation, filtering, etc.) and optionally dried. The particles (wet or dry) are then added to an aqueous solution of reducing agent (e.g., 0.25% w/w $NaBH_4$) which reduces silver ions to silver metal which then precipitates in the pores.

The organic acids and their salts may be added to suspensions of the porous particles containing the antimicrobial salts, and may also be incorporated in the porous particles. This may be done before, during or after the low water solubility antimicrobial materials are deposited. Their deposition is also done using solutions which permeate the pores as discussed earlier. These may also be present in the solutions of desired antimicrobial compounds or those solutions which contain reactive components to form these antimicrobial compounds.

The particles of this invention may also be fabricated in a core-shell geometry, wherein the core may be a solid support and these are treated with solutions as described above so that these get coated with an antimicrobial material. That is, rather than using porous particles, solid particles are used. Examples of core materials are silica, titania, sand and carbon. The amount of antimicrobial material in a core-shell particle is preferably greater than 20% by weight, and most preferably greater than about 51% by weight.

Another variation in core shell geometry is where the antimicrobial particles are first formed in a desired size and then these are encapsulated in porous or permeable shells so as to allow the antimicrobial material or the ions to pass through. The concentration of metal halides and or the organic acids and salts will be similar to the values for functionalized particles.

Functionalized Particle Formation

Functionalized particles of a metal compound may be formed in several ways. The particles of the metal compound can also be pre-formed in the desired size and then functionalized in a subsequent step. However, a preferred method is to form these particles is in presence of functionalization agents. Particles of these compounds may be synthesized in presence of functionalization agents or larger particles (which are typically not functionalized to start with) are reduced to the desired size in presence of functionalization agents. As new particles or their surfaces are formed, they are more receptive towards being physically or chemically attached to the functionalization agents. One may also form the particles with a first functionalization agent and then in subsequent processing modify the first functionalization with a second (or additional) functionalization agent(s). Modification of the first functionalization agent means that the second functionalization agent may react with or interact with the first functionalization agent resulting in more desirable attributes. The second functionalization agent may act as a cofunctionalizing agent where it also modifies the surface of the particles. When the particles are used to make end-products, the particles are added to the product compositions or precursors in a functionalized state, i.e., the functionalization is not removed.

In one chemical method, the metal compound is dissolved in a solvent and the functionalization agent is incorporated in this solution. When the solvent is removed from this solution or the solution is mixed with a non-solvent, the solute particles form, and by choosing the appropriate conditions of solvent removal (or non-solvent addition rate), stirring, temperature, pressure, type and amount of functionalization agent relative to the metal compound, one can form functionalized particles of the compound in a desired size. For example, to form functionalized particles of CuI, one may use acetonitrile as a solvent to solubilize CuI, and incorporate PVP in this solution to form PVP modified CuI particles upon acetonitrile removal or addition of non-solvent such as water. Even if the particles agglomerate on drying, they disperse easily into the medium of the wound care product.

In another chemical method, the particles are formed by mixing at least two precursor solutions which are reactive. For example, one may mix an aqueous solution of copper acetate monohydrate with another aqueous solution of an alkali metal iodide, such as potassium iodide, where the mixing of the two solutions will promote reaction between the two solutes and produce precipitate of CuI. In this case, the surface functionalization agents may be incorporated in one or both of the above solutions. Again varying the parameters as described above along with the concentration of the precursors and their relative concentration of functionalization agents will lead to formation of particles of CuI in a desired size which are surface functionalized.

Non-chemical methods may also be used. Some of these involve mechanically impacting/grinding larger particles in presence of functionalization agents. Others involve physical or chemical vapor methods, where the particles are either formed in presence of functionalization agents or treated with functionalization agents immediately after their formation, preferably before they are subjected to ambient atmospheric conditions. In chemical vapor deposition, the particles are formed by reacting the gas phase of at least two components which react to form the particles of the desired compounds. In physical vapor deposition, the compounds (or their bulk powders and pieces) are evaporated or sputtered (typically under vacuum), and are cooled into smaller particles of the desired size or deposited as thin coatings which are then scrapped and/or pulverized to produce the desired particles. In the chemical vapor deposition process, the particles may be carried by a gas and transported through a liquid medium which has functionalization agents or the particles are subsequently subjected to the vapors of the functionalization agent(s). In the physical vapor deposition process, one may also treat the particles with the functionalization agent(s) as above, or the removed coatings may be ground in a medium which includes the functionalization agent(s).

A preferred method of forming the particles uses a feedstock of already formed large particles of an antimicrobial compound which are then reduced to the desired size in the presence of functionalizing agents. These methods are well described in U.S. application Ser. No. 14/089,146 filed on Nov. 25, 2013, which are included herein by reference. The size reduction is preferably carried out by taking the starting larger particles and the functionalization agents in a liquid phase, often aqueous medium, and then grinding these particles to a desired size in the liquid medium. During this size reduction, the functionalization agents attach to the newly formed surfaces and stabilize the particles, which also assist in reducing processing times. A preferred final particle size for most applications is less than about 1,000 nm. Also a preferred liquid medium is water, and the functionalization agent is soluble in or compatible with water. In addition to the functionalization agents, other materials may be added which may assist with grinding or promote linking of the functionalization agents to the particle surfaces, e.g., water soluble salts (with water solubility greater than 1 g/liter, surfactants, etc).

There are many advantages of the grinding process which include: (a) increased yield both in terms of amount and the concentration of the particles produced; (b) scalability on an industrial scale; (c) reduced waste both in terms of hazardous chemicals and also in terms of additional equivalents of starting materials that are typically required in chemical synthesis methods; (d) reduced energy requirements in terms of simplified processes and handling, removal and drying of larger quantity of solvents relative to the material produced; (e) reduced cost of production while adopting "clean and green" manufacturing methods; (f) increased versatility in terms of the chemistry of the functionalizing agent; (g) enhanced capability in being able to use more than one functionalization agent with different chemistries or even using more than one type of particles of materials being processed; (h) avoidance of the long development process which is typically required for each new set of particle composition and functionalization agent when chemical synthesis methods are used; (i) capability of imparting additional attributes to the antimicrobial materials via the functionalization agents; (j) increased ability to control the size of the resulting particles from a few nm to 1,000 nm or above; (k) improved ability to produce fine antimicrobial particles without introducing undesirable amounts of functionalization agents; (l) preparation of functionalized antimicrobial particles from natural antimicrobial minerals; and (m) use of more than one functionalization agent. Some examples of copper halide minerals found naturally are Nantokite (CuCl) and Marshite (CuI), and some of the silver halide minerals are, Iodagyrite (AgI), Bromargyrite (AgBr), Chlorargyrite (AgCl), Iodian Bromian Chlorargyrite (Ag(I, Br, Cl)). Another significant advantage of grinding is to be able to mix, homogenize and/or solubilize other materials which may be used in the product formulation. These other materials may also act as co-functionalization agents.

One preferred wet-grinding method uses bead mills. These mills typically comprise chambers in which hard ceramic or metal beads (grinding media) are vigorously stirred along with liquid slurries of the powders which result in grinding of the powders down to finer sizes. Preferred liquid (wet) media are aqueous. Preferred grinding media beads are about 1 mm or smaller and more preferably in the range of about 0.04 to 0.5 mm and most preferably 0.3 mm or smaller. Optionally, the grinding procedure may start with a larger bead size to grind initially the large chunks/particles of antimicrobial material to a smaller particle size and then using smaller beads perhaps in a different equipment to reduce the particle size further. In this case, functionalization agents may be present at each of the stages or only in the final stage.

Selective water soluble salts help with dispersion, i.e., stabilization of particles in a liquid medium or better dispersability in a solid medium. Typical solubilities of these water soluble salts are preferably in excess of 1 g/liter. These salts (organic or inorganic) typically have strong interactions with the material being ground and are preferably used in association with surface functionalization agents.

The addition of water soluble salts with antimicrobial properties may also help in providing antimicrobial efficacy at different time points (e.g., a burst of activity at shorter times). They may also provide buffering effects, or control the redox properties of the ions (e.g., stabilizing cuprous ions, or stabilizing iodide ions in compositions comprising cuprous and/or iodide ions), or provide compatibility with other ingredients in the composition. The antimicrobial compositions may be used as suspensions in aqueous or non-aqueous liquid media, or as solids.

Some examples of water soluble salts which have shown promise for processing aids for processing of metal halides of low water solubility (particularly while processing low water solubility copper and silver halides in aqueous solutions) include organic salts and salts of elements selected from at least one of lithium, sodium, potassium, calcium, magnesium, barium and zinc. The most preferred water soluble salts to be used for improving processability by grinding of the low solubility salts are those which have common anions. For example, to process low water solubility salts such as CuI and AgI, the more preferred salts with high water solubility will be LiI, NaI and KI, as both the low water solubility and the high water solubility salts have the same anions, i.e., iodide ions in this case. Typically as processing aids, high water solubility salts are used in low concentrations (small amount) relative to the material being ground. For example when low water soluble materials are being formed into particles, the relative weight percent of highly water soluble to low water soluble salt is preferably less than about 10% and more preferably less than about 3%. One may use more than one water soluble salt. Some other examples of water soluble salts are sodium acetate, sodium citrate, sodium cinnamate, sodium gluconate, similar salts of potassium, calcium, copper and silver; halide salts of lithium, sodium and potassium, calcium, magnesium, zinc and copper (cupric cations only); silver nitrate, sodium and potassium thiosulfate. However, as processing aids not all highly water soluble salts will work with all low water soluble salts. One has to be careful in coming up with the combinations, where processing is enhanced of the latter by only putting in a small amount of the highly water soluble salts.

As mentioned earlier, formation of particles by grinding also allows one to use more than one functionalizing agent, where these functionalization agents are added together or at different times during processing. The grinding parameter such as fluid flow rate, mill speed and temperature, etc., may be changed after each addition. A particularly useful concept is to process the particles using a first functionalization agent which helps in reducing the particle size efficiently and/or reduces the clogging of the mill, and then adding the second or other functionalization agents towards the end of the grinding process for it to interact with the particles and/or with the first functionalization agent. As a variation of this process one may prepare particles with the first functionalization agent and then with or without drying this material is processed again in a second grinding step (if it was dried then solvent will have to be added again) where the second functionalization agent is added. It is not necessary that the same solvent be used when two step grinding process is used. For example, when processing copper and silver salts with low water solubility in water, a first functionalization material for processing may be a hydrophilic polymer which is able to act as a functionalization agent (e.g., homopolymer or copolymer of polyacrylamide, PVP, polyethylene oxide), and the second one is a monomer or a surfactant which can perform as a functionalization agent (e.g., reactive acid, silane, anionic surfactant such as SLS). As discussed earlier, one may also use processing aids in the first and/or the second step.

To protect the health and safety of workers employed in such a facility or other downstream processor, it is important to minimize the possibility of getting the small particles airborne. An effective method of accomplishing this involves making the particle size of the dried powders containing the antimicrobial particles relatively large compared with the size of the individual nanoparticles. The particles of such dried powder particles will contain a number of the functionalized antimicrobial particles. The size of the dried powders should be greater than 1 micron, preferably greater than 10 microns, and most preferably greater than 100 microns. Such dry powders are easily handled and transported for downstream operators to use in paints, resins and other liquid carriers to create objects incorporating the functionalized nanoparticles. The larger particles do not get airborne easily and a 100 micron particle size is larger than the thoracic airways of human lungs. Further, with increasing size the particles are difficult to inhale, and flowability in processing also improves.

The dried powders may be used to make antimicrobial products by adding them to a liquid carrier or a solid carrier. Use of solid carriers includes compounding these powders with a polymeric material in the molten state. When these powder particles are added to the carriers (liquid or solid), the large particles will generally break down into smaller particles such as individual functionalized particles to produce a uniform dispersion.

In still other embodiments of the present invention, one may add other agents (preferably other polymers) before the drying step used to form the solid powders. This is useful for producing larger powder particles upon drying. Such added agents can increase the cohesiveness of the assembly of functionalized particles and effectively serve as a binder, which is useful in providing stability during subsequent handling. Polymeric functionalizing agents may provide or contribute to this function. Typically when the molecular weight of the functionalizing agent is less than about 500, it is advantageous to add a polymeric binder which preferably has a molecular weight greater than about 3,000 (this may also serve as a co-functionalization agent when added while the particle size is being reduced). As an example, one may use PVP, PEO or other polymers along with surfactants, where the surfactants have a molecular weight of less than 500 and the polymers have an average molecular weight of greater than 3,000. Preferably, the volume percent of the surface modifiers and the polymeric binder used to produce cohesive large particles should be in excess of about 20%, and more preferably in excess of about 40%.

To make such particles, where the functionalized particles are formed in a liquid, it is preferred that before drying the liquid, sufficient functionalizing agents and/or polymers (e.g., which can provide a binding function) are added, so that upon drying the volume percent of the functionalizing agent and the polymeric material is preferably greater than 20% or more preferably greater than 40%. The binding additives (if different from the functionalizing agents) may also be added after the grinding process is complete. As an example a formulation with 90% CuI and 10% PVP (both by weight as solids), when converted to volume fraction using their respective specific gravities of 5.67 and 1.2 would result in about 66% of CuI by volume and 34% PVP by volume.

Application and Product Areas

The embodiments of the present invention have utility in a wide range of antimicrobial applications. These products may be liquids, gels, solids or used as coatings on variety of solid objects. Some of these applications for wound and medical care applications are set forth in Table 2 and some for personal care applications are set forth in Table 3 below. The primary interest of this invention lies in wound dressings or wound care, which are generally listed as the first three application categories in Table 2. However, there are other applications in this table and in Table 3, where some aspect of wound care may be combined with them. In addition to preventing or reducing microbial infections, these materials of the present invention also provide an anti-deodorant function, as typically odor is also produced from bacteria. As discussed earlier, for many of the solid products, the antimicrobial materials of this invention may be infused in them or may only be present as coatings. Further, these antimicrobial materials may also be used with biocompatible products, which may be wound care products such as sutures, staples and artificial skins, etc., which are left inside the body and other medical applications such as implants.

TABLE 2

Representative applications of antimicrobial materials of this invention in wound care, other medical applications

| No. | Product/Application |
|---|---|
| 1. | Wound closure products including (sutures, staples; tissue adhesives, tapes, sealants, and glues) |
| 2. | Topical creams and lotions for medical use including those which are used on wounds and wound irrigation (including electrolyte solutions), cuts, burns, skin and nail infections; and during, prior or after surgical procedures and wound cleansing and debridement products (e.g. autolytic debridement products). |

TABLE 2-continued

Representative applications of antimicrobial materials of this invention in wound care, other medical applications

| No. | Product/Application |
|---|---|
| 3. | Wound dressings include dressings for treating skin ulcers, burns, trauma and surgical wounds. These may be related to other aspects of wound care and cover such as tapes, pressure relief products, moist and dry dressings (e.g., may include alginates, hydrocolloids, hydrogels, films, foams), negative pressure wound therapy dressing products, biological dressings (artificial skins and collagen products).<br>Some of the specific dressings are wipes, gauzes, foams, bandages, casts and supports, etc. |
| 4. | Dental adhesives, primers, sealants and composite fillings used for tooth restoration, and other tooth restoration products such as dentures, crowns, bridges and coatings including coatings on implants. |
| 5. | Medical and surgical gloves and masks |
| 6. | Medical devices and furniture used in medical facilities |
| 7. | Objects and coatings to prevent formation of biofilms, in medical applications, e.g., urinary tract and long dwell catheters |
| 8. | Internal or external medical devices to filter or treat body fluids |
| 9. | Coatings on bottles, containers or incorporated into the material of the containers used for containing medical or ophthalmic solutions |
| 10. | Clothing for medical personnel, including nurses and surgeons |
| 11. | Textiles including bedding towels, undergarments, socks, sportswear, uniforms and technical textiles (antimicrobial agent is in fibers or as coating on fibers or fabrics) for microbial and odor control |
| 12. | Self-disinfecting wipes |

TABLE 3

Representative applications of antimicrobial materials of this invention in personal care applications 1. Coatings or direct incorporation in personal items/use such as toothbrushes, hair curlers/straighteners, combs and hair brushes, brushes for cosmetic application (both for application of dry and wet materials)
2. Liquid cleaners/treatments/disinfectants (including sprays) for surfaces in household, industrial and medical facility applications
3. Nail polish including base and top coats
4. Shampoos for treating chronic scalp infections, antidandruff shampoos, hair detangling treatments, hair gel and other hair treatments
5. Incorporation in tooth paste, mouthwash and tooth brushes
6. Anti-odor formulations, including applications for personal hygiene such as spray and roll-on deodorants
7. Other body care products such as creams (including moisturizing and anti wrinkle creams, UV protection creams), shaving creams/gels, soaps (liquids, gel and solid), sanitizers, powders, mascara, blush, foundation and other cosmetic applications.

Formation of Wound Care Products and other Ingredients

The compositions of the present invention may be incorporated in liquid or solid carriers to yield products with antimicrobial properties. The liquid products may be called lotions. Many examples and methods of incorporation will be discussed below. Additional ingredients in some of the products are also discussed. Functionalized antimicrobial compositions of this invention may be added uniformly to thermoplastic polymer products which are extruded (including fibers and tubes) or molded (e.g., supports and scaffolds), or the products may only be protected by coatings containing the antimicrobial material. These thermoplastic products may be rigid or flexible; hydrophobic or hydrophilic depending on the dressing required for a given wound. Fibers made using the above process may be converted to yarns, fabrics, scaffolds, etc.; and the antimicrobial-containing product (e.g., fibers) can be combined with other non-antimicrobial-containing product (e.g., fibers) to obtain a final product with a desired level of antimicrobial activity at reduced cost. The materials may also be biocompatible polymers which may remain in the body or decompose to harmless products as healing progresses.

For thermoset polymers the functionalized antimicrobial materials of the present invention may be combined with monomeric formulations and then these may be used for molding, casting or coating, etc. The monomers or a part of the monomeric composition may also provide biodegradability to the thermosetting polymer. Curing of any of the thermoset materials/products may be done thermally or by radiation (UV, microwaves, etc).

The functionalized antimicrobial materials of this invention may be added to a variety of solvent (including water)-borne coating formulations, and articles of manufacture coated with these, where the coating is solidified by removing the solvent and/or by curing. One may also fabricate antimicrobial sutures and wound dressings (including burn dressings) using the materials of the present invention. Sutures, dressings, or other antimicrobial products and materials used to make final dressings, may consist of fibers, yarns, fabrics, foams, etc. These may be made antimicrobial by incorporating particles of this invention into them. One way of such incorporation is to mix the antimicrobial materials of this invention in the polymer and then extrude fibers containing the antimicrobial material. These fibers could then be used to make yarns which may be sued as antimicrobial sutures or converted to antimicrobial fabrics for wound dressings or other uses. The antimicrobial fibers may even be converted directly into non-woven fabrics. Antimicrobial fibers may even be mixed with non-antimicrobial fibers to still give an overall antimicrobial character to the products by using these blends. Antimicrobial dressings may also be formed by soaking fibers, yarns, gauze, fabrics and flexible open cell foams in aqueous solutions containing functionalized antimicrobial particles, removing excess liquids and drying these so that antimicrobial coatings are formed on them. When rigid foams or closed cell foams are used, it is preferred that the antimicrobial material is incorporated into the resin. Products containing antimicrobial materials made by the earlier process may be coated further with additional antimicrobial agents. One may also coat objects using powder coating a well known technique, where a solid polymeric powder (with the antimicrobial agent of the present invention incorporated in this polymeric powder) is applied on an object. The object is then heated to melt the powder to form a coating which is then solidified by curing (due to continued heating or a radiation treatment—such as UV) or by cooling of this coating.

Another area of application is antimicrobial adhesives (including pressure sensitive adhesives). These adhesives may also be biodegradable. These adhesives may be used as a component in the wound dressing or they may be used directly on the wounds. The antimicrobial additives of this invention are preferably added to these when they are in the liquid state.

The compositions of this invention may also be used for dental work. These include applications such as dental adhesives, sutures, primers, sealants and composite fillings and products such as dentures (including antimicrobial solutions to treat dentures), crowns, bridges and coatings including coatings on implants. The methods of incorporating the antimicrobial agents of this invention in solutions, sealants/adhesives and coatings for dental applications are very similar to those employed for other applications discussed throughout this patent application.

In another example, antimicrobial foams are used in wound dressings so that they would absorb any fluids exuding from the wounds and also ensure that these fluids do not promote colonization of microbes both to prevent infection from spreading and also to act as a deodorant. These antimicrobial foams may be formed by adding the functionalized particles to the monomers or materials which are used to produce this foam, or by first forming the foam, then treating (e.g., soaking and squeezing) the foam with a liquid composition comprising these particles so that they are trapped in the pores or attach to their surfaces.

Other embodiments of products formed from the antimicrobial compositions of the present invention include topical creams and liquid suspensions/solutions for both pharmaceutical (e.g., wound care, skin infection care, etc) and consumer product use (e.g., personal care products). They can impart one or both of antimicrobial and/or preservative properties. Preservative property typically means to preserve the product from spoiling under storage conditions—which may go bad due to bacterial and/or fungal growth. The antimicrobial particles of this invention may be added to either hydrophilic or hydrophobic cream compositions. As an example, materials compatible with petroleum jelly (a hydrophobic material), may be an appropriate surfactant or a polymer, as discussed in "Functionalization Agents" section.

The wound dressings may be formed by laminating or combining various layers where each layer provides different functions. A few or all of these layers contain antimicrobial agents. The feel or the drape of the dressings and their adhesion properties to the wounds may be modified by adding non-toxic surfactants, glycols, fatty acids and oils, etc. to the compositions containing antimicrobial particles. These dressings may have other medications or additives also incorporated in them (e.g., analgesics) in a post treatment or by adding them to the same solution which contains the antimicrobial particles. Additives may also include iron sequestering agents so that they would reduce the availability of iron for bacteria to grow and produce biofilms. Some of these agents are phosphates with preferential sequestering of iron, glycol proteins such as ovotransferrin, lactoferrin and sertotransferrin. Additives may also include more water-soluble antimicrobial materials to provide immediate release of antimicrobial anions or cations or both. Some examples of these salts include $CuCl_2$, $AgNO_3$, KI, NaI, etc. The additives may further include materials which provide enhanced transport of the antimicrobial materials through the mucus membranes, since the mucus agents form biofilms to protect the bacteria and spores within them. Examples of some materials which penetrate mucus effectively include glucose and xylitol. In addition these materials also have mildly reducing properties which would help in assisting to keep the state of cuprous ions stable. These additives may be also incorporated as functionalizing agents. To make wound dressings with broader efficacy, one may combine more than one type of metal salt or use solid solutions comprising multiple metal salts. The wound care products formed using these antimicrobial compositions may have additional ingredients as listed and described in the section "Formation of wound care products and other ingredients"

An antimicrobial lotion composition for wound management, comprising conventional Povidone-iodine (i.e., PVP-Iodine) could be enhanced by adding functionalized antimicrobial particles of this invention. It is preferred that in this case the particles of low water solubility metal halides (particularly copper halides) are functionalized by PVP and/or its copolymers. As a specific example, aqueous topical solutions of PVP and iodine (where iodine is about 8 to 12% by weight of the PVP) are commonly used as disinfectants for wounds and for disinfecting skin prior to surgery. As an example, BETADINE® is a commercially available PVP-iodine solution. Povidone-iodine (PVP-I) is a stable chemical complex of PVP and elemental iodine. 10% solutions in water are commonly used as a topical antiseptic. Such a metal halide-enhanced PVP-I solution would be formulated having about 88-99% PVP, 2 to 10% Iodine, and 0.005-5% metal as metal halide particles (preferably metal as metal halide from about 0.01 to 3%). on a wt/wt basis. One may also add additional water soluble halides, such as KI, NaI, LiI to the antimicrobial formulations, and their typical molar concentration ratio is about 0.001 to 0.1 as compared to concentration (molar) of the metal halides in the formulation. The addition of PVP to functionalize the surface of the metal halide could be carried out in a novel fashion. Such compositions could be made by wet-grinding larger particles of metal halide particles in PVP-I solution. As the particle size of the metal halides is decreased in the process, their surfaces also get functionalized by PVP-iodine and form stable suspensions.

The antimicrobial materials of this invention may also be used as co-additives to other drug/topical formulations including other antibiotic creams or liquid formulations (lotions) for curing or preventing dermal/hair infection control, wound care or related purposes. Some of the typical skin/topical/hair problems caused by microbial infection relate to acne, athlete's foot, nail infections, dandruff, etc., to just name a few. A typical concentration range of low water solubility copper salts (e.g., copper iodide and cuprous oxide) is about 0.005 to about 5%, preferably from about 0.01 to 3%. The antimicrobial materials of this invention may be added in a burn cream, which while assisting the repair of burnt tissue, will also keep infection away, or it may be mixed with other antibiotics, infection reducing/prevention analgesic and wound healing materials such as bacitracin, neomycin, polymyxin, silver sulfadiazine, polyenes, selenium sulfide, zinc pyrithione and paramoxine. Many of these compositions listed above are available in commercial products, and the antimicrobial materials of this invention can be added to them to result in a concentration that is most effective.

Published US patent application 20060269485 teaches the uses of antibiotic kits which deliver wound care topical materials through aerosol spray and forms a coating (a wound dressing) on the sprayed area. Although a large focus is on soluble antibiotic materials, in one or more embodiments, the antibiotic materials are metals which are suspended in the composition as particles, microparticles, nanoparticles or colloidal particles. The antibiotic metal can further be intercalated in a chelating substrate. This application also teaches using several silver salts some of which have low water solubility, but does not teach if these may be incorporated in aerosols by functionalizing them, and use of low water solubility copper salts is not taught. However, the teachings of this patent application are included herein by reference to make aerosol deposited wound dressings, where the antimicrobial agents of the application may be substituted by the surface functionalized particles of the present invention.

Although one may use small functionalized particles of this invention in a form as taught in the above US patent application, in many cases, it is not desirable to have very small functionalized particles present in the compositions, since during the spray operation, many of the particles could become airborne and enter the human airways. There are several ways of overcoming this while still using the antimicrobial materials of the current invention in a size less than 1,000 nm. One method is to form clusters of functionalized nanoparticles typically larger than 1 micron which stay together by using a binder which does not allow the nanoparticles to come apart in the spray solvent, but may disintegrate when sprayed on a wound as it comes in contact with moisture. For example, the binder may be water-soluble while the solvent for the spray (e.g., dimethyl ether, $CF_3CHF_2$, $CF_3CH_2F$) would be a non-solvent for the binder and would keep the clusters intact. Another method involves infusing the particles in porous particles which are greater than about 1 micron in size (as discussed in an earlier section) and incorporate these particles in the aerosol medium.

The wound care compositions and or products of the present invention may also contain any combination of the inventive particles with additional medicinal compounds and formulations. Some examples of medicinal compounds that may be added include, but are not limited to, other antimicrobials, antibiotics, other antifungal agents, other antiviral agents, nutrients (e.g., proteins, carbohydrates, amino acids (such as glutamine, arginine), vitamins (such as A, C and E) and trace elements (such as zinc, iron and magnesium and their compounds)), anti thrombogenic agents, anesthetics, anti-inflammatory agents, analgesics, anticancer agents, vasodilation substances, other wound healing agents, angiogenic control agents, anti-pruritic agents (anti-itch agents), angiostatic agents, immune boosting agents, growth factors, epithelialization promoting materials (e.g., gentamicin sulfate) and other biological agents. Examples of suitable antimicrobial agents and antibiotics include, but are not limited to, silver preparations (silver and silver compounds (e.g. silver sulfadiazine), in solution or as nanoparticles, silver containing zeolites), elemental iodine, povidone-iodine, biguanide compounds (e.g., polyhexamethylene biguanide), such as chlorhexidine and its salts; triclosan; penicillins; tetracyclines; aminoglycosides, such as gentamicin and Tobramycin™; polymyxins; rifampicins; bacitracins; erythromycins; vancomycins; neomycins; chloramphenicols; neomycin; polyenes; selenium sulfide; zinc pyrithione; paramoxine, maltodextrin; azoles including miconazoles; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity. Some natural wound healing materials are acemannan, chitosan, collagen, honey (e.g., medical honey, Manuka honey), sugar, etc. Depending on the formulation and the delivery method used, some of these products may be produced to treat humans or animals as a whole (e.g., by oral administration, injection, etc).

For most applications, the range of addition of the inventive active antimicrobial component (e.g., low solubility metal salt such as copper salt, or specific example being CuI) is about 0.001% to less than 5% by weight and preferably 0.001% to 3% by weight in the final end-use product. For those formulations where solutions (or suspensions) are used as end-use products, a preferred range of the active antimicrobial component (e.g., metal halide) is below about 3% by weight. Preferred concentration range of the active antimicrobial material in personal care products, disinfectants, etc., is also below about 5%, and preferably below about 3%. In some applications higher concentration of the active antimicrobial may be used, however, it is typically been our experience that when particles are functionalized, the improved dispersion results in use of lower concentration of these antimicrobial materials.

In flat-profile wound care products such as bandages, adhesive bandages and patches which contact the skin, the concentration of the materials may be expressed more appropriately as weight of the antimicrobial component/area of the product. In these cases a desired concentration of the antimicrobial metal salt (e.g., AgI, CuI, $Cu_2O$, etc.) is between 5 to 200 mg/100 $cm^2$, or preferably between 10 to 100 mg/100 $cm^2$ of the antimicrobially active area of the bandage. These numbers are typical for wound dressings in a thickness of about 2 mm, and may be optionally scaled with increasing thickness of wound dressing (i.e., may be doubled with double the thickness of the wound dressing) so that the metal halide particle concentration is still maintained at the interface of the wound dressing and the skin/wound. The metal halide particles which are used are surface functionalized.

The following examples are illustrations of the embodiments of the inventions discussed herein, and should not be applied so as to limit the appended claims in any manner.

EXAMPLES

Unless mentioned specifically in the examples, the following microbiological processes were used for testing of antimicrobial suspensions for efficacy against bacteria, mycobacteria, viruses, and fungi a. Microbial Assays The antimicrobial efficacy of the functionalized particles was evaluated using the following methods.

Maintenance and Preparation of Bacterial Isolates:

Test bacteria were obtained from the American Type Culture Collection (ATCC, Manassas, Va.) or The #27313, ATCC #9027), *Staphylococcus aureus* (ATCC #25923), *Mycobacterium fortuitum* (ATCC #6841), *Mycobacterium Smegmatis* (ATCC#14468), *Salmonella enterica* serovar *Typhimurium* (ATCC 23564), *Streptococcus mutans* (ATCC #25175), yeast *C. albicans* (ATCC#10231) and *Escherichia coli* 77-30013-2 (a copper resistant strain) was obtained from Dr. Chris Rensing and *Bacillus cereus* was obtained from Dr. Helen Jost at the University of Arizona, Tucson, Ariz. If other microbial strains were used then they are identified in specific Examples which follow.

Bacterial isolates used in these studies were routinely cultured on Tryptic Soy Agar (TSA; Difco, Sparks, Md.) at 37° C. or in Tryptic Soy Broth (TSB) medium at 37° C. on an orbital shaker at 200 r.p.m University of Arizona, Tucson, Ariz.: *Escherichia coli* (ATCC #15597), *A. Baumannii* (ATCC#19606), *Enterococcus faecalis* (ATCC #19433), *Pseudomonas aeruginosa* (ATCC. In the case of *M. fortuitum*, Tween 80 (polyethylene glycol sorbitan monooleate; Sigma Aldrich, St. Louis, Mo.) was added to the broth to a final concentration of 0.1% (v/v) to inhibit the formation of bacterial aggregates.

Preparation of Bacterial Spore Cultures:

One-liter cultures of *B. cereus* were grown in 2 L Erlenmeyer flasks containing trypticase soy broth (TSB; Difco, Sparks, Md.) inoculated with exponential-phase cells from trypticase soy pre-cultures. The cultures were incubated at 37° C. on a rotary shaker at 200 rpm. Spore development was visualized by phase contrast microscopy. The cultures were harvested after 72 hours. All harvesting and washing procedures were performed at 25° C. Spores were harvested by centrifugation and resuspended with one-quarter culture volume of a solution containing 1M KCL and 0.5M NaCl. Centrifugation was repeated and cultures were resuspended in one-tenth culture volume of 50 mM Tris-HCL (pH 7.2) containing 1 mg lysozyme/mL. Cell suspensions were then incubated at 37° C. for 1 hour followed by alternate centrifugation and washing with 1M NaCl, deionized water, 0.05% sodium dodecyl sulfate (SDS), 50 mM Tris-HCl (pH 7.2), 10 mM EDTA, and three additional wash steps in deionized water. Spore suspensions were heat-shocked at 80° C. for 10 min and stored at 4° C. until use (Nicholson, W. L. and P. Setlow. 1990. Sporulation, germination, and outgrowth. pp. 391-450. In Harwood, C R and Cutting, S M (eds.) Molecular biological methods for *Bacillus*. John Wiley & Sons, New York).

Maintenance and Preparation of Viruses:

Test viruses were obtained from the ATCC or Baylor College of Medicine Houston, Tex.: MS2 coliphage (ATCC#15597-B1) and Poliovirus 1 (strain LSc-2ab) Baylor College of Medicine Houston, Tex.

Poliovirus was propagated on monolayers of BGM cells (Buffalo green monkey kidney cells) originally obtained from D. Dahling (Environmental Protection Agency, Cincinnati, Ohio) with minimal essential medium (MEM, modified with Earle's salts; Irvine Scientific, Santa Ana, Calif.) containing (per 100 ml total volume) 5 ml of calf serum (CS; HyClone Laboratories, Logan, Utah), 3 ml of 1 M HEPES buffer (Mediatech Inc., Manassas, Va.), 1.375 ml of 7.5% sodium bicarbonate (Fisher Scientific, Fair Lawn, N.J.), 1 ml of 10 mg/ml kanamycin (HyClone Laboratories, Logan, Utah), 1 ml of 100× antibiotic-antimycotic (HyClone Laboratories, Logan, Utah), and 1 ml of 200 mM glutamine (Glutamax; HyClone Laboratories, Logan, Utah) with an incubation temperature of 37° C. in a 5% $CO_2$ atmosphere. The poliovirus was concentrated and purified using polyethylene glycol (PEG) precipitation and Vertrel XF extraction to promote mono-dispersion of the virus and the removal of lipids (Thurston-Enriquez, J. A. et. al., "Chlorine Inactivation of Adenovirus Type 40 and Feline Calicivirus", Appl. Environ. Microbiol. vol. 69 no. 7, p-3979-3985 (2003); Black et al. "Determination of Ct values for chlorine resistant enteroviruses," J. Environ. Sci. Health A Tox. Hazard Subst. Environ. Eng. 44: 336-339, 2009). The virus titer was determined using 10-fold serial dilutions in plaque-forming assays on BGM cell monolayers as described by Bidawid et al. ("A feline kidney cell line-based plaque assay for feline calicivirus, a surrogate for Norwalk virus." J. Virol. Methods 107: 163-167. (2003)). The virus stocks were stored at −80° C. until used in experiments.

Prior to experiments with poliovirus, frozen aliquots of a poliovirus stock solution (maintained at −80° C., titer previously determined) were thawed at room temperature (~24° C.). Sterile 50 ml conical tubes containing PBS were inoculated with the virus stock to obtain a final concentration of approximately $5.0\times10^6$ plaque forming units (PFU)/ml based on a final volume of 10 ml (obtained after the addition of the nanoparticle solution).

Maintenance and Preparation of Mold Isolates:

Test molds were obtained from the American Type Culture Collection (ATCC, Manassas, Va.) or The University of Arizona, Tucson, Ariz.: *Trichophyton mentagrophytes* (ATCC #9533), *Streptoverticilium reticulum* (ATCC #25607). *Penicillium* and *Aspergillus niger* isolates were obtained from Dr. Charles Gerba at the University of Arizona.

*T. mentagrophytes, Penicillium* and *Aspergillus niger* isolates were maintained on Sabouraud's agar (Neogen Corporation, Lansing, Mich.) slants at 25° C. *S. reticulum* isolates were maintained on Yeast Malt Extract Agar (ISP Medium 2) containing (per 1 liter deionized water), 4.0 g yeast extract (Beckton Dickinson, Franklin Lakes, N.J.), 10.0 g malt extract (Amresco, Solon, Ohio), 4.0 g dextrose (Hardy Diagnostics, Santa Maria, Calif.), and 20.0 g agar (EMD Chemicals, Gibbstown, N.J.). For preparation of *Penicillium* and *Aspergillus niger* spore suspensions, mature slant cultures containing fruiting bodies were washed repeatedly with 10 mL of sterile PBS to release spores. The spore suspension was then transferred to a 15 mL conical tube and vortexed to disperse the spores. For preparation of *T. mentagrophytes* spore suspensions, methods were adapted from the ASTM 2111-05 standard (ASTM Standard 2111, 2005, "Standard Quantitative Carrier Test Method to Evaluate the Bactericidal, Fungicidal, Mycobactericidal, and Sporicidal Potencies of Liquid Chemical Microbicides." ASTM International, West Conshohocken, Pa., 2005). A small section of mycelial mat from mature slant cultures was transferred to 3-4 plates of Sabouraud's agar. These were incubated for 10-15 days at 25° C. Mature mycelial mats were removed from the agar surface and placed into a 250 ml Erlenmeyer flask containing 50 ml sterile saline (0.85% NaCl) and glass beads. The flask was shaken vigorously to release conidia spores from the fungal hyphae and the suspension was filtered through sterile cotton to remove hyphae fragments.

1) Liquid Suspension Testing

Bacterial Reduction Assay.

Overnight suspensions were harvested by centrifugation (9,820×g, 15 min, 20° C., JA-14 rotor, Beckman J2-21 centrifuge; Beckman Coulter, Inc., Fullerton, Calif.) and resuspended in 100 ml of sterile PBS. The above centrifugation process was carried out two additional times to wash the cells and the final harvest was resuspended in 10 ml of PBS. Bacterial suspensions were then adjusted in PBS to an optical turbidity (measured using a BIOLOG turbidimeter, Hayward, Calif.) equivalent to a McFarland number 0.5 standard. Sterile 50 ml polypropylene conical tubes (Becton Dickinson and Company, Franklin Lakes, N.J.) containing PBS were inoculated with test suspensions to a final concentration of approximately $1.0\times10^6$ CFU/ml. Functionalized particles of the present invention were evaluated at either 10 ppm silver or 60 ppm copper. Test samples were then placed on an orbital shaker (300 rpm) at 25° C. for the duration of the experiment. At predetermined time intervals (e.g., 1, 3, 5, 24 hours), 100 µl samples were collected and neutralized with Dey Engley neutralizing broth (D/E; Difco, Sparks, Md.) at a ratio of 1:10. Bacterial samples were serially diluted in sterile PBS and enumerated using the spread plate method (Eaton et al., "Spread Plate Method," in Standard Methods for the Examination of Water & Wastewater, 21$^{st}$ ed., American Public Health Association, Washington, D.C., pp. 9-38-9-40. 9215C. 2005) with incubation at 37° C. for either 24 hours (*E. coli*, *P. aeruginosa*, *S. aureus*, *S. Typhimurium* and *E. faecalis*) or 48 and 72 hours (*M. fortuitum*, *M. Smegmatis* and *S. mutans*).

Evaluation of antimicrobial properties of porous silica particles:

Experiments for porous silica particles without antimicrobial salt and those comprising antimicrobial salt were conducted in 100 ml of sterile PBS in 250 ml Erlenmeyer flasks. Bacterial suspensions were added to a final concentration of $1.0 \times 10^6$ CFU/ml. Powdered silica samples were tested at 0.1 g dry weight per 100 ml of PBS. A control with bacteria but no added particles was also included. Powdered silica samples were added to each flask and kept in suspension by agitation using stir plates (VWR VMS-C7, VWR, Radnor, Pa.) for the duration of the experiment at 25° C. At predetermined time intervals (e.g. 0.25, 1, 6, 24 hours), 1 ml samples were collected and neutralized with D/E neutralizing broth at a ratio of 1:2. Samples were then diluted and enumerated as described before.

*Mycobacterium* and Yeast Assay

For *M. smegmatis*, *M. fortuitum*, or *C. albicans* the following was performed to address the problems such as clumping of cells and subsequent poor re-suspension in PBS for these organisms. For these three species, 0.1 ml of the unwashed cultures were used as the inocula in the antimicrobial efficacy experiments. The PBS inoculated with 0.1 ml of the Mycobacterial and *C. albicans* unwashed cultures contained an estimated $1.0 \times 10^7$ CFU/ml or $6.0 \times 10^5$ CFU/ml, respectively, based on a final volume of 10 ml (obtained after the addition of the Agienic particle solution). For each test solution prior to the addition of the Agienic particles, a 0.1-ml sample was removed from each and enumerated to determine the average initial microbial concentration at time (t)=0 hours. The calculations of the microbial numbers were corrected to reflect the final concentration per milliliter following the subsequent addition of the Agienic particle solution (i.e., the concentration in the final 10 ml total volume per tube). Conical tubes containing only the test microbial species in 10 ml of sterile PBS were included in the experiment as positive controls (No CuI particles or functionalization agents). In addition, stock solutions with only functionalization agents were added to separate tubes in equivalent volumes to their CuI containing counterparts and included in the experiments as additional controls. All of the Agienic particle solutions as well as the three control solutions (functionalization agents such as SDS, PVP, and PBS alone) were tested with duplicate samples at a concentration of 60 ppm Cu (wt/wt), which was present as Agienic particles of Cut Samples of 0.1 ml in volume were collected from each tube at predetermined time intervals (various time exposures depending on the species) and neutralized in Dey Engley neutralizing broth (D/E; Difco, Sparks, Md.) at a ratio of 1:10. The neutralized samples were then serially diluted (10-fold) in sterile PBS. For the bacteria (aside from the yeast), the surviving organisms were enumerated using the spread plate method on TSA with incubation at 37° C. for 24 to 72 hours as needed to observe the colonies.

Viral Reduction Assay.

For each test solution prior to the addition of the nanoparticles, a 0.1-ml sample was removed from each and enumerated to determine the average initial virus concentration at time (t)=0 hours. The calculations of the virus numbers were corrected to reflect the final concentration per milliliter following the subsequent addition of the nanoparticle solution (i.e., the concentration in the final 10 ml total volume per tube). Conical tubes containing only the poliovirus in 10 ml of sterile PBS were included in the experiment as positive controls (No antimicrobial particles or surface functionalization agents).

An appropriate volume of the provided stock solution of functionalized particles was added to the test solutions to obtain the desired metal concentration (e.g., Cu) in the 10-ml total volume. In addition, stock solutions containing surface functionalization agents (no metal salt particles) were added to separate tubes in equivalent volumes to their functionalized particle containing counterparts and included in the experiments as additional controls. All of the functionalized particle solutions as well as control solutions (functionalization agents and PBS alone) were tested with triplicate samples at a concentration of specific metal concentration (wt/wt, metal present as functionalized particles of the metal salt). For the duration of the experiment, both the test and control samples were placed on an orbital shaker (300 rpm; Model G33; New Brunswick Scientific, Edison, N.J.) at room temperature (~24° C.). Samples of 0.1 ml in volume were collected from each tube at predetermined time intervals (e.g., 1, 5, 15, 30, 60, 300, and 360 minutes) and neutralized in Dey Engley neutralizing broth (D/E; Difco, Sparks, Md.) at a ratio of 1:10. Control samples from the initial (t=0 minutes) and the final exposure time durations were examined. The neutralized samples were then serially diluted (10-fold) in sterile MEM without serum. The number of viable virus particles was determined using plaque-forming assays on BGM cell monolayers as before.

Mold Reduction Assay.

Sterile 50 ml polypropylene conical tubes (Becton Dickinson and Company, Franklin Lakes, N.J.) containing 10 ml PBS were inoculated with mold spore suspensions of approximately $1.0 \times 10^6$ CFU/ml. Functionalized particles of the present invention were evaluated at either 10 ppm silver or 60 ppm copper. Test samples were then placed on an orbital shaker (300 rpm) at 25° C. for the duration of the experiment. At predetermined time intervals (e.g., 1, 3, 5, 24, 48, 72 and 96 hours), 100 µl samples were collected and neutralized with D/E neutralizing broth at a ratio of 1:10. Mold samples were serially diluted in sterile PBS and enumerated with the spread plate method (Eaton et al., "Spread Plate Method," in Standard Methods for the Examination of Water & Wastewater, 21$^{st}$ ed., American Public Health Association, Washington, D.C., pp. 9-38-9-40. 9215C, 2005) with incubation at 25° C. for 48 and 72 hours.

Determination of Antimicrobial Activity by Optical Density Measurements.

Bacterial suspensions with or without antimicrobial particles where monitored for growth using a turbidimetric measurement. Turbid or cloudy suspensions indicated growth or increase in biomass whereas clear suspensions indicate no growth or no increase in biomass. A deficiency or lack of growth correlates to the effectiveness of the antimicrobial particles. Optical densities where monitored using a spectrophotometer such as an Eppendorf Bio Photometer cuvette reader (Eppendorf North America, Inc, Enfield, Conn.) or Biotek Synergy 2 multiwell plate reader (Biotek Inc., Winooski, Vt.).

Determination of Antimicrobial Activity Against Bacterial Spore Germination.

To determine antimicrobial activity against bacterial spores, sterile 2 mL polypropylene tubes were inoculated with *B. cereus* spore suspensions and treated with approximately 2 pM or 60 ppm of nanoparticles for 24 hours at room temperature (22° C.). After 24 hours of incubation, suspensions were pelleted by centrifugation at 13,000×g, and the supernatant removed and discarded. Pellets were resuspended in 200 µl of TSB. The tubes were then incubated for 24 hours at 25° C. and 37° C. Germination characteristics of *B. cereus* spores after 24 hours of incubation with nanoparticle chemistries were determined by optical density (Eppendorf Bio Photometer) at a wavelength of 600 nm (OD600).

2) Coated Surface Testing

Experiments for coated stainless steel or aluminum surfaces with and without functionalized particles were conducted based on the Japanese Industrial Standard Z 2801: 2000 method (JIS Z 2801:2000, "Antimicrobial products—Tests for antimicrobial activity and efficacy", Japanese Standards Association, Tokyo, Japan, 2000) with minor modifications. Prior to the experiment, 50×50 mm square coupons of steel or aluminum with the desired coating were disinfected with 70% ethanol twice and air dried. Overnight cultures of bacteria were washed and standardized as mentioned previously. Bacterial suspensions with a final concentration of $1.0 \times 10^7$ cfu/ml were prepared in PBS and 0.4 ml was inoculated onto each test surface. The inoculum was held in contact with the surface using UV sterilized 40×40 mm polyethylene film cover slips. A set of control surfaces coated with polymer but containing no functionalized particles was also inoculated for a zero hour time point to determine the initial inoculum concentration and at each time interval following to determine the change in organism concentration without antimicrobial. All inoculated surfaces were incubated in a sealed environment at 25° C. and >95% relative humidity (RH). At predetermined time intervals (e.g. 3, 6, 24 hours), the cover slip was aseptically removed and the bacteria were recovered by swabbing the surface and the cover slip with a cotton swab pre-moistened in sterile PBS. The swab was then neutralized in 1 ml of D/E neutralizing broth and the cotton tip of the swab was broken off into the tube containing D/E. Samples were then vortexed for 30 seconds and diluted/enumerated as described previously. Three replicate samples for each surface treatment were tested for each time interval in this manner. Bacterial reductions were determined by comparing the recovery of bacteria from the untreated control samples (polymer coated coupons without functionalized particles) to those recovered from treated samples containing functionalized particles at each exposure interval.

A revised version of the JIS method was later developed to enable more rapid testing of polymer coatings. The method above was performed with smaller surfaces (25×25 mm square coupons) and smaller polyethylene coverslips (20×20 mm). Surfaces were disinfected with a slightly different method to better preserve coating integrity; each surface was disinfected once with 70% ethanol and immediately irrigated with sterile deionized (DI) water before air-drying prior to the experiment. Surfaces were inoculated with 0.1 ml of a of $1.0 \times 10^7$ cfu/ml bacterial suspension and were incubated as previously described. At predetermined time intervals (e.g. 3, 6, 24 hours), samples were neutralized by completely submersing both the surface and the cover slip in 10 ml of D/E neutralizing broth in sterile polypropylene bottles. These bottles were sealed and sonicated (30 seconds, nominal main frequency 67 KHz, Cavitator® Ultrasonic Cleaner, Mettler Electronics, Anaheim, Calif.) to recover bacteria from the surface and cover slip. The D/E solution was diluted/enumerated as described before. Three replicate samples for each surface treatment were tested for each time interval in this manner. Bacterial reductions were determined as described previously.

Certain coatings were tested under more rigorous experimental conditions set forth in the EPA "Test Method for Efficacy of Copper Alloy Surfaces as a Sanitizer" with some modifications. Cultures of *Staphylococcus aureus* ATCC 25923 were grown for 48±4 hours. To simulate organic soil load, fetal bovine serum (FBS) and Triton X-100 were added to an aliquot of the overnight culture for a final concentration of 5% FBS and 0.01% Triton X-100. Test surfaces with the desired coating (25×25 mm square coupons) were disinfected as described for the revised JIS method above. Each test surface was inoculated with 20 µl of the culture with organic load and spread uniformly on the surface with a sterile glass rod and allowed to dry completely (approx. 20 min at 22° C., 20-45% RH). No cover slip was used for this experiment. A set of control surfaces coated with polymer but containing no functionalized particles was also inoculated for a zero hour time point to determine the initial inoculum concentration after drying and at the 120 minute time interval to determine the change in organism concentration without antimicrobial. At the end of the drying period, samples were incubated at room temperature (22° C., 20-45% RH) in sterile covered petri dishes for 120 minutes. Samples were then neutralized in D/E and sonicated for 30 as described previously. The D/E solution was diluted/enumerated as described before. Three replicate samples for each surface treatment were tested for each time interval in this manner. Bacterial reductions were determined as described previously.

3) Spray Antimicrobial Testing

The following procedure was used to determine the efficacy of functionalized particles used in spray applications. Test carriers (glazed 4.25"×4.25" ceramic tiles) were washed, treated with 10% bleach, and rinsed before being sprayed with 70% ethanol and allowed to air dry. Spray bottles were checked prior to testing to determine that each bottle dispensed similar volumes of liquid when sprayed. The bottles and spray nozzles were thoroughly washed and rinsed with DI water followed by 70% ethanol. The ethanol was allowed to dry and each bottle/nozzle was rinsed with sterile DI water. The bottles were emptied and the test samples were added aseptically to each bottle. In addition to test sprays, a solution of phosphate buffered saline (PBS) was used as a control (non-antimicrobial) spray. An overnight culture of the bacteria of interest was prepared in 100 ml of tryptic soy broth and centrifuged and washed in PBS as previously described. After the final centrifugation step, the bacterial pellet was re-suspended in 1/10 of the original volume (10 ml) in PBS. From this solution, 0.1 ml was inoculated onto each test carrier and spread uniformly across the surface with a sterile glass rod. Each carrier was allowed to dry completely before spray testing (approx. 20 min at 22° C., 20-45% RH). Each carrier was sprayed uniformly (fine mist setting) with the test solutions just to the point of covering the surface (approx. 2.5 ml). A set of samples sprayed with PBS were sampled immediately after spraying as a zero hour to serve as a control sample to determine the initial inoculum concentration on each carrier. The remaining surfaces were incubated at room temperature (22° C., 20-45% RH) in open air. At predetermined time intervals (e.g. 0.25, 1, 6 hours), bacteria were recovered by swabbing the surface with a cotton swab pre-moistened in sterile D/E neutralizing broth. The swab was then neutralized in 1 ml of D/E and the cotton tip of the swab was broken off into the tube containing D/E. Samples were then vortexed for 30 seconds. In some cases, where the spray samples were more acidic and thus were not completely neutralized at a 1:10 dilution, the sample was immediately diluted following the vortex step in 1:100 in PBS. In both cases, the neutralized sample was diluted/enumerated as described before. Three replicate samples for each spray treatment (including the PBS control solution) were tested for each time interval in this manner. Bacterial reductions were determined by comparing the recovery of bacteria from the control carriers (those sprayed with PBS solution) to those recovered from carriers sprayed with test samples containing functionalized particles at each exposure interval.

The following procedure was used to determine if sprays containing functionalized particles could impart some residual antimicrobial effect on sprayed surfaces. Test carriers and spray bottles were prepared as previously described for spray testing. Spray bottles were filled with test samples and phosphate buffered saline (PBS) was used as a control spray. An overnight culture of bacteria was prepared as previously mentioned for spray testing but was not immediately applied. Each test carrier was sprayed uniformly with the test solutions just to the point of covering the surface (approx. 2.5 ml). A set of samples sprayed with PBS was also included for each time interval. Each spray sample was allowed to sit undisturbed on the surface for a two minute conditioning time after which the surface was wiped with a paper towel to remove excess liquid. The surfaces were held at room temperature (22° C., 20-45% RH) for a predetermined "residual time" (e.g. 0, 3, 24 hours). Following this, 0.1 ml of the bacterial concentrate were inoculated onto each test carrier and spread uniformly across the surface with a sterile glass rod. The surfaces were incubated at room temperature (22° C., 20-45% RH) in open air. Immediately after inoculation and at predetermined "post-inoculation" time intervals (e.g. 1, 3, 6 hours), the bacteria were recovered by swabbing and neutralized as described previously for spray testing. The neutralized sample was diluted/enumerated as described previously. Three replicate samples for each spray treatment (including the PBS control solution) were tested for each time interval in this manner. Bacterial reductions were determined as described previously for spray testing.

4) Cream/shampoo Antimicrobial Testing

Experiments for cream, lotion, and shampoo based samples with and without functionalized particles were conducted based on the USP <51> method ("Antimicrobial Effectiveness Testing.", U.S. Pharmacopeia, Rockville, Md.) with minor modifications. Briefly, overnight cultures of bacteria were centrifuged, washed and standardized in PBS as detailed in previous sections. The bacterial suspension was diluted as needed for a specific experiment, ranging from $1\times10^7$-$1\times10^9$ cfu/ml. For each sample, 1 g aliquots were placed into sterile polystyrene tubes. In addition, 1 ml aliquots of PBS were used as a control solution. Each aliquot was inoculated with 0.01 ml of the washed bacterial suspension containing 10 times the desired final test concentration and mixed with a sterile wooden applicator or lightly vortexed depending on the viscosity of the sample. At predetermined time intervals (e.g. 7, 14, 28 days), samples were taken by adding 1 ml D/E neutralizing broth to the sample and vortexing lightly to mix. Samples were then diluted/enumerated and bacterial reductions were determined as described previously. All samples were tested in duplicate.

A zone of inhibition type assay was also used to determine the efficacy of functionalized particles in cream and petroleum gel products. Overnight cultures of bacteria were centrifuged, washed and standardized in PBS as described previously. The standardized bacterial solution was diluted to a concentration of $1\times10^4$ cfu/ml. Plates of tryptic soy agar (TSA) were inoculated with 0.1 ml of the diluted bacteria. A sterile agar punch (approx. 5 mm in diameter) was used to remove a plug of agar from each inoculated plate, creating a well in the center of the plate. Samples of cream or petroleum gel with and without functionalized particles were added until the entire well was filled with sample (approx. 0.05 ml). A plate with agar plug removed but without added sample was also included as a positive growth control sample. All plates were covered and incubated at 37° C. for 24 hours. The diameter of the resulting zone of inhibition (area with no bacterial growth or inhibited bacterial growth) was measured for each sample and compared with both the positive growth control and samples without functionalized particles to determine their relative antimicrobial efficacy.

5) Wound Dressing Antimicrobial Testing

The following procedure was used to determine the antimicrobial efficacy of wound dressings containing functionalized particles. Wound dressings were provided as sterile 10 mm diameter disks. Details of these are described in specific examples. An overnight culture of *P. aeruginosa* (ATCC #9027) was prepared as previously described but was not centrifuged or washed. Polycarbonate membrane films (25 mm diameter, 0.2 μm pore size, Whatman) were sterilized by autoclaving and placed in the center of TSA plates. The overnight culture was diluted 1:10,000 in PBS and 0.01 ml was inoculated as a single spot in the center of each membrane filter. These plates were incubated at 37° C. for 24 hours to allow for the formation of bacterial biofilms. After growth, each membrane filter was transferred to a fresh TSA plate. Wound dressing samples were moistened with 0.05-0.2 ml DI water and applied gently to the biofilm spot. The biofilms with wound dressings were incubated at 37° C. for 18 hours. Each wound dressing and membrane filter were transferred to 10 ml of D/E neutralizing broth, vortexed for 1 min and sonicated for 1 minute (described previously) to release bacteria from the surfaces. The neutralized samples were diluted/enumerated as described previously. Bacterial reductions were calculated and compared with the control samples containing no functionalized particles and biofilm control samples with no applied wound dressings.

Preparation of Materials and Antimicrobial Results

Example 1

Synthesis of CuI Particles Functionalized with PVP at Cu/PVP=1/3.3 w/w, and Testing Against Poliovirus 10% PVP solution was made by dissolving 1 g Polyvinylpyrrolidone, mol. wt.=10,000 (Sigma-Aldrich #PVP10) in 9 g water. 2.232 g of this solution was added into the solution of 0.211 g Copper(II) acetate monohydrate (Sigma-Aldrich #217557) solution prepared by dissolving 1.057 mmol of the monohydrate in 6.227 g water under stirring. Afterwards, 0.3168 g sodium iodide (2.114 mmol) dissolved in 5 g water was dropped slowly into the copper solution and stirred overnight. Next day, the CuI suspension was washed to remove the formed iodine by extracting 7-10 times 2.5-3 ml with diethyl ether. The remaining ether was separated from the solution by evaporation under vacuum and then water was added to compensate for the loss of weight during processing. The final concentration of copper based on the calculation of metallic copper is 0.48% w/w. Reaction:

$Cu^{2+}+2I^-\rightarrow CuI_2\rightarrow CuI_{(s)}+I_2$. 10% Aspartic acid solution was made using 0.296 g NaOH pellets (7.4 mmol) which was dissolved in 8.6 g water, 0.988 g Aspartic acid (7.4 mmol) (Sigma #A9006) added into the sodium hydroxide solution and then stirred until a clear solution was obtained. The aspartic acid solution was added to the CuI solution in a proportion so that the ratio of PVP/Aspartic acid (molar) was 1:2.5.

This solution was tested against Poliovirus (PV-1 LSc-2ab). The testing was carried out on Poliovirus (at 60 ppm copper concentration). Functionalized CuI particles were found to be particularly effective against poliovirus, with decreases in microbial populations 3.11 $\log_{10}$ reduction being found in 24 hours. A further encouraging result of the testing on poliovirus was the observation of the cell culture work carried out here, which showed no adverse effect of the functionalized particles on cell viability and reproduction in culture.

Example 2

Synthesis of CuI-PEG Dispersion w/pH Modifier

A dispersion of CuI surface modified with polyethylene glycol (PEG) was prepared in water using nitric acid as a pH modifier. To a reaction flask fitted with a stir bar was added 4.5 g of PEG (MW=10,000), and 0.0476 g CuI (99.999%) and 50 ml of acetonitrile. The mixture was stirred at room temperature for about 30 minutes to give a light green solution. The reaction flask was placed on a rotary evaporator and the solvent removed at 25° C. to a paste-like consistency. The temperature was then increased to 45° C. to complete removal of acetonitrile. This resulted in a yellow powder. This powder was dispersed in 50 ml of DI water and 0.05 ml (0.07 g) of concentrated nitric acid was added to form an off-white mixture. Upon stirring in the dark over night the dispersion became clear to give a light yellow dispersion.

Example 3

Preparation of Ag/PVP Dispersion

To a round bottom flask fitted with a condenser was added 50 ml of DI water (18 Mohm-cm) and 20 g of PVP (10,000 MW, Sigma Aldrich Cat.# PVP10). The mixture was stirred at room temperature to form a clear yellow solution. To this solution was added 0.04926 g of silver nitrate (≥99.0% ACS reagent Sigma Aldrich Cat. #209139) and the solution heated to 70° C. for 7 hours while stirring. During this time the reaction was followed by optical absorption with the formation of the Plasmon peak at 425 nm due to the reduction of silver nitrate to silver metal by PVP. The final dispersion of Ag nano-particles was orange/brown in color and was transparent. Dynamic light scattering on a dilute sample of the dispersion gave a mean particle size of 7 nm.

Example 4

Synthesis of AgBr/PVP Dispersion

A silver bromide dispersion was prepared by dissolving 20 g of PVP (10,000 MW, Sigma Aldrich Cat.# PVP10) in 40 ml of DI water (18 Mohm-cm). To this solution while stirring was added 0.0492 g of silver nitrate, (≥99.0% ACS reagent Sigma Aldrich Cat. #209139), resulting in a clear yellow solution. In a separate reaction vessel a reducing solution was prepared by dissolving 0.0357 g of potassium bromide (anhydrous powder 99.95% Sigma Aldrich Cat. #451010), in 10 ml DI water (18 Mohm-cm). This KBr solution was added drop wise to the $AgNO_3$/PVP solution to form a yellow/orange transparent dispersion of AgBr. Dynamic light scattering on a dilute sample of the dispersion gave a mean particle size of 4 nm.

Example 5

Synthesis of CuI/PVP Dispersion

To a reaction flask containing 50 ml of anhydrous acetonitrile, (99.8% Sigma Aldrich Cat. #271004), was added 10 g of PVP (10,000 MW, Sigma Aldrich Cat.# PVP10) and stirred to form a light yellow solution. To this solution was added 0.0476 g of CuI (98.0% Sigma Aldrich Cat. #205540) and after stirring for 30 minutes this resulted in a clear pale green solution. Then the bulk of the acetonitrile was removed under reduced pressure at 30° C. to form a viscous paste. The temperature was then increased to 60° C. to completely remove the solvent to give a pale green solid. To this solid was added 50 ml of DI water (18 Mohm-cm) and stirred to form a transparent bright yellow dispersion. Dynamic light scattering on a dilute sample of the dispersion gave a mean particle size of 4 nm.

Example 6

Synthesis of PVP-BASF-CuCl Dispersion

To a reaction flask containing 50 ml of anhydrous acetonitrile (99.8% Sigma Aldrich Cat. #271004) was added 14 g of PVP (BASF K17) and stirred to form a clear solution. To this solution was added 0.0239 g of CuCl (ACS reagent >99.0% Sigma Aldrich Cat. #307483) and after stirring for 30 minutes this resulted in a green/yellow solution. The bulk of the acetonitrile was removed under reduced pressure at 30° C. to form a viscous paste. The temperature was increased to 60° C. to completely remove the solvent to give a pale green solid. To this solid was added 50 ml of DI water (18 Mohm-cm) and stirred to give a transparent bright yellow dispersion.

Example 7

Synthesis of CuI/PVP-BASF+Acetic Acid+$HNO_3$

To a reaction vessel were added 4.05 g of PVP (BASF K17) and 50 ml of anhydrous acetonitrile (99.8% Sigma Aldrich Cat. #271004). This was capped and left to stir at room temperature to form a clear colorless solution. To this solution was added 0.0476 g of CuI (99.999% Sigma Aldrich Cat. #215554) and stirred at 25° C. for 30 minutes to form a transparent light yellow solution. The bulk of the acetonitrile was removed under reduced pressure at 30° C. to form a viscous paste. The temperature was increased to 60° C. to completely remove the solvent to give a yellow uniform solid. To this solid was added 50 ml of DI water (18 Mohm-cm) and stirred to give a cloudy white dispersion. This was left to stir for 3 days in the dark the dispersion remained cloudy with a light white precipitate. While stirring 0.3 ml of glacial acetic acid (ACS reagent ≥99.7% Sigma Aldrich Cat. #320099) was added and immediately the dispersion turned a orange/yellow color but was cloudy with a slight precipitate. To this mixture was added 0.05 ml of concentrated nitric acid (ACS reagent ≥90% Sigma Aldrich Cat. #258121) and the solution cleared up to give a transparent light yellow solution.

Example 8

Synthesis of CuI/VP-VA Copolymer-BASF+HNO$_3$ Dispersion

To a reaction flask containing 50 ml of anhydrous acetonitrile (99.8% Sigma Aldrich Cat. #271004) was added 6.75 g of the copolymer PVA-Vinyl acetate (BASF Luvitec VA 64) and stirred to form a clear solution. To this solution was added 0.0476 g of CuI (99.999% Sigma Aldrich Cat. #215554) and after stirring for 30 minutes this resulted in a green/yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of DI water (18 Mohm-cm) and stirred to give a cloudy light yellow slurry. Under stirring 0.05 g of concentrated nitric acid (ACS reagent ≥90% Sigma Aldrich Cat. #258121) was added to the mixture and it turned a light yellow color and was transparent.

Example 9

Synthesis of CuI/PVP-BASF+HNO$_3$

To a round bottom flask fitted with a stir bar were added 4.275 g of PVP (BASF K17) and 50 ml of anhydrous acetonitrile (99.8% Sigma Aldrich Cat. #271004). This was capped and left to stir at room temperature to form a clear colorless solution. To this solution was added 0.225 g of CuI (99.999% Sigma Aldrich Cat. #215554) and stirred at 25° C. for 30 minutes to form a transparent light yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of DI water (18 Mohm-cm) and stirred to give a cloudy light yellow dispersion. While stirring 0.07 g of concentrated nitric acid (ACS reagent ≥90% Sigma Aldrich Cat. #258121) was added to the mixture and it turned colorless and lightly cloudy with no precipitate. Dynamic light scattering on a diluted sample of the dispersion showed a bimodal distribution for volume fraction analysis with particles with peaks at diameter of 263 and 471 nm.

In another preparation following the above route, the proportion of components was changed. The amount of PVP (BASF K17) was 2.25 g in 50 ml acetonitrile. To this was added 0.0476 g of CuI (99.999%). This was processed as before and the dry powder was redispersed in 60 ml DI water. The solution was milky/pale yellow. After stirring 0.05 ml of nitric acid was added and stirred for two days. The solution became clear yellow with no precipitate. The solution remains stable after this process. The particle size was 4 nm.

Example 10

Synthesis of Ag$_{0.5}$Cu$_{0.5}$I and Ag$_x$Cu$_{1-x}$Br Nanoparticles

This method results in "solid solutions," meaning not separate distinct liquid phases of CuI and AgI but where one metal is substituted for the other randomly throughout the crystal or a non-crystalline lattice structure of the solid. For example, solid particles of Ag$_{0.5}$Cu$_{0.5}$I may be considered a solid solution of CuI and AgI where both are present in equimolar quantities, or one may consider CuI is about 51% by weight and AgI is 49% by weight. 10 g of PVP (10,000 MW, Sigma Aldrich Cat.# PVP10) was dissolved in 40 ml of DI water (18 Mohm-cm) and to this was added 0.0246 g (0.145 mmol) of silver nitrate (≥99.0% ACS reagent Sigma Aldrich Cat. #209139). To this pale yellow solution was added 0.0350 g (0.145 mmol) of copper nitrate trihydrate, (≥98% Sigma Aldrich Cat. #61197), to give a dark yellow solution. In a separate vessel 0.0481 g (0.29 mmol) of potassium iodide, (≥99.0% ACS reagent Sigma Aldrich Cat. #60400), was dissolved in 10 ml DI water (18 Mohm-cm) and added drop wise (0.34 ml/minute) to the silver, copper nitrate PVP solution. This resulted in a pale yellow dispersion of a solid solution of silver-copper iodide (Ag$_{0.5}$Cu$_{0.5}$I). Dynamic light scattering on a dilute sample of the dispersion gave a mean particle size of 29 nm.

Silver-copper-bromide nanoparticles were synthesized following the same procedure as for silver-copper-iodide using KBr instead of KI. Silver-copper-iodide-bromide nanoparticles were prepared in the same fashion using a combination of KI and KBr in a (1-y):(y) mole ratio.

Example 11

Synthesis of Ag$_{0.25}$Cu$_{0.75}$I Nanoparticles

Nano-particle dispersion of silver copper iodide solid was prepared according to Example #10 except that the molar concentrations of the metal ions were adjusted according to the formula Ag$_{0.25}$Cu$_{0.75}$I. Dynamic light scattering of a dilute sample of the dispersion gave a mean particle size of 10 nm. In this example, Ag$_{0.25}$Cu$_{0.75}$I particles are considered a solid solution of CuI and AgI where both are present in molar ratio of 25% AgI and 75% CuI, or one may consider CuI is about 71% by weight and AgI is 29% by weight.

Example 12

Synthesis of Ag$_{0.75}$Cu$_{0.25}$I Nanoparticles and Antimicrobial Activity of Ag$_x$Cu$_{1-x}$I Nano-particle dispersion of silver copper iodide solid was prepared according to Example 10 except that the molar concentrations of the metal ions were adjusted according to the formula Ag$_{0.75}$Cu$_{0.25}$I. Dynamic light scattering of a dilute sample of the dispersion gave a mean particle size of 8 nm. In this example, Ag$_{0.75}$Cu$_{0.25}$I particles are considered a solid solution of CuI and AgI where both are present in molar ratio of 75% AgI and 25% CuI, or one may consider CuI is about 21% by weight and AgI is 79% by weight.

Figure 2:
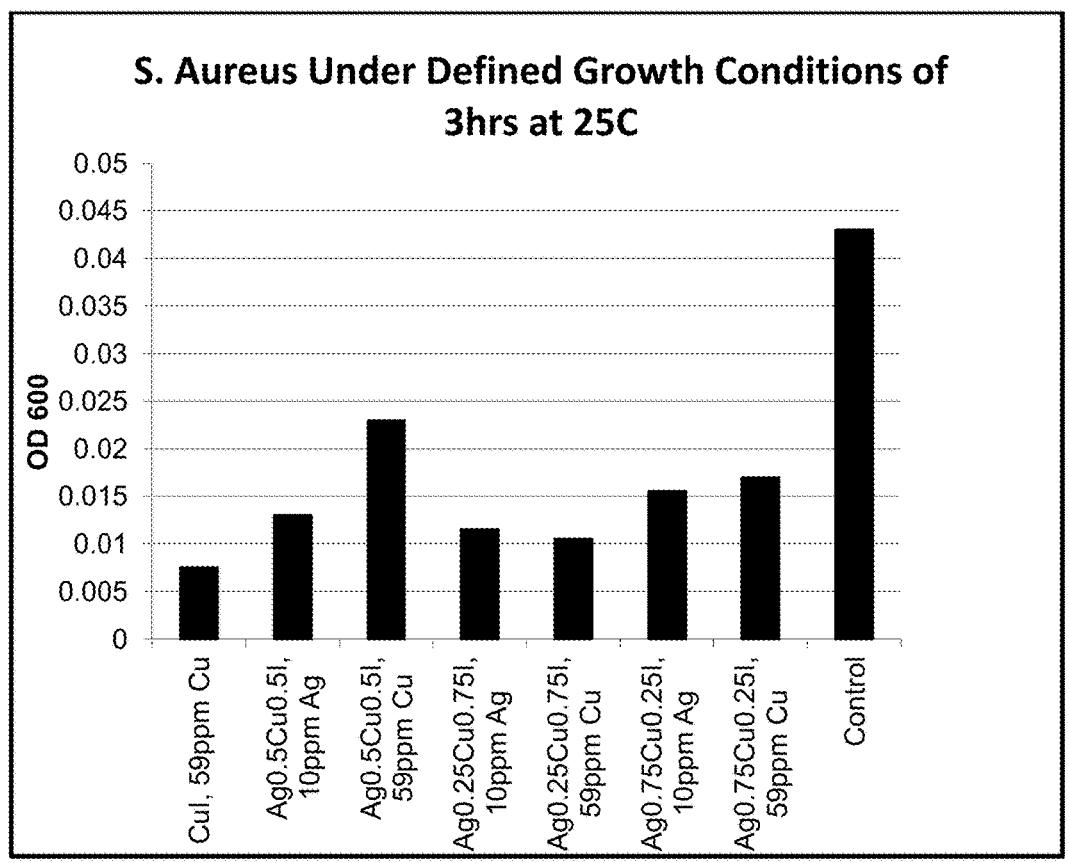
FIG. 2: is a plot of Optical Density (OD, Y-axis) against *S. aureus* growth and/or inhibition by copper iodide particles and Ag—CuI mixed metal halides, and a control.

Antimicrobial testing of Ag—Cu mixed metal halides (made in Examples 10, 11 and this one, i.e., Example 12) and their performance comparison with CuI was done using optical density method. FIG. 1 is a plot bar chart of Optical Density (OD, Y-axis) as a measure of growth against the effect of copper iodide particles and Ag—CuI mixed metal halides, and a control. Optical density was measured after treating the bacterial solutions with the nanoparticles of mixed metal halides (or solid solutions of mixed metal halides). Lower optical density implies growth inhibition and showed higher effectiveness. Particles of Ag$_{0.25}$Cu$_{0.75}$I, Ag$_{0.5}$Cu$_{0.5}$I, and Ag$_{0.75}$Cu$_{0.25}$I all showed effective antimicrobial properties against *P. aureginosa* (FIG. 1) and *S. aureus* (FIG. 2), however, none were as effective as CuI nanoparticles alone (CuI was made as in Example 5 by using the acetonitrile process). The data shows that with increasing copper content in the solid solution the efficacy of the material increased.

Example 13

Infusion of Metal and Inorganic Metal Compounds into Porous Particles

The copper halide-porous particle composition is demonstrated by two process embodiments which were used to infuse copper halide into porous silica carrier particles. Various types of porous silica particles were used from Silicycle Inc. (Quebec City, Canada). These were IMPAQ® angular silica gel B10007B hydrophilic silica. They had average particle size of 10 μm and a pore size of 6 nm, with pore volume of about 0.8 ml/g and a surface area of >450 $m^2/g$); or silica with particle size of 0 to 20 μm range (pore size 6 nm, surface area 500 $m^2/g$); or silica 0.5 to 3 μm in range (product number R10003B, pore size 6 nm).

Method 1

0.6 g of CuI (from Sigma Aldrich, 98.5% purity) was dissolved in 20 ml acetonitrile at room temperature (use of about 0.68 g of CuI would have saturated the solution). 1 g of silica powder (0-20 μm) was added to this solution. The solution was stirred for three hours at room temperature (this time period could have varied from a few seconds to more than three hours), then filtered through 0.45 μm nylon filter (from Micron Separations Inc., Westboro, Mass.) and finally dried at 70° C. The process may be repeated to increase the halide content. Using a spatula, the material is easily broken down into a fine powder. The analysis of this silica using inductively coupled plasma (ICP) atomic absorption spectroscopy at a commercial laboratory showed that the copper by weight was 1.88% of silica.

Example 14

Infusion of Metal and Inorganic Metal Compounds into Porous Particles

Method 2

In this method the solvent for CuI was 3.5 M KI solution in water. KI solution was prepared by dissolving 29 g of KI in 40 ml of deionized water, stirring and adding water to complete a final volume of 50 ml. The volume of the KI solution after mixing was measured to be 50 ml. 1.52 g of CuI was added and stirred at room temperature. The solution turned yellow immediately and by the next day it darkened somewhat. To 6 ml of this solution, 0.5 g of porous silica carrier particles (0.5 to 3 μm) were added and stirred for six hours. The silica particles were filtered and were then added to water so as to precipitate CuI trapped on the surface of the silica. The analysis of this silica using ICP AA instrument showed that the copper by weight was 1.46% of silica.

Example 15

Preparation of Polyurethane/CuI Dispersions by Wet Grinding

The samples were ground in a wet grinding mill produced by Netzsch Premier Technologies LLC (Exton Pa.), equipment model was Minicer®. Unless specifically mentioned, this equipment was used for preparing particles by milling in other examples. The grinding beads were made of YTZ ceramic (300 μm in diameter). The interior of the mill was also ceramic lined. 99.9% purity CuI was used to be ground to finer particle size using aqueous media. Two different types of aqueous media were used. In the first case the material was an aliphatic urethane 71/N aqueous dispersions (35% solids) sold under the Tradename of ESACOTE® obtained from Lamberti SpA, (Gallarate, Italy). This material is used for aqueous furniture varnishes and also for metal coatings. The second material was a PVP (Aldrich molecular weight 10,000) solution in water.

For the polyurethane dispersion, 10 g of copper iodide was added for every 100 ml of dispersion. As the grinding proceeded, the viscosity increased and the dispersion was diluted with a mixture of 7% n-ethyl pyrrolidone and 93% water by weight. 60 ml of diluents was added throughout the process. The samples started out with 50 grams CuI and 500 grams of the PU dispersion. It should be noted that the surface of the ground particles was being functionalized by the PU dispersion (which comprised of hydrophobic polyurethane and a surfactant amongst other additives). A total of 60 grams of 7% 1-ethyl-2-pyrrolidone was added periodically throughout the milling process as follows: 25 grams at 75 minutes, 10 grams at 105 minutes, 15 grams at 120 minutes, and 10 grams at 150 minutes. Approximately 100 mL of product was taken out of the mill at 75 and 105 minutes (before the addition of the solvent), and the remainder was pumped out at the 210 minute mark. At the end the process, the total solids content including CuI was 35%, the polymeric content was 27.2% and the % of CuI to that of the polymer was 28.6%. During grinding the maximum temperature was 38° C. After 210 minutes of grinding, the particle size was measured. The circulation speed and agitation speed settings on the equipment were both at six. Particle size measurement was conducted by HORIBA Laser Scattering Particle Size Distribution Analyzer (model LA-950A). The average particle size was 68 nm with a standard deviation of 7.4 nm. To test the stability of the suspension with ground particles, the particle size was measured again the next day which gave the mean size as 70 nm with a standard deviation of 8.2 nm.

Example 16

Preparation of PVP/CuI Dispersions by Wet Grinding

For the PVP dispersion, the formulation was 480 grams: 20 grams CuI, 60 grams PVP (Aldrich 10,000 MW), 400 grams de-ionized water. Grinding parameters were the same as in Example 15. Samples were pulled out after 45, 120 and 210 minutes of grinding under the same conditions as above (Example 15), the particle size (mean size) was respectively 920 nm (bimodal distribution with peaks at 170 and 1,500 nm), 220 nm and 120 nm respectively, when measured using the HORIBA apparatus as described above.

Example 17

Effect of CuI Particles on Inhibiting the Growth of Spores

FIG. 3 is a bar chart that shows the effect of CuI/PVP inhibition on *B. cereus* spores growth. CuI/PVP suspensions were made as in Example 5, and the copper concentration was 59 ppm in the final medium comprising CuI/PVP and the bacterial broth. This figure clearly shows the effectiveness of CuI/PVP in preventing *B. cereus* spores growth, and in fact even achieving a slight reduction as compared to the starting spore concentration.

Examples 18-23

Additional Antimicrobial Results Using Particulate Suspensions

Antimicrobial testing was carried out on the following microbes:

Ex. 18—*Pseudomonas aeruginosa* (ATCC 27313) (Table 5)

Ex. 19—*Staphylococcus aureus* (ATCC 25923) (Tables 6)

Ex. 20—*Streptococcus mutans* (ATCC 25175) (Table 7)

Ex. 21—*S. enterica Typhimurium* (ATCC 23564) (Table 8)

Ex. 22—*Penicillium* (Table 9)

Ex. 23—*Aspergillus niger* (Table 10)

Table 4 lists the samples, particle sizes and functionalization used in subsequent tables 5-10 with antimicrobial results. The particle size in this table was measured using dynamic light scattering (here and above, unless mentioned otherwise). In some cases the particle size was confirmed by optical absorption or by scanning electron microscopy (SEM). For measurement by dynamic light scattering, the particle suspensions were diluted in DI water by taking one to two drops of the suspension and adding several ml of water to ensure that a clear (to the eye) solution was obtained in a 1 cm path length cuvette. If the particles were large, the solutions were stirred just before measurement. Several measurements were made to ensure repeatability and reproducibility of samples. Most measurements were carried out using a Malvern Zetasizer Nano ZS light scattering analyzer (available from Malvern Inc, Westborough, Mass.) at ambient temperature, with a backscatter mode at a 173° scattering angle or using DynaPro NanoStar by Wyatt Technologies (Santa Barbara, Calif.), with a Laser Wavelength (nm)=661). Commercial polystyrene spheres with known size (60 nm) were used for instrument calibration. Some of the measurements were also made on the Nanotrac particle analyzer (available from Microtrac Inc, Montgomeryville, Pa.), also in the backscattering mode using a fiberoptic probe. The data was converted and reported in the volume fraction mode.

TABLE 4

| Sample number | Preparation method (Example#) | Metal or halide (CuI purity, %) | Surface Modification | Particle size*, nm |
|---|---|---|---|---|
| S10 | 4 | AgBr | PVP-Aldrich | 4 E |
| S11 | 3 | Ag | PVP-Aldrich | 7 E |
| S12 | 5 | CuI (98) | PVP-Aldrich | >15 E |
| S13 | 10 | $Ag_{0.5}Cu_{0.5}I$ | PVP-Aldrich | 29 |
| S14 | 5 | CuI (98) | PVP-Aldrich | >30 E |
| S16 | | | | |
| S17 | 5 | CuI (98) | PVP-Aldrich | 4 E |
| S18 | 4 | AgBr | PVP-Aldrich | 4 E |
| S19 | 4 | AgBr | PVP-Aldrich | 4 E |
| S26 | 5 | CuI (98) | PVP-Aldrich | 4 E |
| S27 | 7 | CuI (99.999) | PVP-BASF + $HNO_3$ + $CH_3COOH$ | 4 E |
| S28 | 8 | CuI (99.999) | VP-VA Copolymer-BASF + $HNO_3$ | 4 E |
| S33 | 5 | CuI (98) | PVP-BASF | 5 |
| S34 | 2 | CuI (99.999) | PEG(10k, Aldrich) + $HNO_3$ | 4 E |
| S34 | 6 | CuCl | PVP-BASF | 4 to 10 E |
| S35 | 3 | Ag | PVP-Aldrich | 6 |

TABLE 4-continued

| Sample number | Preparation method (Example#) | Metal or halide (CuI purity, %) | Surface Modification | Particle size*, nm |
|---|---|---|---|---|
| S36 | 4 | AgBr | PVP-Aldrich | 4 E |
| S37 | Purchased | AgI | PVP (AgI nano from ChemPilots) | 25 |
| S38 | 9 | CuI (99.999) | PVP-BASF + $HNO_3$ | 4 |
| S39 | 6 | CuCl | PVP-BASF | <10 E |
| S40 | | No AM material | Porous silica | Silica 0.5 to 3 μm |
| S41 | 13(1) | CuI (98.5) | Porous silica | Silica 0 to 20 μm |
| S42 | 13(2) | CuI (98.5) | Porous silica, | Silica 0.5 to 3 μm |
| S43 | 5 | CuI (98) | PVP-Aldrich | 6 |
| S51 | 16 | CuI (99.5%) | PVP-Aldrich (Ground) | 120 |
| S52 | 16 | CuI (99.5%) | PVP-Aldrich (Ground) | 220 |
| S53 | 16 | CuI (99.5%) | PVP-Aldrich (Ground) | 920 (bimodal 170 and 1,500 nm) |

*Bimodal

*"E" stands for those particles whose size was estimated. Estimated particle size is based on comparison to previously measured particle sizes for particles made according to the same process.

Example 18

Efficacy Against *P. aeruginosa* of Various Functionalized Particles

Table 5 shows the reduction of *P. aeruginosa* by exposure to various type of metal halide particles and their combinations, and also in different concentrations, sizes and surface modifications. All of these were tested with controls (meaning without metal halide particles or other known antimicrobial materials). The results from control are not shown, as they all uniformly showed either no growth or moderate growth of microbes under the same conditions. Experiments were conducted in duplicate. Further, in many cases, e.g., in Table 5, result R11 (at 24 hr), the results show >4.41 log reduction. In the same table at 24 hrs the result R40 also shows >5.19 log reduction. This does not imply that the result in the second case is more effective than in the first, all it says is that given a starting concentration of microbes, at that point there were too few too count. Thus use of the symbol ">" in all of these tables means that the maximum log reduction for that experiment was reached. That is to say, after the indicated time, there were no viable microbes seen. Sample number (starting with "S" in column 2) when stated will correspond to the sample number in Table 4. If exactly the same result number (Column 1, starting with "R") is used in various tables (Tables 5 to 10), then that corresponds to the same formulation and batch being tested for different microbes. For example R28 result in Table 5 was obtained on *P. aeruginosa*, and the same suspension was used to obtain the R28 result against *S. aureus* in Table 6.

TABLE 5

| | Sample | | Conc, PPM, | Time | | | | | |
|---|---|---|---|---|---|---|---|---|---|
| Result | # | Particles | Ag, Cu | 15 min | 30 min | 1 hr | 2 hr | 6 hr | 24 hr |
| R7 | S12 | CuI | 0, 59 | 4.32 | >4.47 | >4.47 | >4.47 | | |
| R8 | S11 + S12 | Ag + CuI | 10, 59 | >4.47 | >4.17 | >4.47 | >4.47 | | |
| R9 | S10 + S12 | AgBr + CuI | 10, 59 | 4.17 | >4.47 | >4.47 | >4.47 | | |
| R10 | S11 + S12 | Ag + CuI | 10, 6 | 0.09 | 0.07 | 0.08 | 0.20 | | |
| R11 | S12 | CuI | 0, 12 | 0.31 | 0.33 | 0.33 | 0.42 | 1.22 | >4.41 |
| R12 | S11 + S12 | Ag + CuI | 2, 12 | 0.3 | 0.3 | 0.42 | 0.46 | 1.32 | >4.41 |
| R13 | S10 + S12 | AgBr + CuI | 2, 12 | 0.34 | 0.25 | 0.34 | 0.41 | 1.13 | >4.41 |
| R14 | S11 + S12 | Ag + CuI | 10, 59 | 2.35 | >4.41 | >4.41 | >4.41 | >4.41 | >4.41 |
| R23 | S17 | CuI | 0, 59 | 2.30 | 2.97 | 3.81 | 4.76 | >4.77 | |
| R26 | S26 | CuI | 0, 59 | >4.65 | >4.65 | >4.65 | >4.65 | >4.65 | |
| R28 | S28 | CuI | 0, 59 | >6.76 | >6.76 | >6.76 | >6.76 | >6.76 | |
| R31 | S33 | CuI | 0, 59 | >4.19 | >4.48 | 4.63 | >4.78 | >4.63 | |
| R32 | S35 | Ag | 60, 0 | 0.05 | | −0.05 | −0.02 | 0.06 | 1.57 |
| R33 | S36 | AgBr | 60, 0 | 0.01 | | −0.11 | −0.01 | 0.15 | 3.67 |
| R34 | S37 | AgI | 60, 0 | 0.01 | | 0.01 | 0.06 | 0.19 | 0.29 |
| R35 | S38 | CuI | 0, 60 | >4.56 | | >4.56 | >4.56 | >4.56 | >4.56 |
| R36 | S39 | CuCl | 0, 60 | 0.05 | | 0.03 | 0.19 | 0.47 | 1.21 |
| R37 | S40 | No AM material | 0, 0 | 0.24 | | 0.2 | | 0.04 | 0.02 |
| R38 | S41 | CuI | 0, 19 | 0.97 | | 2.32 | | >4.59 | 3.58 |
| R39 | S42 | CuI | 0, 15 | 1.50 | | 3.89 | | >5.16 | 4.57 |
| R40 | S43 | CuI | 0, 59 | >5.04 | | >5.19 | | >5.19 | >5.19 |
| R48 | S51 | CuI | 0, 59 | >4.53 | | >4.53 | | >4.53 | >4.53 |
| R49 | S52 | CuI | 0, 59 | 4.38 | | >4.53 | | >4.53 | >4.53 |
| R50 | S53 | CuI | 0, 59 | 3.91 | | 3.84 | | >4.53 | >4.53 |

Results on *P. aeruginosa*, a gram negative bacterium, are shown in Table 5. Result R9 in this table shows that efficacy at much shorter times, i.e., at 15 minutes is surprisingly high. This high efficacy is seen even in those formulations where only CuI is used, such as in R7. All of the above formulations use suspensions with a copper concentration of 59 ppm.

When the copper concentration is dropped to 12 ppm, such as in R11, the efficacy at short times suffers, but one is still able to achieve high efficacy at 24 hrs. Addition of silver as silver metal or silver bromide to copper iodide (compare R11 to R12 or R13; or compare R7 to R8 or R9), does not improve the efficacy, showing that CuI by itself is quite effective.

Further, for *P. aeruginosa*, different polymeric surface modifications were used on CuI, s and some included acids for surface peptization (see results R26, R28 and R31), and all of these show that each of these suspensions were maximally effective. One may also mix different metal halides or metal halide and a metal, and also particles with different surface modifications with high efficacy against *P. aeruginosa* as shown in numerous results in this table.

Results R32 to R36 compare particles of various silver salts (AgBr and AgI), silver metal and various copper salts (CuCl and CuI), all of these surface modified with PVP and by themselves only, and all of them at metal concentration of 60 ppm. This data clearly shows CuI has the highest efficacy and the other materials show lower efficacy against this microbe.

Results R37 through R39 were on porous silica particles. R37 was for silica particles with a size in the range of 0.5 to 3 μm which do not have any CuI Result R38 was for silica particles with a size in the range of 0 to 20 μm which had CuI infused by the method of Example 13 (method 1). The copper metal content in these particles was 1.9% by weight. Result R39 was for silica particles with a size in the range of 0.5 to 3 μm which had CuI infused by the method in Example 14 (method 2). The copper metal content in these particles was 1.5% by weight. These were tested for antimicrobial effect in a suspension, where the silica particles were added with and without CuI. The copper concentration in samples R38 and R39 was 19 and 15 ppm respectively. As expected the sample without antimicrobial additive (result R37) did not show antimicrobial properties. The other two showed a high efficacy.

Results R48 to R50 (on samples S51 to S53 respectively) are the results of suspension testing of particles made by wet grinding in the presence of PVP comprising an aqueous solution using the process described in Example 16. These three samples were obtained from the same run but extracted at different periods of grinding. The average particle size of these three samples was 120, 220 and 920 nm respectively. The last sample, S53 with an average particle size of 920 nm, had a bimodal distribution with particles average sizes peaking at 170 and 1,500 nm. All of these show high antimicrobial efficacy, with the smallest particle size sample (Result R48 on Sample S51) showing a great efficacy at shorter time periods.

Example 19

Efficacy Against *S. aureus* of Various Functionalized Nanoparticles

TABLE 6

| | | | | *S. aureus* | | | | | |
|---|---|---|---|---|---|---|---|---|---|
| Results | Sample | | Conc, PPM, | Time | | | | | |
| # | # | Particles | Ag, Cu | 15 min | 30 min | 1 hr | 2 hr | 6 hr | 24 hr |
| R7 | S12 | CuI | 0, 59 | >4.07 | >4.31 | >4.31 | >4.31 | | |
| R8 | S11 + S12 | Ag + CuI | 10, 59 | >4.31 | >4.31 | >4.31 | >4.31 | | |
| R9 | S10 + S12 | AgBr + CuI | 10, 59 | >4.31 | >4.31 | 4.07 | >4.31 | | |
| R10 | S11 + S12 | Ag + CuI | 10, 6 | 0.05 | 0.04 | 0.06 | 0.09 | | |
| R11 | S12 | CuI | 0, 12 | 0.79 | 0.95 | 1.35 | 1.81 | 2.96 | >4.34 |
| R12 | S11 + S12 | Ag + CuI | 2, 12 | 0.69 | 0.88 | 1.20 | 1.66 | 3.16 | >4.34 |
| R13 | S10 + S12 | AgBr + CuI | 2, 12 | 0.79 | 1.04 | 1.30 | 1.71 | 3.03 | >4.34 |
| R14 | S11 + S12 | Ag + CuI | 10, 59 | 0.58 | 2.71 | >4.34 | >4.34 | >4.34 | >4.34 |
| R28 | S28 | CuI | 0, 59 | >6.47 | >6.47 | >6.05 | >6.47 | >6.47 | >6.47 |

Table 6 shows results from similar experimentation on *S. aureus*, a gram positive bacterium responsible for common staph infections. CuI in small particle size by itself or mixed with silver metal or silver bromide was highly effective as seen in results R7, R8 and R9. Similar conclusion for *S. aureus* as for *P. aeruginosa* can be drawn on concentration of the compounds, mixture of different metal halides or metal halide and a metal, and particles with different surface modifications.

Example 20

Efficacy Against *S. mutans* of Various Functionalized Particles

TABLE 7

| | | | | *S. mutans* | | | | | |
|---|---|---|---|---|---|---|---|---|---|
| Result | Sample | | Conc, PPM, | Time | | | | | |
| # | # | Particles | Ag, Cu | 15 min | 30 min | 1 hr | 2 hr | 6 hr | 24 hr |
| R27 | S27 | CuI | 0, 59 | >4.75 | >4.75 | >4.60 | >4.75 | >4.75 | >4.75 |
| R28 | S28 | CuI | 0, 59 | >4.75 | >4.75 | >4.75 | >4.75 | >4.75 | >4.75 |

To test the broad efficacy of metal halides, and in particular for copper iodide, we also tested functionalized particles of this material against several other microbes. One of these is a strep bacterium *S. mutans*, commonly found in mouth infections. R27 and R28 in Table 7 shows that CuI particles modified with PVP and the copolymer (VP-VA) both resulted in effective reduction of populations of this bacteria.

Example 21

Efficacy Against *S. enterica Typhimurium* of Various Functionalized Nanoparticles

TABLE 8

| | | | | *S. enterica Typhimurium* | | | | | |
|---|---|---|---|---|---|---|---|---|---|
| | | | Conc, PPM, | Time | | | | | |
| Result# | Sample # | Particles | Ag, Cu | 15 min | 30 min | 1 hr | 2 hr | 6 hr | 24 hr |
| R23 | S17 | CuI | 0, 59 | >4.85 | >4.85 | >4.85 | >4.85 | >4.85 | |

Table 8 shows that at 59 ppm, CuI surface modified with PVP showed a high degree of effectiveness (R23) against the microbe *S. enterica* when used alone or in combination with AgBr modified with thiomalic and aspartic acids (R16). This was more effective as compared to AgBr alone with a silver concentration of 10 ppm in the suspension (R15).

Example 22

Efficacy Against *Penicillium* of Various Functionalized Nanoparticles

TABLE 9

| | | | *Penicillium* | | | | |
|---|---|---|---|---|---|---|---|
| Experiment # | Sample # | Particles | Conc, PPM, Ag, Cu | 24 hr | Time 48 hr | 72 hr | 96 hr |
| R27 | S27 | CuI | 0, 59 | >3.98 | >3.98 | >3.98 | >3.98 |
| R28 | S28 | CuI | 0, 59 | >3.98 | >3.98 | >3.98 | >3.98 |

To examine the effectiveness of the inorganic metal salts against molds, experiments were done against *Penicillium* as shown in Table 9. R27 and R28 in this table show that CuI particles modified with PVP and the copolymer (VP-VA) both resulted in effective reduction of this mold.

Example 23

Efficacy Against *A. niger* of Various Functionalized Nanoparticles

Table 10 shows the results for another mold *A. niger*. The strongest response is shown by CuI (R35) by itself.

TABLE 10

| | | | *A. niger* | | | | | |
|---|---|---|---|---|---|---|---|---|
| Result # | Sample # | Particles | Conc, PPM, Ag, Cu | 6 hr | 24 hr | Time 48 hr | 72 hr | 96 hr |
| R33 | S11 | Ag | 50, 0 | −0.09 | −0.01 | 0.01 | 0.00 | −0.16 |
| R34 | S10 | AgBr | 50, 0 | 0.06 | −0.14 | 0.16 | 0.21 | 0.15 |
| R35 | S14 | CuI | 0, 295 | 0.06 | 0.82 | 0.77 | 1.43 | 1.99 |
| R36 | S10 + S14 | AgBr + CuI | 50, 295 | −0.02 | 0.39 | 0.78 | 0.62 | 0.81 |

Example 24

Preparation of Coatings with CuI and their Antimicrobial Testing

Materials and Methods

For this example two sources for CuI were used. The first was bulk copper iodide powder (99.5% Sigma Aldrich) and the second nano-particles of CuI functionalized with PVP prepared from the acetonitrile process and isolated as a dry powder. For the nano-particles two high loadings of CuI in PVP were prepared namely 60 and 50 wt % CuI in PVP. The CuI used was 99.5% from Sigma Aldrich and the PVP was 10,000 MW from Sigma Aldrich. A typical high loading preparation was as follows.

To a liter pear shaped flask fitted with a stir bar was added 4.05 g of CuI powder and 300 ml of anhydrous acetonitrile. This was stirred to give a pale yellow solution. In a separate flask fitted with a stir were added 4.05 g of PVP and 200 ml of anhydrous acetonitrile. This was stirred for 2 hours to give a straw yellow colored solution. While stirring the CuI solution the PVP solution was slowly added to it to give a transparent yellow solution. Upon stirring at room temperature this solution slowly turned a light green color; this took about one hour for completion. This solution was dried under reduced pressure at 30° C. to form a light green powder with a CuI content of 50 wt %. This procedure was repeated except the initial CuI concentration was increased to 6.07 g to give a concentration of CuI in the powder of 60 wt %.

Preparation of Urethane Coating Containing CuI

To a beaker was added 5 g of an aliphatic urethane 71/N aqueous dispersions (35% solids, maximum viscosity 200 cP) sold under the tradename of ESACOTE obtained from Lamberti SpA, (Gallarate, Italy). To this was added 0.118 g of CuI powder (99.5% from Sigma Aldrich, particles not functionalized). This was stirred vigorously and 0.1 g of the cross linking agent PZ28 (Polyfunctional Aziridine manufactured by PolyAziridine, LLC Medford, N.J.) was added to the coating formulation. The urethane coating was applied to stainless steel substrates 2"×2" by brush application and cured at room temperature for 12 hours followed by two hours at 70° C. The cured coating was transparent with a slight brown tint. It was durable and hard with good chemical resistance to both water and ethanol. The $Cu^+$ content of the dried coating was 2.0 wt %. This procedure was repeated except using the nano-powders of CuI described above to give coated surfaces with different concentrations/types of $Cu^+$. These coated substrates were tested for antimicrobial activity against *P. aeruginosa* using a method as described below. As a comparison point a metal coated with DuPont antimicrobial (commercial powder coating) ALESTA™ was also tested (obtained from Dupont, Inc. (Industrial Coatings Division, Wilmington, Del.)). The antimicrobial materials in Alesta™ coatings were zeolite particles (about 2 to 3 μm in size) infused with silver and zinc ions.

Copated test coupons (50×50 mm) were prepared for antimicrobial testing by spraying with 70% ethanol to reduce bacterial background presence. Sample coupons were allowed to air dry before re-spraying with 70% ethanol and allowed to dry completely before testing. Polyethylene (PE) cover slips (40×40 mm) were sterilized via bactericidal UV for 30 minutes per side.

These polymer coated surfaces were tested as discussed earlier using JIS Z2801 2000 (A Japanese Industrial Standard method). The coating compositions and the results are summarized in Table 11.

TABLE 11

| Wt % $Cu^+$ in Coating | Type of CuI used | Particle size* | $Log_{10}$ Reduction (*P. aeruginosa*) 6 hr | 24 hr |
|---|---|---|---|---|
| 2.0 | Bulk Powder (99.5%) | 1 to 2 μm | 0.31 ± 0.03 | 0.29 ± 0.08 |
| 4.3 | CuI nanoparticles (60 wt % in PVP) | 254 nm | >5.69 ± 0.00 | >5.69 ± 0.00 |
| 3.0 | CuI nanoparticles (50 wt % in PVP) | 241 nm | >5.49 ± 0.17 | >5.69 ± 0.00 |
| 0.0 | None | | −0.02 ± 0.10 | −0.02 ± 0.05 |
| DuPont Crystal Clear AM coating | None | 2 to 3 μm | 0.89 ± 0.08 | 4.52 ± 0.00 |

*Particle size of CuI or the antimicrobial material (optical microscope used to characterize bulk powder).

These results show that functionalized CuI particles delivered significantly better antimicrobial performance as compared to the commercial antimicrobial coating, especially at the 6-hour mark. It is notable that the use of CuI (as received) as non-functionalized particles in the coatings when used at about 2 μm in size did not result in any perceived antimicrobial activity (see also Table 12 (next example)), where coatings containing 1% or less $Cu^+$ comprising functionalized nanoparticles were notably antimicrobial).

Example 25

Preparation of Urethane Coatings Containing Wet Ground CuI Dispersion in Urethane (Emulsion) Resin A sample of aliphatic urethane 71/N aqueous dispersion was divided in two parts. In one part CuI was added and ground to a small particle size for a duration of 240 minutes as described in Example 15 so that the smaller CuI particles being formed were functionalized by the PU dispersion. These two parts were then mixed in different proportions to vary the amount of copper in the coating formulation. As an example a formulation where these were mixed in a proportion of 50% each by weight was made as follows. To a beaker was added 3 g of an aliphatic urethane 71/N aqueous dispersion was added 3 g of the CuI comprising dispersion. This was mixed well to form a homogeneous material. While stirring 0.12 g of the cross linking agent PZ28 (polyfunctional aziridine manufactured by PolyAziridine, LLC Medford, N.J.) was added to this mixture. The urethane formulation was applied to stainless steel substrates 2"×2" by brush application and cured at room temperature for 12 hours followed by two hours at 70° C. The cured formulation was transparent with a slight brown tint. It was durable and hard with good chemical resistance to both water and ethanol. The $Cu^+$ content of the dried coating was 3.51 wt %. This procedure was repeated by varying the ratio of PU71/N to CuI urethane dispersion to give coated surfaces with different concentrations of $Cu^+$ as listed in Table 12. These were tested against *P. aeruginosa* as described in the above example, and the results are shown in Table 12. In this example, it should be emphasized that polyurethane 71/N aqueous dispersion is an emulsion of a hydrophobic urethane, as after it is coated and dried, this cannot be solvated in water.

TABLE 12

| Ratio PU:(CuI + PU) (by weight) | Wt % $Cu^+$ in Dried Coating | $Log_{10}$ Reduction 6 hours | 24 hours |
|---|---|---|---|
| 10:90 | 6.33 | >6.08 ± 0.05 | >5.98 ± 0.05 |
| 50:50 | 3.51 | 3.24 ± 0.05 | >5.82 ± 0.05 |
| 75:25 | 1.76 | 3.71 ± 0.05 | >5.76 ± 0.05 |
| 90:10 | 0.70 | 3.24 ± 0.05 | >5.98 ± 0.05 |
| 100:0 | 0.00 | 0.55 ± 0.05 | −0.04 ± 0.08 |

The above results show that incorporation of functionalized CuI particles in coatings which were prepared by grinding in a polymeric emulsion process resulted in polymer-functionalized CuI particles having high antimicrobial activity. The polymeric emulsion functionalized the CuI surfaces and stabilized the particles as it was pulverized. PU coatings without the copper-based additive did not demonstrate antimicrobial properties, as demonstrated in the 100:0 result of Table 12. Further, the antimicrobial activity increased with the increased CuI content (including sample 90:10 which had less than 5% CuI). It is interesting to note that all of these coatings with CuI had better performance at short times as compared to the commercial coating in Table 11.

Example 26

Povidone-iodine Plus Copper Iodide/Polyvinylpyrrolidone Antimicrobial Solution

A copper iodide polyvinylpyrrolidone (PVP) powder is prepared by dissolving 0.0476 g of CuI (99.999% Sigma Aldrich) in 50 ml of anhydrous acetonitrile. To this solution is added 10 g of PVP (10,000 MW Sigma Aldrich) and stirred to form a pale yellow solution. The acetonitrile is removed under reduced pressure at 30° C. to form a pale green powder. This powder contains 0.158 wt % $Cu^+$.

To 10 ml of a 10% solution of Povidone-iodine (CVS brand, obtained from CVS Pharmacy, Tucson, Ariz.) is added 0.38 g of the CuI/PVP powder to give a 60 ppm concentration of $Cu^+$ in the solution. This forms the Povidone—iodine—CuI/PVP antimicrobial solution.

Example 27

Topical Cream Comprising CuI Nanoparticles: Zone of Inhibition

To prepare this cream, functionalized CuI particles with two different sizes were prepared in PVP.

For the first preparation, the particle size was 241 nm and was made by the procedure described in Example 24 which used 10,000 molecular weight PVP from Sigma Aldrich. This is called 50% Powder (as this had 50% by weight of CuI in the dry powder).

For the second preparation, the particle size was predominantly 4 nm and was prepared in the following fashion. To a reaction flask containing 80 ml of anhydrous acetonitrile, (99.8% Sigma Aldrich Cat. #271004), was added 4.75 g of PVP (Luvitec™ K17 from BASF) and stirred to form a light yellow solution. To this solution was added 0.25 g of CuI (99.999% Sigma Aldrich Cat. #205540) and after stirring for 30 minutes this resulted in a clear pale green solution. Then the bulk of the acetonitrile was removed under reduced pressure at 30° C. to form a viscous paste. The temperature was then increased to 60° C. to completely remove the solvent to give a pale yellow solid. Dynamic light scattering on a dilute sample of the dispersion showed a mean particle size of 4 nm for 85% of the particulate volume, and the others were larger. This had 5 weight % of CuI in the dry powder, and was called 5% Powder.

The cream was prepared in a beaker by adding 0.06 g of Carbomer (obtained from Lubrizol Inc, Wickliffe, Ohio) and 2.0 ml of deionized water (18 Mohm-cm). This was mixed to give a slightly hazy non colorless liquid. To this mixture was added 0.2 g of PVP (Sigma Aldrich, 10,000 molecular weight) and the mixture stirred vigorously. The addition of PVP caused a slight decrease in the viscosity. To this solution was added while stirring 1.96 g of CuI/PVP 50% Powder followed by 1.45 g of CuI/PVP 5% Powder. The final concentration of $Cu^+$ in the cream was 2.1 wt %. This cream was tested against P. aeruginosa and S. aureus using the zone of inhibition method as described below.

Petri dishes for the test were prepared by dispensing 25 ml of sterile agar medium into sterile plates. Overnight cultures were diluted to final working optical density 600 nm of 0.100 and uniformly streaked over the agar using sterile swabs. Cylindrical plugs having a diameter of approximately 5.3 mm were removed from the solidified agar plates by means of a sterile cork borer. Approximately 75 µl of cream were added to the wells. Triple antibiotic first aid ointment from Walgreens Pharmacy (Walgreens Brand, obtained from Walgreens Pharmacy, Tucson, Ariz.) was used as a control material. This cream (control) listed Bacitracin zinc 400 units, Neomycin 3.5 mg and Polymyxin B sulfate at 5,000 units as active ingredients in white petrolatum. Plates as described were incubated in a humidified chamber at 37° C. for 24 hours at which time the plates were examined for bactericidal and growth inhibition effects.

Upon examination of the plates a slight bluish-green hue halo was observed around the wells along with a zone of inhibition for CuI comprising creams. A three scale measure was used to determine the zone of inhibition, "0" for no inhibition, which was indicated by complete absence of the zone of inhibition; "1" as limited inhibition, where the zone diameter (including the well) was in the range of 6 to 8 mm; and significant inhibition designated as "2", when this zone (including the well) exceeded 8 mm. The results are shown in Table 13 below.

TABLE 13

| Material | Inhibition against P. aeruginosa | Inhibition against S. aureus |
|---|---|---|
| Control | 0 | 2 |
| Cream with CuI | 2 | 2 |

The control cream is known to be effective against Gram positive microorganisms, and the results show the controls inhibited S. aureus, as expected. Both of the CuI containing creams show equivalent effectiveness in this test against S. aureus. Against the Gram negative P. aeruginosa, the control creams were not expected to show efficacy, and they did not. However, the CuI-based cream did show substantial effectiveness, further bolstering the broad antimicrobial nature of the invention.

Example 28

Preparation of CuI Particles Surface Modified by Sodiumdodecylsulfate (SDS) by Grinding Process CuI (99.5% from Aldrich) and SDS (Aldrich#436143) were used for this preparation. The same mill that was used in Example 15 was used to prepare this sample. The mill parameters were: 4200 RPM, Pump=600 RPM, Media used=100 µm diameter YTZ (Yttrium Stabilized Zirconia), Grinding time=1260 min Water was allowed to circulate with pump on at 25 rpm and the mill on at 1000 rpm while 94.2854 g CuI (99.5%), and 17.142 g SDS were added (85.7% CuI and 14.3% SDS). This was done to prevent overloading or clogging the mill. The pump and mill speed were then increased to 600 and 4200 respectively. This mixture was ground at these speeds for 1260 minutes using 4.13 kWh. A chiller was used to cool the slurry being ground. A pink mixture was removed from the mill and dried in a blowing furnace because the foaming action of SDS prevents drying on a rotary evaporator. The product was dried in a covered pan at 70° C. until the product was completely dry. This formed a pink/tan solid powder with a yield of 107 g (97.3% yield). Table 14 shows the particle size from dynamic light scattering measurements when this powder was redispersed in water. This table also shows the antimicrobial properties of the liquid suspension when tested at a copper concentration of 59 ppm. The particle size here is relatively large, which may have reduced its efficacy at shorter times as compared to the results in Tables 5 and 6.

TABLE 14

| Particle size (DSL) | | Antimicrobial activity (59.07 ppm Cu), | | |
|---|---|---|---|---|
| Particle Size (nm) | % polydispersity | Time | $\log_{10}$ reduction | |
| | | | P. aeruginosa | S. aureus |
| 372.2 | 59.4 | 15 min | 3.60 ± 0.21 | 1.53 ± 0.08 |
| | | 1 hr | 3.97 ± 0.30 | 3.57 ± 0.04 |
| | | 3 hr | >4.66 ± 0.00 | >4.50 ± 0.00 |
| | | 6 hr | >4.66 ± 0.00 | >4.50 ± 0.00 |

Example 29

Preparation of Precipitated Porous Silica Infused with CuI (a) Copper iodide (2 g, 99.5%, Aldrich) was added to a 250 ml round bottom flask along with a stir bar and acetonitrile (40 ml) to give a saturated solution. This saturated solution was then left to stir at room temperature for several hours. The resulting solution was a pale yellow color with a pale yellow precipitate.

(b) This CuI saturated solution was filtered via vacuum filtration using a 0.8 μm MAGNA, nylon, supported plain filter paper by Osmonics.

(c) The clear, pale yellow filtered solution was added to a clean 250 ml round bottom flask with a stir bar and 3.5 g of porous silica (Sipernat 22 LS, 9 μm in size, precipitated Silica with a specific surface area of 180 $m^2$/g, obtained from Evonik Industries). This solution was stirred at 25° C. for one hour.

(d) The solution was again filtered via vacuum filtration using a 0.8 μm MAGNA, nylon, supported plain filter paper by Osmonics (Obtained from Fisher Scientific, Pittsburgh, Pa.). A white silica and CuI containing powder was collected and was left to dry overnight at 100° C.

(e) Copper iodide (2 g, 99.5%) was added to a 250 ml round bottom flask along with a stir bar and acetonitrile (40 ml) to give a saturated solution. This saturated solution was then left to stir at room temperature for several hours. The resulting solution was a pale yellow color with a pale yellow precipitate.

(f) This CuI saturated solution was filtered via vacuum filtration using a 0.8 μm MAGNA, nylon, supported plain filter paper by Osmonics.

(g) The clear, pale yellow filtered solution was added to a clean 250 ml round bottom flask with a stir bar and 3.5 g of porous silica+CuI which was prepared in step "d". This solution was stirred at 25° C. for one hour.

The solution was again filtered via vacuum filtration using a 0.8 μm MAGNA, nylon, supported plain filter paper by Osmonics. A white powder was collected and was left to dry overnight at 100° C. An analysis showed that this powder was 76.6% silica and 23.4% CuI. Its antimicrobial properties in a suspension at 59 ppm of Cu is shown in table 15, and it is likely that the availability of Cu+ ions from antimicrobial particles in porous particles is lower than from the assembly of individual nanoparticles, which leads to lower efficacy as compared to the results in Table 5

TABLE 15

| Antimicrobial activity (59.07 ppm Cu), $\log_{10}$ reduction | |
|---|---|
| Time | P. aeruginosa |
| 30 min | 3.23 ± 0.62 |
| 3 hrs | 2.96 ± 0.35 |

Example 30

Preparation and Testing of Antimicrobial Powder Coatings

The coatings were prepared by first dry blending the functionalized CuI particles (SDS functionalized particles as prepared in Example 28, or porous silica infused with CuI as prepared in Example 29) with a carboxylated polyester resin (Crylcoat 2471 obtained from Cytec, Woodland Park, N.J.) containing a crosslinking agent triglycidylisocyanurate (TGIC, obtained from Aal Chem, Grand rapids, MI), a flow/leveling agent Powdermate 570 (obtained from Troy Chemical, Newark, N.J.) and a degasser Powdermate 542 (obtained from Troy Chemical). The concentration of CuI was varied. This mixture was then extruded in a two zone temperature process (zone 1=109° C. and zone 2=86° C.) and roller cooled to form a ribbon. This ribbon was crushed and dry blended to form a fine powder. This powder was ultrasonically fed into a Corona gun for powder coating onto 2"×2"×0.025" aluminum coupons. The coated aluminum substrates were cured at 204° C. for ten minutes under ambient atmosphere. The various coatings had a thickness ranging from about 60 to 75 μm and had a gloss (at 60°) between 100.3 to 126.3). The antimicrobial results are shown in Table 16. These coatings are compared with coatings deposited from a commercial antimicrobial powder material Alesta PFC609S9A from Dupont (Experimental Station, Del.) which was also deposited in a similar fashion as above on similar substrates. These coatings have silver and zinc ions to provide antimicrobial properties. All of these coatings with antimicrobial material (including the one from Dupont) resulted in antimicrobial surfaces. However, at shorter times, all of the coatings with CuI provided superior efficacy as seen by greater log reduction.

TABLE 16

| | $\log_{10}$ reduction of the microbe | | | |
|---|---|---|---|---|
| Sample | P. aeruginosa (6 Hrs) | P. aeruginosa (24 Hrs) | S. aureus (6 hrs) | S. aureus (24 hrs) |
| 0.25% Cu (with SDS) | >5.63 | >5.43 | >4.77 | >5.31 |
| 1.0% Cu (with SDS) | >5.63 | >5.83 | >5.72 | >5.31 |
| 3.0% Cu (with SDS) | >5.63 | >6.03 | >5.72 | >5.31 |
| 0.25% Cu (in Silica) | >5.53 | 4.34 | 5.23 | >5.31 |
| DuPont AM coating | 1.79 | 5.73 | 3.29 | 4.65 |
| Standard polyester resin (No AM) | −0.19 | −0.59 | 0.16 | 0.57 |

The samples were cleaned after the evaluation by rinsing them twice in ethanol, washing them with a dish washing liquid and followed by another two rinses in ethanol. The antimicrobial effectiveness of the samples was evaluated against S. aureus. The results are shown in Table 17 and demonstrate that the samples are durable to washing and repeated use.

TABLE 17

| | $\log_{10}$ reduction of the microbe | |
|---|---|---|
| Sample | S. aureus (6 hrs) | S. aureus (24 hrs) |
| 0.25% Cu (with SDS) | 4.58 | >4.65 |
| 1.0% Cu (with SDS) | >5.35 | >4.75 |
| 3.0% Cu (with SDS) | >5.35 | >4.65 |
| 0.25% Cu (in Silica) | 4.23 | >4.31 |
| Standard polyester resin (No AM) | −0.09 | 0.53 |

Another set of ground CuI/SLS was made where the proportion was 75/25 by weight. The grinding parameters were the same as in Example 28, but the grinding time was reduced to 300 minutes. This was added to the powder coatings as discussed above in a concentration of 0.25 and 0.05% Cu (as CuI). The coatings with 0.25% Cu had a slight haze, whereas coatings with 0.05% Cu were clear. The results on the 0.25% coatings are shown in Table 18.

TABLE 18

| Sample Traetment | Log$_{10}$ reduction of the microbe (S. aureus, ATCC#25923), 24 hours | | | |
|---|---|---|---|---|
| | Initial | Washed 1X | Washed 50 times | Washed 50 times and scratched |
| Washed with water | >4.21 | >4.31 | >4.31 | >4.31 |
| Washed with Windex ® | >4.21 | >4.31 | >4.31 | >3.91 |
| Washed with Pine-sol ® | >4.21 | >4.31 | >4.31 | >4.31 |
| Ultrasonicated in water for 5 minutes @ 20 KHz | >6.01 | >6.01 | | |

Pine-Sol® and Windex® are commercial cleaners made by Chlorox (Oakland, Calif.) and by S. C. Johnson (Racine, Wis.) respectively. Each wash cycle with cleaners comprised spraying of cleaner and then covering the surface with a wipe by going in a zig-zag motion horizontally, vertically and then horizontally. The surfaces were scratched with heavy duty scour pads, Target Brand, Obtained from a Target store in Tucson, Ariz.

The results on coatings with 0.05% Cu are shown below in Table 19.

TABLE 19

| | Log$_{10}$ reduction of the microbe | | | |
|---|---|---|---|---|
| | S. Aureus (ATCC25923) | | P. Aeruginosa (ATCC 9027) | |
| Sample Type | 6 hrs | 24 hrs | 6 hrs | 24 hrs |
| Coating without antimicrobial additive | 0.9 | 1.37 | 0.39 | 0.01 |
| Coating with antimicrobial additive | >3.59 | >4.17 | >3.86 | >3.61 |
| Dupont AM coating | 1.82 | >4.17 | 2.27 | >4.16 |

The results (Log$_{10}$ Reduction) on coatings with 0.05% Cu and 0.25% Cu against *salmonella* (*S. typimurium*, ATCC#23564) are compared to coatings without antimicrobial (AM) agent in Table 20.

TABLE 20

| Time | Coating without AM | Coating with 0.05% Cu | Coating with 0.25% Cu |
|---|---|---|---|
| 6 hours | 0.06 ± 0.08 | 1.78 ± 0.25 | >4.59 ± 0.28 |
| 24 hours | 0.11 ± 0.03 | 2.64 ± 1.10 | >4.54 ± 0.35 |

Example 31

Formation of Functionalized Particles by Wet Grinding

The samples were ground in a wet grinding mill Minicer® as described in Example 15. The grinding beads were made of YTZ ceramic. The materials used for these preparations are outlined in Table 21.

TABLE 21

| Material | Description |
|---|---|
| Material | Description |
| AuI | Gold iodide, Aldrich 398411 |
| AgI | Silver iodide, 204404 |
| Bioterge | Sodium capryl sulfonate (aq); BIOTERGE PAS-8S (obtained from Stepan, Northfield, IL) |
| Chitosan | Deacetylated chitin, medium molecular weight, Aldrich 448877 |
| CuI | Copper iodide 99.5% Aldrich 03140 |
| CuSCN | Copper thiocyanate, Aldrich 298212 |
| PEG | Polyethylene glycol CARBOWAX ™ SENTRY ™ PEG 8000 NF, FCC Grade; Macrogol 8000 Ph. Eur. Granular, (obtained from Dow Chemical, Midland, MI) |
| PVP-A | Polyvinylpyrrolidone Avg MW = 10,000, Aldrich PVP10 |
| PVP-B | Polyvinylpyrrolidone Avg MW = 10,000, Luvitex K17 57858045 (Obtained from BASF, Germany) |
| SDS | Sodium dodecyl sulfate, Aldrich 436143 |
| ZnO | Zinc oxide, Aldrich 251607 |
| H2O | Deionized water, 18 megaohm-cm |
| Ascorbic Acid | L-Ascorbic acid >99%, Aldrich 95210 |
| UV stabilizer | 2-Hydroxy-4-(octyloxy)benzophenone 98%, Aldrich 413151 |
| IPA | Isopropyl alcohol, 99.5% Aldrich 278475 |

Table 22 shows various samples which were processed along with the conditions under which these were made. During grinding operation, the grinding head was chilled using a coolant at 5° C. However, depending on the viscosity, volume of material being ground and grinding conditions the grinding liquid temperature varied between 10 and 30° C. The quantity of grinding beads was measured volumetrically as approximately 140 ml.

TABLE 22

| Sample | Solids Proportion by Weight % | | Total Solids (g) | Water (mL) | Mill (RPM) | Pump (RPM) | Media Size (mm) | Grinding Time (min) |
|---|---|---|---|---|---|---|---|---|
| | Metal Compound, % | Functionalization agent(s), % | | | | | | |
| 1. CuI/PEG | CuI, 15 | PEG, 85 | 10 | 100 | 4200 | 600 | 0.1 | 960 |
| 2. CuI/PEG/SDS | CuI, 20 | PEG, 77.61; SDS, 2.39 | 10 | 100 | 4200 | 600 | 0.1 | 60 |
| 3. CuI/PVP | CuI, 0.47 | PVP-B, 99.53 | 60.29 | 300 | 3800 | 500 | 0.1 | 360 |
| 4. CuI/PVP | CuI, 10 | PVP-B, 90 | 10 | 100 | 4200 | 600 | 0.1 | 60 |
| 5. CuI/PVP/SDS | CuI, 20 | PVP-A, 77.61; SDS, 2.39 | 10 | 100 | 4200 | 600 | 0.1 | 300 |
| 6. CuI/SDS | CuI, 85.7 | SDS, 14.3 | 0.7 | 140 | 2500 | 350 | 0.3 | 420 |
| 7. CuSCN | CuSCN, 10 | PVP-A, 90 | 1 | 100 | 4200 | 600 | 0.1 | 172 |

TABLE 22-continued

| Sample | Solids Proportion by Weight % | | Total Solids (g) | Water (mL) | Mill (RPM) | Pump (RPM) | Media Size (mm) | Grinding Time (min) |
|---|---|---|---|---|---|---|---|---|
| | Metal Compound, % | Functionalization agent(s), % | | | | | | |
| 8. AuI | AuI, 0.21 | PVP-A, 99.79 | 5.01 | 100 | 4200 | 600 | 0.1 | 120 |
| 9. AgI | AgI, 10 | PVP-A, 90 | 10 | 100 | 4200 | 600 | 0.1 | 1070 |
| 10. ZnO | ZnO, 10 | PVP-B, 90 | 10 | 100 | 4200 | 600 | 0.1 | 60 |
| 11. CuI/CH (Chitosan) | CuI, 50 | Chitosan, 50 | 2 | 100 mL + 2 g acetic acid | 4200 | 600 | 0.1 | 60 |
| 12. CuI/CH/PVP | CuI, 10 | Chitosan, 10; PVP-B, 80 | 10 | 100 mL + 1.5 g acetic acid | 4200 | 600 | 0.1 | 60 |
| 13. CuI/PEG/ Bioterge | CuI, 85.7 | Bioterge, 4.3; PEG, 10 | 3 | 200 | 4200 | 600 | 0.1 | 30 |
| 14. CuI/Ascorbic acid | CuI, 85.7 | Ascorbic acid, 14.3 | 0.7 | 200 | 4200 | 600 | 0.1 | 30 |
| 15. CuI/UV Stabilizer | CuI, 20 | UV Stabilizer, 80 | 2.5 | 10 mL + 190 mL IPA | 4000 | 600 | 0.1 | 1000 |
| 16. AgBr/PVP | AgBr, 10 | PVP-B, 90 | 10 | 100 | 4000 | 600 | 0.1 | 60 |

Table 23 shows the results of average particle size. Tables 24 and 25 show antimicrobial activity of select samples against *P. aeruginosa* and *S. aureus* respectively. Some of these formulations were made to verify the viability of grinding different materials with different functionalizing agents and to see if these will result in particle sizes with good antimicrobial activity. Under the specific processing conditions utilized for that sample, sometimes a bimodal or a trimodal particle size distribution was seen (measured by light scattering). In those cases where most of the mass was represented by a single fraction, other fractions are not shown. Unless stated otherwise, the antimicrobial properties were typically measured at 59 ppm of metal concentration (concentration in the testing solution). The concentrations of the functionalization agents in the testing solutions are also shown in Tables 24 and 25.

By varying the conditions of grinding and the formulation composition it was possible to vary the average particle size from about 3 to about 1,000 nm. It was also possible to obtain larger particle sizes, but attention was focused on obtaining particles smaller than about 200 nm. In general long grinding times and small, concentration of the material being ground favored the formation of smaller particles (e.g., see sample#3). It was also found, however, that it was possible to achieve attractive antimicrobial properties with modest grinding times (e.g., see samples 2, 4 and 11 to 14). It is also possible to introduce large fractions of CuI (greater than 10%) relative to the functionalizing agents, e.g., in samples 6, 13 and 14 the amount exceeds 80%. This stands in contrast to most chemical syntheses of CuI (see Examples 7 to 9) where the percentage of CuI to the surface functionalizing agent does not exceed 5% and is typically notably smaller than 5%

When such high concentration of functionalizing materials are used as in the chemical synthesis route, then the addition of the functionalized antimicrobial material to a matrix material involves the introduction of a large amount of functionalizing material, This can often impact negatively the properties of the end-products produced, particularly for solid products.

It has also been demonstrated that it is possible to grind and functionalize other metal salts including metal halides, and metal oxides, e.g. CuSCN, AuI, AgI, ZnO and AgBr samples 7, 8, 9, 10 and 16 respectively. Sample 15 shows preparation of CuI functionalized with a UV stabilizer.

TABLE 23

Particle Size

| Sample | Solids Proportion by Weight % | | Particle Size* by Mass % |
|---|---|---|---|
| | Metal Compound, % | Functionalization agent(s), % | |
| 1. CuI/PEG | CuI, 15 | PEG, 85 | 95% is 10 nm |
| 2. CuI/PEG/SDS | CuI, 20 | PEG, 77.61; SDS, 2.39 | 83% is 26 nm, 17% is 140 nm |
| 3. CuI/PVP | CuI, 0.47 | PVP-B, 99.53 | 93% is 3 nm, 5% is 17 nm |
| 4. CuI/PVP | CuI, 10 | PVP-B, 90 | 65% is 10 nm, 35% is 120 nm |
| 5. CuI/PVP/SDS | CuI, 20 | PVP-A, 77.61; SDS, 2.39 | 89% is 6 nm, 11% is 117 nm |
| 6. CuI/SDS | CuI, 85.7 | SDS, 14.3 | 75% is 20 nm, 25% is 120 |
| 7. CuSCN | CuSCN, 10 | PVP-A, 90 | 75% is 180 nm, 25% is 50 nm |
| 8. AuI | AuI, 0.21 | PVP-A, 99.79 | 99% is 4 nm |
| 9. AgI | AgI, 10 | PVP-A, 90 | 99% is 3 nm |
| 10. ZnO | ZnO, 10 | PVP-B, 90 | 93% is 120 nm |

TABLE 23-continued

Particle Size

| | Solids Proportion by Weight % | | |
|---|---|---|---|
| Sample | Metal Compound, % | Functionalization agent(s), % | Particle Size* by Mass % |
| 11. CuI/CH (Chitosan) | CuI, 50 | Chitosan, 50 | 22% is 14 nm, 78% is 1371 nm |
| 12. CuI/CH/PVP | CuI, 10 | Chitosan, 10; PVP-B, 80 | 81% is 9 nm, 19% is 808 nm |
| 13. CuI/PEG/Bioterge | CuI, 85.7 | Bioterge, 4.3; PEG, 10 | 82% is 30 nm, 18% is 150 |
| 14. CuI/Ascorbic acid | CuI, 85.7 | Ascorbic acid, 14.3 | N/A |
| 15. CuI/UV Stabilizer | CuI, 85.7 | UV Stabilizer, 14.3 | 100% is 410 nm |
| 16. AgBr/PVP | AgBr, 10 | PVP-B, 90 | 96% 744 nm, 4% 165 nm |

Some of the dry powders (after grinding was over and the particles were dried in a roto-evaporator) were examined under an optical microscope. The particles of the dried cluster were found to be in the range of 570 nm to 2 microns for sample 6 and for sample 13 it was in the range of about 1 to 2 microns. This shows clusters of particles are formed upon drying, particularly when a polymeric agent (PEG in this case) is present.

TABLE 24 antimicrobial test results against *P. aeruginosa*

| | Metal, | Functionalization | $Log_{10}$ reduction of *P. aeruginosa* after given time | | | | | |
|---|---|---|---|---|---|---|---|---|
| Sample | (ppm) | agent(s) (ppm) | 5 min | 15 min | 30 min | 1 hr | 3 hr | 6 hr |
| 1. CuI/PEG | | | | | Not tested | | | |
| 2. CuI/PEG/SDS | Cu, (59) | PEG, (688); SDS (21) | | | >4.77 ± 0.00 | | >4.77 ± 0.00 | |
| 3. CuI/PVP | Cu, (59) | PVP-B, (37527) | | 4.33 ± 0.34 | | 4.57 ± 0.00 | >4.42 ± 0.21 | >4.57 ± 0.00 |
| 4. CuI/PVP | Cu, (59.) | PVP-B, (1595) | | >4.64 ± 0.00 | | >4.64 ± 0.00 | >4.64 ± 0.00 | |
| 5. CuI/PVP/SDS | Cu, (59) | PVP-A, (688); SDS (1) | | | 4.59 ± 0.00 | | >4.60 ± 0.00 | |
| 6. CuI/SDS | Cu, (59) | SDS, (30) | | 3.60 ± 0.21 | | 3.97 ± 0.30 | >4.66 ± 0.00 | >4.66 ± 0.00 |
| 7. CuSCN | Cu, (59.) | PVP-A, (1015) | | 0.51 ± 0.04 | | 3.95 ± 0.21 | 4.88 ± 0.00 | |
| 8. AuI | Au, (59) | PVP-A, 46034 | | | >5.07 ± 0.00 | | >5.07 ± 0.00 | |
| 9. AgI | Ag, (10) | PVP-A, (196) | | 0.10 ± 0.09 | | -0.07 ± 0.15 | 0.19 ± 0.21 | |
| | Ag, (59) | PVP-A, (1159) | | | | | | |
| | Ag, (200) | PVP-A, (3924) | | | | | | |
| 10. ZnO | | | | | Not tested | | | |
| 11. CuI/CH (Chitosan) | Cu, (59) | Chitosan, (177) | 1.36 ± 0.11 | >4.60 ± 0.00 | | >4.60 ± 0.00 | | |
| 12. CuI/CH/PVP | Cu, (59) | Chitosan, (177); PVP-B, (1418) | 1.63 ± 0.04 | >4.60 ± 0.00 | | >4.60 ± 0.00 | | |
| 13. CuI/PEG/Bioterge | Cu, (59) | Bioterge, (9); PEG, (21) | | | | | | |
| 14. CuI/Ascorbic acid | Cu, 59.07 | Ascorbic acid, (30) | | | | | | |

TABLE 25 antimicrobial test results against *S. aureus*

| | Metal, | Functionalization | $Log_{10}$ reduction of *S. aureus* after given time | | | | | |
|---|---|---|---|---|---|---|---|---|
| Sample | (ppm) | agent(s) (ppm) | 5 min | 15 min | 30 min | 1 hr | 3 hr | 6 hr |
| 1. CuI/PEG | | | | | Not Tested | | | |
| 2. CuI/PEG/SDS | Cu, (59) | PEG, (688); SDS (21) | | | 3.97 ± 0.00 | | >4.27 ± 0.00 | |
| 3. CuI/PVP | Cu, (59) | PVP-B, (37527) | | | | | | |

TABLE 25-continued antimicrobial test results against S. aureus

| Sample | Metal, (ppm) | Functionalization agent(s) (ppm) | Log$_{10}$ reduction of S. aureus after given time | | | | | |
|---|---|---|---|---|---|---|---|---|
| | | | 5 min | 15 min | 30 min | 1 hr | 3 hr | 6 hr |
| 4. CuI/PVP | Cu, (59) | PVP-B, (1595) | | 2.36 ± 0.06 | | >4.38 ± 0.00 | >4.38 ± 0.00 | |
| 5. CuI/PVP/SDS | Cu, (59) | PVP-A, (688); SDS (21) | | | | | | |
| 6. CuI/SDS | Cu, (59) | SDS, (30) | | 1.53 ± 0.08 | | 3.57 ± 0.04 | >4.50 ± 0.00 | >4.50 ± 0.00 |
| 7. CuSCN | Cu, (59) | PVP-A, (1015) | | 0.27 ± 0.06 | | 0.56 ± 0.01 | 2.83 ± 0.07 | |
| 8. AuI | Au, (59) | PVP-A, (46034) | | 0 | | | | |
| 9. AgI | Ag, (10) | PVP-A, (196) | | 0.08 ± 0.05 | | 0.01 ± 0.00 | 0.14 ± 0.00 | |
| | Ag, (59) | PVP-A, (1159) | | | 0.59 ± 0.02 | | 3.94 ± 0.10 | |
| | Ag, (200) | PVP-A, (3924) | | | >4.71 ± 0.00 | | >4.71 ± 0.00 | |
| 10. ZnO | | | | Not tested | | | | |
| 11. CuI/CH (Chitosan) | Cu, (59) | Chitosan, (177) | | | | | | |
| 12. CuI/CH/PVP | Cu, (59) | Chitosan, (177); PVP-B, 1418 | | | | | | |
| 13. CuI/PEG/Bioterge | Cu, (59) | Bioterge, (9); PEG, (21) | 0.019 ± 0.06 | 1.68 ± 0.07 | | >4.53 ± 0.00 | | |
| 14. CuI/Ascorbic acid | Cu, (59.07) | Ascorbic acid, (30) | >4.60 ± 0.00 | >4.60 ± 0.00 | | >4.60 ± 0.00 | | |

The antimicrobial properties of the samples in Tables 22 and 23 are shown in Tables 24 and 25. Table 24 shows the antimicrobial properties when tested against *P. aeruginosa* and Table 25 shows the antimicrobial properties against *S. aureus*. Some materials were tested for both microbes and several were only tested for one of them. Good antimicrobial properties were obtained with the AuI suspensions. However, such suspensions were black in color and for those objects where color is an issue; this material will not meet the product requirements. The tests for AgI were carried out at 10, 59 and 200 ppm Ag and for CuI at 59 ppm Cu. These results on *S. aureus* in Table 25 show that AgI was quite ineffective at 10 and 59 ppm Ag, whereas it showed good antimicrobial property at 200 ppm. This shows that copper iodide is a more effective antimicrobial material as compared to silver iodide at lower concentrations (see several results on CuI at 59 ppm) in this table and also results presented previously (e.g., Tables 5 and 6).

It was also found that CuI exhibited greater antimicrobial effectiveness at short times (e.g., 15 minutes) than CuSCN (compare sample 3 vs sample 7 in Table 24), although CuSCN exhibited attractive antimicrobial properties at longer times. Chitosan is not soluble in water, but it is soluble in water when a small amount of acetic acid was added, and hence could be used as a functionalization agent in aqueous media. Chitson functionalized CuI (sample 11) exhibited high antimicrobial effectiveness in times as short as 15 minutes. CuI functionalized with ascorbic acid exhibited outstanding antimicrobial effectiveness in times as short as after 5 minutes (see sample 14 in Table 25). In several cases more than one functionalization agent was used, e.g., samples 2, 5, 12 and 13. All of these produced attractive antimicrobial effectiveness.

Although the copper concentration (as copper salt) in most formulations was 59 ppm, changes in the copper concentration would lead to changes in antimicrobial effectiveness. For example, increasing the copper concentration would produce increased antimicrobial effectiveness at a given time and comparable antimicrobial effectiveness at shorter times.

Example 32

Antimicrobial Activity Against *Trichophyton mentagrophytes* Fungus

*T. mentagrophytes* is a common nail fungus. To test the efficacy of the AM material, CuI nanoparticles functionalized with PVP were made following Example 24. The proportions of the materials used were different. 300 ml of acetonitrile, 60 g of PVP along with 0.2856 of CuI was used. The particle size of the functionalized particles was 6 nm. The log$_{10}$ reduction in the fungus using a liquid suspension with Cu concentration at 59 ppm (present as CuI) is shown in Table 26.

TABLE 26

| Time, hrs | Log$_{10}$ reduction |
|---|---|
| 6 | 1.5 |
| 24 | 2.93 |
| 48 | 2.99 |

Example 33

Wound Dressing Preparation and Antimicrobial Testing (a) Solution for Preparation of Wound Dressings without Antimicrobial Material A solution was made with (a) 1.62 g sodium carboxymethyl cellulose (molecular weight (Mw) 700,000 obtained from Sigma Aldrich, Cat#419338) and (b) 80 g DI-H2O. This solution was stirred while heating at 70° C. to give a clear, viscous, colorless solution.

(b) Solution for Preparation of Wound Dressings with Functionalized CuI Particles (Resulted in 1 wt % Cu (as CuI) in Dry Solid)

A solution was made with (a) 0.0590 g CuI/PEG/Bioterge Powder (28.57% Cu (as CuI) in powder), prepared as Sample 13 in Example 31 except that the grinding time was 13 minutes instead of 30 minutes (the average CuI particle size was about 320 nm with polydispersity being 168%), (b) 80 g DI-H2O. This solution was stirred at room temperature and sonicated to give an opaque, white solution. At the end of this process, 1.62 g sodium carboxymethyl cellulose (molecular weight (Mw) 700,000). This solution was stirred while heating at 70° C. to give an opaque, viscous, slightly green solution.

(c) Preparation of Wound Dressing

One ply, white Kimtech Pure CL5 #06179, 50% rayon/ 50% polyester cleanroom wipes from Kimberly Clark Professional (Roswell, Ga.) were cut into 2"×2" pieces to use as gauze pieces for coating the above solutions for testing of wound dressings. The 2"×2" gauze pieces were first weighed before coating. They were then placed on a piece of glass and were pre-wetted by hand with 0.9 ml DI-H2O using a syringe. Solutions used for the wound dressing application were prepared as given below and 1 ml volume of one of these solutions was then evenly applied to the pre-wetted wipe by hand using a syringe.

The coated gauze pieces were then dried in the oven for 30-40 minutes at 70° C. Once dried the gauze pieces were removed from the glass and were weighed again to determine the total solids content. Applying 1 ml of the coating solutions to the gauze gave an average solid content of 0.02 g. Wipes were also prepared with solids content higher than 0.02 g, including single and multiple coating applications. After coating, the standard gauze pieces (no antimicrobial) were white in color and the copper containing gauze pieces were a pale green color. These coated gauze pieces were then tested against *P. aeruginosa* as follows.

(d) Testing of Dressings Against *P. aeruginosa*

A single colony of *P. aeruginosa* was cultured overnight to stationary phase in tryptic soy broth (TSB). The following day, the culture was diluted in TSB to read .1 optical density in a Synergy 2 reader (from Biotek Instruments Inc, Winooski, Vt). Following this, 0.25 ml of culture was plated onto petri dishes containing tryptic soy agar (TSA). Gauze samples were then placed onto individual plates, one sample per plate. The total solid content on each gauze piece averages 0.02 g, with the copper content (in the form of CuI) being 1% of this mass. Each section was pressed firmly onto the agar on the plate to ensure homogeneous surface contact. The bacteria in contact with the gauze were allowed to grow for 72, and 96 hours, one plate per time-point. After each time-point the respective gauze sample was removed and the newly exposed area was swabbed with a sterile loop, which in turn was spread over a clean agar plate. This was allowed to grow for 24 hrs, after which visual inspection of the plate produces the following observations: 72 hrs Cu-gauze completely killed the bacteria originally plated under it, while the standard gauze displayed a heavy bacterial growth. The 96 hour gauze assay produced results identical to the 72 hr testing.

Example 34

Comparison of PU Coatings Made by Grinding CuI in Emulsion, Vs, Grinding CuI with SDS and then Adding these to the Emulsion In this preparation, CuI was ground with SDS (see Example 28). The composition after grinding was dried and then added to the polyurethane emulsion described in Example 24. In this example the CuI was not ground with the emulsion, but particles functionalized (pre-functionalized) with the surfactant were added and mechanically mixed into the PU emulsion. These were then coated on 5 cm×5 cm stainless steel coupons and evaluated for antimicrobial efficacy with and without CuI additive. The samples with CuI had a copper concentration of 1% in the dry coating. The results in Table 27 show that these samples were antimicrobial. These samples can be compared to coatings prepared by grinding CuI in PU emulsion, where this data is shown in Table 28. Samples produced by both methods exhibited very attractive antimicrobial properties.

TABLE 27

Pre-functionalized CuI particles added to PU coating emulsion

| Time | $Log_{10}$ Reduction *P. aeurginosa* | | $Log_{10}$ Reduction *S. aureus* | |
| --- | --- | --- | --- | --- |
| | With CuI | Without CuI | With CuI | Without CuI |
| 24 hr | 4.05 | −0.49 | >4.47 | 0.21 |

TABLE 28

Functionalized particles formed by grinding CuI in PU coating emulsion

| Time | $Log_{10}$ Reduction *P. aeurginosa* | | $Log_{10}$ Reduction *S. aureus* | |
| --- | --- | --- | --- | --- |
| | With CuI | Without CuI | With CuI | Without CuI |
| 24 hr | >5.04 | −0.49 | >5.15 | 0.15 |

Example 35

Nail Polish with Antimicrobial Additive and Testing

In order to demonstrate the incorporation of antimicrobial particles in to a nail polish (coating), a commercial water based nail polish was evaluated. A water-based nail polish WaterColors Clear water-based nail enamel, was obtained from Honeybee Gardens Inc. (Leesport, Pa. The ingredients from the labels of these products were listed in Table 29.

TABLE 29

| Ingredients |
| --- |
| Water, water-miscible acrylic, polyurethane formers and thickeners, non-ionic soaps. May contain: ultramarine blue, carmine, mica, iron oxides, and/or titanium dioxide |

The weight percent solids of the nail polish was determined by allowing a measured amount to dry in air for greater than 24 hours at ambient temperature and determining the weight loss upon drying.

The particles used were prepared by the grinding method with a composition of 85.7% CuI and 14.3% Bioterge PAS-8S. The grinding conditions are shown in Table 30. The average particle size was 320 nm. Dry copper iodide based antimicrobial powders were incorporated in the nail polishes at 1 wt % Cu (3 wt % CuI) by mechanical mixing.

TABLE 30

| Solids Proportion by Weight % | | Total Solids (g) | Water (mL) | Mill (RPM) | Pump (RPM) | Media Size (mm) | Grinding Time (min) |
|---|---|---|---|---|---|---|---|
| Metal Compound, % | Functionalization agent(s), % | | | | | | |
| CuI, 85.7 | Bioterge, 14.3 | 3 | 200 | 4200 | 600 | 0.1 | 30 |

Nail polish with the antimicrobial additive were coated on 2-inch square, stainless steel substrates and allowed to dry for greater than 24 hours. Nail polishes without the antimicrobial additive were coated in the same fashion to serve as standards. All of these coatings were evaluated for antimicrobial activity in the manner discussed earlier for other coatings. Over 24 hour period the control sample showed a $log_{10}$ reduction of −1.16 (which shows growth), while the reduction in samples with the antimicrobial additive was 5.89. This shows a strong antimicrobial activity in samples with functionalized CuI particles. This nail polish along with its cosmetic appeal may also be used as antifungal coating to kill fungus on already infected nails.

Example 36

Preparation of Antimicrobial CuI Infused in Porous Silica and Treated with Surfactant Copper iodide (7.89 g) was added to a 1 L pear shaped flask along with a stir bar and acetonitrile (400 ml). This solution was then left to stir at room temperature for several hours. The resulting solution was clear and pale yellow in color.

The clear, pale yellow solution was then mixed with 25 g of Zeothix™ 265, a 3 μm silica (obtained from Huber). This solution was left to stir for one hour at room temperature to give a viscous, milky white/off-white solution. This solution was then dried on the rotary evaporator at room temperature, 30° C. and 60° C. to give a pink powder.

The resulting pink powder was then dispersed in 300 ml of deionized water along with 0.3945 g Stepanol™ WA-100 (sodium lauryl sulfate obtained from Stepan). The solution was stirred at room temperature for two hours and was a milky, pale yellow color. The solution was then dried overnight in the oven at 85° C. to give a pale green/orange/brown solid. When well mixed the solid was tan in color. This powder can now be used as an additive to make various antimicrobial products including wound care products.

Example 37

Copper (I) Iodide Particle Dispersion Formation and Stabilization Using Water Soluble and Insoluble Polymers To a 250 ml round bottom flask fitted with a stir bar and stopper was added 0.123 g of copper iodide, 50 ml of anhydrous acetonitrile and 1.0 ml of poly(dimethylsiloxane). The poly(dimethylsiloxane) had a formula weight of 162.38, boiling point of 101° C./760 mmHg and a viscosity of 0.65 cST. The mixture was stirred at room temperature for 2 hours to give a pale green/blue solution. To this solution was added 2.578 g of polyvinylpyrrolidone with an average molecular weight of 10,000. Upon stirring this resulted in a green solution. The volatiles were removed slowly under reduced pressure (87 mmHg) at 25° C. and after approximately 4 hours a viscous slurry was obtained. The vacuum was increased to 5 mmHg and the bath temperature increased to 30° C. and after 30 minutes a fine dry green powder was obtained. It appeared that any excess poly (dimethylsiloxane) which was not attached to the surface of the particles was removed during the drying process. This powder was dispersed in 25 ml of de-ionized water by stirring to give an opaque white dispersion. This dispersion without agitation was stable for over 24 hours at room temperature. Dynamic light scattering analysis on a diluted sample of the dispersion gave an average particle size of 160 nm.

Example 38

Formation of Fluorosurfactant Functionalized Copper Iodide Particles and their Use in Coatings 200 mL deionized water with 1.5 g 3M Novec FC 4430 (perfluorobutane sulfonate based surfactant from 3M as surface functionalizer) and 8.5 g copper iodide were processed in a Minicer® mill (see Example 15 for mill description) using 100 micron yttria stabilized zirconia grinding media at a mill speed of 4200 RPM and recirculation pump speed of 600 RPM for 180 minutes to form an opalescent milky green dispersion. This aqueous dispersion was concentrated by removing water under reduced pressure. To disperse the particles in an organic solvent, a small amount was dried to a green and grey, tacky solid. This material disperses well in methyl ethyl ketone (MEK). This material also redisperses well in water. Dynamic light scattering showed that the average particle size in water was 150 nm and in MEK it was 100 nm. This material can be used as an antimicrobial additive both in coating and other products formulated in water based systems and solvent based systems which are compatible with MEK.

To test its use in coatings, this material was added to a water based polyurethane coating formulation PU-73 (aliphatic urethane aqueous dispersion (35% solids) sold under the Tradename of ESACOTE™ obtained from Lambeth SpA, (Gallarate, Italy)). 50.0 g of this urethane dispersion was mixed with 1.0 g PZ-28 crosslinking agent (polyfunctional aziridine manufactured by PolyAziridine, LLC Medford, N.J.). This was coated on an aminosilane primed substrate by dip coating and cured for 2 hours at 70° C. to form a clear antimicrobial coating. The amount of copper was 0.25% (as copper iodide, similar to Example 25). In a similar fashion an acrylic antimicrobial coating was made from an MEK based system with copper content (as copper iodide) of 0.25% cured by UV. These coatings were clear.

Example 39

Formation of Antimicrobial Solvent Based Coatings with CuI Functionalized by Aminosilane Surface functionalized CuI additive was made forming a solution of 0.560 g 3-Aminopropyltriethoxysilane (APTES), 20 mL acetonitrile, 0.560 g CuI. This was stirred at room temperature and formed a brown solution. Acetonitrile was partially removed under reduced pressure to form a dispersion of CuI particles in a concentration of 12.5% by weight which were functionalized by APTES. The weight fraction of APTES in this formulation was also 12.5 wt %. This additive was soluble in methyl ethyl ketone (MEK) for use as an additive in coatings.

Example 40

Formation of Citric Acid Functionalized Copper Iodide Particles and Formation of an Antimicrobial Solution 200 mL deionized water was mixed with 1.5 g citric acid (surface functionalizing agent) and 8.5 g copper iodide. This was processed by grinding in a ceramic ball mill using 100 micron yttria stabilized zirconia as in Example 28 for a period of 180 minutes to form a milky white dispersion. This was diluted in water to result in an antimicrobial solution. Solutions were produced with copper concentration ranging from 0.97% by weight down to 10 ppm by weight.

Example 41

Preparation of an Antimicrobial Cleaning (Disinfectant) Solution 1.36 g sodium lauryl surfate (functionalizing agent), 25.7 g CuI, and 257 mL deionized water were combined and processed in a ceramic ball mill as described in Example 28, with a pump speed of 100 RPM for 1300 minutes to form a milky white dispersion of surface functionalized CuI at 6.550 wt % solids.

This was combined with 5% aqueous solution of citric acid to form a 60 ppm Cu dispersion at pH of 2 to form an antimicrobial solution which may be applied by putting them in wipes or applied on surfaces, e.g., by spraying. Dynamic light scattering showed that the average particle size was 100 nm after aging for one week.

Another cleaning solution was formed by taking the above and adding a vinyl acetate-PVP copolymer (VA64 from BASF)) to a final concentration 3400 ppm. This polymer would leave a film on the surface (film former) after the solution is wiped and or dried with trapped antimicrobial particles so that the surface will continue to be microbe resistant long after the cleaning/application of this material. These cleaning solutions may also be formed by adding porous particles with antimicrobial additives loaded in the pores (see Example 36)

Example 42

Anionic Surfactant Functionalized CuI Particles Produced by Milling in Water-acetonitrile Mixture 4.25 g CuI, 0.75 g sodium lauryl sulfate (surface functionalizer) was combined with 30 g acetonitrile, 170 g deionized water, This mixture was processed in a ceramic ball mill using 100 micron yttria stabilized zirconia grinding media at a mill speed of 4200 RPM and recirculation pump speed of 600 RPM for 300 minutes to form a foamy, milky dispersion. Upon completion of the above process additional 200 mL of deionized water was added and milling continued for 30 minutes to form an opalescent, foamy, white dispersion. This dispersion (in liquid form or after drying) forms additive to liquid or solid formulations and products.

Example 43

Antimicrobial Solvent Based Nail Polish

A mixture of 42.5 g CuI and 7.5 g Novec FC 4430 (3M) in 200 ml deionized water was milled for 1000 minutes at 4200 rpm mill speed with a pump speed of 600 rpm using the 100 μm YTZ media. Other milling details were as in Example 28. This dispersion, after milling was then dried on the rotary evaporator at 40° C. The resulting solid was green in color.

The solvent based nail polish used was Nina Ultra Pro Salon Formula Super Dry Topcoat #709290 (produced by Cosmetic Design Group, Culver city, CA). The nail polish was clear and colorless and was found to have a solids content of 25.93%.

The CuI/Novec FC 4430 additive (0.0018 g) was mixed with 0.5 ml acetonitrile and 0.25 ml isopropanol and was easily dissolved at room temperature with stirring. This solution was clear and colorless. The Nina Ultra Pro Salon Formula Super Dry Topcoat (2 g) was added to the CuI/Novec FC 4430 solution and was left to stir for 10 minutes to give a clear, colorless solution.

A 5 cm×5 cm aluminum substrate was coated with the Nina Ultra Pro Salon Formula Super Dry Topcoat containing the CuI/Novec FC 4430 additive from above. One coating was painted by hand and was left to dry at room temperature. The coating was clear and colorless. A coating of Nina Ultra Pro Salon Formula Super Dry Topcoat with no additive was also painted by hand onto a 5 cm×5 cm aluminum substrate and was left to dry at room temperature. This coating was also clear and colorless. Upon examination, the coating with the CuI/Novec FC 4430 additive was indistinguishable in appearance from the polish coating with no additive. These coatings with the CuI/FC 4430 additive may also be used on nails as antifungal coating to kill fungus which may be present prior to the application of the coating.

Example 44

Preparation of Masterbatch and their Incorporation on Thermoplastic Products 300 mL deionized water with 6.25 g sodium lauryl sulfate and 118.75 g copper iodide were processed in a Minicer® mill (see Example 15 for mill description) using 100 micron yttria stabilized zirconia grinding media at a mill speed of 4200 RPM and recirculation pump speed of 600 RPM for 240 minutes to form a milky white dispersion. 13.97 g PEG (Carbowax 8000, Dow) was added to the slurry and processed for an additional 120 minutes. This dispersion was dried to form a pink powder by removing water under reduced pressure.

This material was incorporated into a thermoplastic polyester (crystalline polyethylene terephtlate-fiber grade) masterbatch. Two masterbatches were made by incorporating 7 and 17.6% of the above blend in virgin PET and then melt-compounded on a twin screw extruder and then the extrudate was pelletized to form a masterbatch. Incorporation of these masterbatch pellets in a concentration of 5% by weight in virgin PET would result in antimicrobial PET with copper concentrations of 0.1 and 0.25%, respectively.

Example 45

Formation of Block Copolymer Functionalized Copper Iodide Particles and their Use in Coatings 300 mL deionized water with 20 g DisperBYK-190 (solution of high molecular weight block copolymer with pigment affinic groups from BYK USA Inc, Wallingford, Conn.) and 80.0 g copper iodide were processed in a Minicer® mill (see Example 15 for mill description) using 100 micron yttria stabilized zirconia grinding media at a mill speed of 4200 RPM and recirculation pump speed of 600 RPM for 1000 minutes to form an opalescent milky green dispersion. This aqueous dispersion was concentrated by removing water under reduced pressure. Dynamic light scattering showed that the average particle size in water was 150 nm. This concentrated dispersion can be dispersed in water based coating formulation. When a dilute aqueous dispersion of this material was tested for antimicrobial properties (with copper concentration being 59 ppm), in 30 minutes, the $\log_{10}$ reduction for P. Aeruginosa (ATCC 9027) was >4.93, and the $\log_{10}$ reduction for S. aureus (ATCC 25923) was 3.42.

To test its use in coatings, this material was added to a water based polyurethane coating formulation PU-73 (aliphatic urethane aqueous dispersion (35% solids) sold under the Tradename of ESACOTE™ obtained from Lambeth SpA, (Gallarate, Italy)). 50.0 g of this urethane dispersion was mixed with 1.0 g PZ-28 crosslinking agent (polyfunctional aziridine manufactured by PolyAziridine, LLC Medford, N.J.). This was coated on an aminosilane primed substrate by dip coating and cured for 2 hours at 70° C. to form a clear antimicrobial coating. The amount of copper was 0.25% (as copper iodide, similar to Example 25).

Example 46

Formation of Polyamine Amide and Acidic Polyester Functionalized Copper Iodide Particles 200 mL ethanol with 0.5 g Anti-Terra-U (solution of a salt of unsaturated polyamine amides and low molecular weight acidic polyesters from BYK) and 10.0 g copper iodide were processed in a Minicer® mill (see Example 15 for mill description) using 100 micron yttria stabilized zirconia grinding media at a mill speed of 4200 RPM and recirculation pump speed of 600 RPM for 180 minutes to form an opalescent ethanol green dispersion. This dispersion was dried to form a pink powder by removing water under reduced pressure. This powder disperses well in various organic solvents including butyl acetate. When a dilute aqueous dispersion of this material was tested for antimicrobial properties (with copper concentration being 59 ppm), in 30 minutes, the $\log_{10}$ reduction for P. Aeruginosa (ATCC 9027) was >4.93

Example 47

Formation Acidic Polyester Functionalized Copper Iodide Particles 300 mL ethanol with 5.0 g BYK-W 985 (solution of acidic polyester from BYK) and 92.5 g copper iodide were processed in a Minicer® mill (see Example 15 for mill description) using 100 micron yttria stabilized zirconia grinding media at a mill speed of 4200 RPM and recirculation pump speed of 600 RPM for 1000 minutes to form an opalescent milky green dispersion. This aqueous dispersion was dried to form a pink powder by removing ethanol under reduced pressure.

Example 48

Formation of Alkylol Ammonium Salt Copolymer (Ionic Polymer) Functionalized Copper Iodide Particles and their Use in Coatings 200 mL ethanol with 1.85 g DisperBYK-180 (alkylol ammonium salt of a copolymer with acid groups from BYK) and 10.0 g copper iodide were processed in a Minicer® mill (see Example 15 for mill description) using 100 micron yttria stabilized zirconia grinding media at a mill speed of 4200 RPM and recirculation pump speed of 600 RPM for 330 minutes to form an opalescent milky green dispersion. This ethanol dispersion is compatible with water based coatings and many solvent systems. When a dilute aqueous dispersion of this material was tested for antimicrobial properties (with copper concentration being 59 ppm), in 30 minutes, the $\log_{10}$ reduction for P. Aeruginosa (ATCC 9027) was >4.78.

To test its use in coatings, this dispersion was added to a water based polyurethane coating formulation PU-73. 50.0 g of this urethane dispersion was mixed with 1.0 g PZ-28 crosslinking agent. This was coated on an aminosilane primed substrate by dip coating and cured for 2 hours at 70° C. to form a clear antimicrobial coating. The amount of copper was 0.25% (as copper iodide, similar to Example 25). In a similar fashion an acrylic antimicrobial coating was made from an MEK based system with copper content (as copper iodide) of 0.25% which was cured by UV. These coatings were clear.

The acrylic coatings were tested for their antimicrobial properties by evaluating them against S. aureus (ATCC #25923) using JIS2801-2000 as described earlier. The acrylic coating without the antimicrobial additive showed a decrease in this strain of 0.10±0.11 and 1.05±0.92 $\log_{10}$ reductions in a period of 6 and 24 hr respectively, for the same time periods coatings with antimicrobial additive (0.25 wt % copper) resulted in reductions of 3.47±0.61 and >4.40±0.00.

Example 49

Formation of Copper-silver-iodide-bromide Solid Solution for Wound Dressings (1 wt % Cu (as CuI) in Dry Solid)

30 mL acetonitrile, 0.066 g silver bromide, 0.933 g copper iodide, and 31.1 g PVP-10K were stirred to form a clear green solution. This solution was dried to form a white powder by removing acetonitrile under reduced pressure. This powder was dispersed in water. This aqueous dispersion was used to form a wound dressing as in Example 33c. This was tested as in Example 33d. A complete kill of bacteria was observed within 24 hours.

Example 50

Formation of Copper-potassium-iodide Solid Solution for Wound Dressings (1 wt % Cu (as CuI) in Dry Solid)

30 mL acetonitrile, 1.0 g potassium iodide, 1.0 g copper iodide, and 32.33 g Copolymer Vinyl acetate-Vinyl pyrrolidone (Luvitec VA64, BASF, Germany) were stirred to form a clear orange solution. This solution was applied to form a wound dressing. Upon drying, copolymer functionalized CuI particles were formed. This wound dressing was tested as in Example 33d. A complete kill of bacteria was observed within 24 hours. Another wound dressing containing the same amount of potassium iodide was similarly prepared and did not appear to kill bacteria following the same procedure.

Example 51

Formation of Acidic Polyester Modified Copper Iodide Silica Blend 400 mL deionized water, 15 g acidic polyester modified copper iodide (see Example 46), and 15 g 3μ, silica (Zeothix 265) were processed in a Minicer® mill (see Example 15 for mill description) using 100 micron yttria stabilized zirconia grinding media at a mill speed of 4200 RPM and recirculation pump speed of 600 RPM for 180 minutes to form an opalescent milky dispersion. This dispersion was dried by removing water under reduced pressure to form a gray to pink solid.

Example 52

Formation of Antimicrobial Dental Adhesive with an Inorganic Copper Salt

Kerr Optibond XTR dental adhesive (Kerr Corporation, Orange, Calif.) was combined with an inorganic copper salt. This copper salt was surface functionalized (copper iodide functionalized with bioterge, see Example 35). Ethanol (solvent) was added to the adhesive to reduce its viscosity in order to effectively mix the functionalized CuI particles. Ethanol was removed under reduced pressure to form a viscous CuI containing dental adhesive paste. This dental adhesive was coated on to aluminum substrates and cured under UV. The substrates were further cured at 130° C. under nitrogen at 60 psi for 20 minutes using a BelleGlass™ HP Curing Unit (Kerr Corporation, Orange, Calif.).

Dental adhesive coatings were formed at 0.5, 0.25, and 0.0% Cu by weight (as CuI). These coatings were evaluated against *streptococcus mutans* over a period of six hours using JIS2801-2000 procedure as described above. The $log_{10}$ reductions of the microbes in these coatings were >3.93, >3.81 and 0.59 respectively.

Example 53

Improved Dispersibility of CuI by Addition of Soluble Iodide Salt

To a round bottom flask was added 30 mL of anhydrous acetonitrile, 15 g of PVP 10K. This was stirred to form a clear solution. To this was added copper iodide or copper iodide along with sodium iodide. Since acetonitrile is a solvent for CuI, clear solutions were formed in all cases. Both of these solutions was dried under reduced pressure and redispersed separately in water and linear alcohols methanol, ethanol, propanol, and butanol. These solutions were monitored for clarity (stability) for 1 month as described in the table below. The materials which did not have NaI could not be dispersed in water and ethanol. Further, the dispersions with NaI were also stable on standing. As discussed in the next example use of small amounts of NaI while preparing functionalized particles by grinding in water improved their processability.

TABLE 31

| Sample ID | CuI (g) | Salt, NaI (g) | PVP 10K (g) | Redisperses in Water as translucent dispersion | Redisperses in Alcohol as transluscent dispersion |
|---|---|---|---|---|---|
| A | 0.367 | 0.133 | 15 | Yes, Stable | Yes, Stable |
| B | 0.367 | 0.000 | 15 | No | Not applicable |

Example 54

Improved Dispersibility of a Salt with Low Water Solubility with Addition of a High Water Solubility Salt The use of sodium iodide (a water soluble salt) was evaluated to improve dispersability of functionalized copper iodide particles. A clear solution was made with 200 ml of deionized water and 0.399 g of NaI. To this solution 1.01 g of copper iodide was added. To this mixture 45 g of PVP 10K (PVP with a molecular weight of 10,000) was added and still CuI did not dissolve. 200 mL deionized water with 45 g PVP 10K, 1.101 g copper iodide, and an amount of sodium iodide were processed in a Minicer® mill (see Example 15 for mill description) using 100 micron yttria stabilized zirconia grinding media at a mill speed of 4200 RPM and recirculation pump speed of 600 RPM for 1000 minutes. Sample was also made without any sodium iodide but with the same amount of PVP (sample B). Particle size was measured of the as prepared dispersions by dynamic light scattering. Particle size was also measured for the dispersions after being dried under reduced pressure and redispersed in water by dynamic light scattering. Also to be noted that addition of soluble iodide salt (as sodium iodide) along with PVP helped in decreasing the particle size of CuI more efficiently, and further, such dispersions were highly stable.

TABLE 32

| Sample ID | CuI (g) | Salt, (g) | PVP K17 (g) | Water | Average particle Size (as prepared) | Average particle Size (dried and redispersed) | Remarks |
|---|---|---|---|---|---|---|---|
| A | 1.101 | NaI, 0.399 | 45 | 200 mL | 5 nm | 5 nm | Clear green dispersion |
| B | 1.101 | None, 0.000 | 45 | 200 mL | >1 micron | >1 micron | Hazy yellow dispersion, |

TABLE 32-continued

| Sample ID | CuI (g) | Salt, (g) | PVP K17 (g) | Water | Average particle Size (as prepared) | Average particle Size (dried and redispersed) | Remarks |
|---|---|---|---|---|---|---|---|
| | | | | | | | Large amount of sediment |

In another experiment the benefits seen by adding soluble iodide were reevaluated by lowering its concentration relative to the CuI used. In addition, relative amount of PVP was also decreased. 200 mL deionized water with 1.0 g PVP 10K, 4.0 g copper iodide, and 0.1 g of sodium iodide were processed in a Minicer® mill (see Example 15 for mill description) using 100 micron yttria stabilized zirconia grinding media at a mill speed of 4200 RPM and recirculation pump speed of 600 RPM for 250 minutes. Particle size was measured of the as prepared dispersion by dynamic light scattering to be 10-80 nm. Particle size was also measured for the dispersion after being dried under reduced pressure and redispersed in water by dynamic light scattering to be 10-80 nm. Both the as prepared and dried and redispersed dispersions exhibit a much stronger resistance to settling than similar preparations without the addition of sodium iodide.

Example 55

Efficacy in CuI Containing Wound Dressings by Addition of Acids and Salts

In this example the CuI/PVP samples were made using PVP with a molecular weight of 10,000 and along with sodium iodide and was prepared as detailed in Example 53, Sample A.
- a) To a round bottom flask was added 0.2 g Citric Acid (Citric acid >99%, Aldrich C0759), 1 g of prepared CuI/PVP 10 k powder (2.38 wt % CuI) and 5 mL DI-water.
- b) a) To a round bottom flask was added 0.2 g Citric Acid (Citric acid >99%, Aldrich C0759), 1 g of PVP 10K powder and 5 mL DI-water.
- c) To a round bottom flask was added 0.2 g Ascorbic Acid (L-Ascorbic acid >99%, Aldrich 95210), 1 g of prepared CuI/PVP 10K powder (2.38 wt % CuI) and 5 mL DI-water.
- d) a) To a round bottom flask was added 0.2 g Ascorbic Acid (L-Ascorbic acid >99%, Aldrich 95210), 1 g of PVP 10K powder and 5 mL DI-water.
- e) To a round bottom flask was added 0.2 g Citric Acid (Citric acid >99%, Aldrich C0759), 0.1 g Sodium Bicarbonate, and 5 mL DI-water. This was allowed to react to form a citrate salt and form a clear solution with a pH of 4. Then 1 g of prepared CuI/PVP 10 k powder (2.37 wt % CuI) was added.
- f) To a round bottom flask was added 0.2 g Ascorbic Acid (L-Ascorbic acid >99%, Aldrich 95210), 0.1 g Sodium Bicarbonate, and 5 mL DI-water. This was allowed to react to form a citrate salt and form a clear solution with a pH of 4. Then 1 g of prepared CuI/PVP 10 k powder (2.38 wt % CuI) was added.

These aqueous dispersions were used to form wound dressing as in Example 33c. E. coli (ATCC#25922) was used instead of P. Aeruginosa to test the antimicrobial properties. These were tested by culturing a single colony of E. coli (ATCC #25922) overnight to stationary phase in tryptic soy broth (TSB). The following day, the culture was diluted in TSB to read optical density in a Synergy 2 reader (from Biotek Instruments Inc, Winooski, Vt.). Following this, 0.25 ml of culture was plated onto petri dishes containing tryptic soy agar (TSA). 10 mm circular pieces of gauze samples were then placed onto inoculated plates. Each piece of gauze was lightly pressed to ensure contact with the agar and then the plate was inverted and incubated at 37° C. for 16-24 hours. After this time period, a zone of inhibition (ZOI) was observed around the wound dressings which was optically clear (not hazy) showing that no bacteria grew in this zone. The size of this zone (zone of inhibition) was noted in mm from the perimeter of the wound dressings after 24 hours. The zone of inhibition around sample (a) was 5.0 mm, (b) 2.5 mm, (c) 3.0 mm, (d) 0.5 mm, (e) 5 mm, (f) 3 mm.

Example 56

Efficacy in CuI Containing Wound Dressings by Addition of Citrate Salt at Different Concentrations In this example the CuI/SLS powder used was 75/25 by weight and was produced by grinding as described in Example 28.
- (a) To a round bottom flask was added 0.2 g Citric Acid (Citric acid >99%, Aldrich C0759), 0.0875 g Sodium Bicarbonate (Aldrich S6014) and 5 g DI-water. The mole ratio of citric acid to sodium bicarbonate was 1. This was allowed to react and form a clear solution with a pH of 3.5. To this solution was added 1 g of PVP 10K and 0.3 g of prepared CuI/SLS powder (25% Cu). The pH remained constant and a blue or green color developed.
- (b) A sample was prepared as in example (a) with an increased amount of sodium bicarbonate. The amount of sodium bicarbonate used was 0.175 g. The mole ratio of citric acid to sodium bicarbonate was 2. The pH was 5.5. All other parameters remained as in example (a).
- (c) A sample was prepared as in example (a) with an increased amount of sodium bicarbonate. The amount of sodium bicarbonate used was 0.263 g. The mole ratio of citric acid to sodium bicarbonate was 3. The pH was 7. All other parameters remained as in example (a).
- (d) To a round bottom flask was added 0.2 g Citric Acid (Citric acid >99%, Aldrich C0759), 0.263 g Sodium Bicarbonate (Aldrich S6014) and 5 g DI-water. The mole ratio of citric acid to sodium bicarbonate was 3. This was allowed to react and form a clear solution with a pH of 7. To this solution was added 1.225 g of PVP 10K and 0.075 g of SLS powder.

These aqueous dispersions were used to form wound dressing and tested as in Example 55 and tested against E. coli (ATCC#25922). The zone of inhibition around sample (c) was larger than (a) and (b). The zone of inhibition around sample (b) was larger than (a). Sample (d) showed no zone of inhibition. After testing it was observed that sample (c) had a stronger blue color, followed by samples (b) and (a).

Example 57

Improved Dispersibility of CuI by Milling with Soluble Salts and Polymer, and Use of Metals a) Copper iodide, sodium iodide, polyvinvylpyrrolidone K17, and deionized water were combined as described in the table below. These materials were processed together in a bead mill (see Example 15 for the description of the mill) using 100 micron grinding media (3M™ Micro Milling Media ZGC) at a mill speed of 4200 RPM and recirculation pump speed of 600 RPM.

TABLE 33

| CuI (g) | PVP (g) | NaI (g) | DI-Water (mL) | Grinding Time (min) |
|---------|---------|---------|---------------|---------------------|
| 9       | 40      | 1       | 150           | 1000                |
| 9       | 2       | 1       | 200           | 350                 |
| 9       | 2       | 0.25    | 200           | 1200                |
| 9       | 0.9     | 0.1     | 200           | 450                 |
| 9       | 0.95    | 0.05    | 200           | 350                 |
| 18      | 1.95    | 0.05    | 200           | 1000                |
| 90      | 9       | 1       | 140           | 350                 |
| 90      | 9.5     | 0.5     | 200           | 1330                |

Each milled product appeared as a semi translucent opalescent dispersion that was stable against settling with particle sizes around 10-30 nm. The dispersions were dried to form purple colored solids under reduced pressure. Subsequent redispersal formed dispersions similar to as before drying with particle sizes around 10-30 nm.

b) 18 g Copper iodide, 0.05 g sodium iodide, 1.95 g copovidone VA64 (copolymer of polyvinvylpyrrolidone and vinyl acetate), and 200 mL deionized water were combined and processed together in a Minicer® mill (see Example 15 for mill description) using 100 micron grinding media (3M™ Micro Milling Media ZGC) at a mill speed of 4200 RPM and recirculation pump speed of 600 RPM for 350 minutes.

This milled mixture appeared as a semi translucent opalescent dispersion. This dispersion was dried to a solid under reduced pressured and subsequently redispersed to form a similar dispersion as before drying with a particle size around 10-30 nm.

c) 9 g Copper iodide, polyvinvylpyrrolidone 0.9 g PVP K17, 0.1 g silver nitrate, and deionized water were combined and processed together in a Minicer mill (see Example 15 for mill description) using 100 micron grinding media (3M™ Micro Milling Media ZGC) at a mill speed of 4200 RPM and recirculation pump speed of 600 RPM for 400 minutes. A translucent dispersion was formed after processing.

d) 9 g of copper iodide and 0.9 g PVP K17 were processed as in (c) using 0.1 g copper(I) acetate rather than silver nitrate. A translucent dispersion was formed after processing.

e) 9 g of copper iodide and 0.9 g PVP K17 were processed as in (c) using 0.1 g elemental silver (10 micron powder) rather than silver nitrate. A translucent dispersion was formed after processing.

f) 9 g of copper iodide and 0.9 g PVP K17 were processed as in (c) using 0.1 g elemental copper (10 micron powder) rather than silver nitrate. A translucent dispersion was formed after processing.

g) 9 g of copper iodide and 0.9 g PVP K17 were processed as in (c) using 0.1 g elemental zinc (10 micron powder) rather than silver nitrate. A translucent dispersion was formed after processing.

h) 9 g of copper iodide and 0.9 g PVP K17 were processed as in (c) using 0.1 g elemental iodine rather than silver nitrate. A translucent dispersion was formed after processing.

Example 58

Improved Dispersibility of AgI by Milling with Soluble Iodide and Polymer a) 9 g Silver iodide, 0.1 g potassium iodide, 0.9 g polyvinylpyrrolidone K17, and 200 mL deionized water were combined and processed together in a ceramic ball mill using 100 micron grinding media (3M™ Micro Milling Media ZGC) at a mill speed of 4200 RPM and recirculation pump speed of 600 RPM for 350 minutes.

This milled mixture appeared as a semi translucent green dispersion. This dispersion was dried to a solid under reduced pressured and subsequently redispersed to form a similar dispersion as before drying with a particle size around 10-30 nm.

Example 59

Wound Dressing Compositions a) To a round bottom flask was added 10 g trisodium citrate (Aldrich), 6.67 g of copper iodide powder (as prepared in Example 57a as 90% CuI, 9% PVP, and 1% NaI), 83.33 g PVP K17, and 300 mL deionized water. This aqueous dispersion had 25% solids and was used to form wound dressing by applying 1 g of liquid dropwise to a 2×2 inch cellulose polyester fabric and drying the fabric in an oven at 75° C. on a glass tray.

b) Similar wound dressings were prepared with 6.67 g of copper iodide powder (as prepared in Example 57a as 90% CuI, 9% PVP, and 1% NaI), 93.33 g PVP K17, and 300 mL deionized water.

c) Standard wound dressings were similarly prepared and consisted of 10% trisodium citrate and 90% PVP K17.

d) These wound dressings were tested by applying a 10 mm circular swatch to a bacterial *pseudomonas aeruginosa* (ATCC#9027) biofilm, such that the biofilm was completely covered by the wound dressing. The biofilm had been grown overnight on a 0.2 micron membrane on agar and transferred to fresh agar upon application of the wound dressing. Bacterial reductions were determined by removing the wound dressing, sonicating the membranes in PBS, and plating the PBS at 10× dilutions to count viable colony forming units.

e) In biofilm testing described above the samples containing both copper iodide and trisodium citrate (sample a) performed superior to samples without citrate and without both citrate and copper iodide (sample b and c).

Example 60

Preparation and Testing of Wound Dressings a) Preparation of Wound Dressings
i) Wound dressings were prepared by combining 0.0667 g copper iodide powder as described in Example 57a (90% CuI, 1% NaI, 9% PVPK17), 1.733 g PVP K17, 0.20 g trisodium citrate, and 6 mL deionized water. This dispersion was applied to a 4 sq in piece of gauze as in Example 55 at 0.25 g solids per 4 sq in. This was subsequently dried and further processed to form wound dressings as described in Example 55.

ii) 0.0667 g copper iodide powder as described in Example 57c (90% CuI, 1% AgNO$_3$, 9% PVPK17), 1.733 g PVP K17, 0.20 g trisodium citrate, and 6 mL deionized water were mixed to form wound dressings as in (i).
iii) 0.0667 g copper iodide powder as described in Example 57a (90% CuI, 1% NaI, 9% PVPK17), 1.333 g PVP K17, 0.20 g trisodium citrate, 0.40 g ascorbic acid, and 6 mL deionized water were mixed form wound dressings as in (i).
iv) 1.733 g PVP K17, 0.20 g trisodium citrate, and 6 mL deionized water mixed to form wound dressings as in (a).

b) Testing of Wound Dressings

Wound dressings (i-iv) were tested as described in Example 55 using *Pseudomonas aeruginosa* (ATCC#9027), *Staphylococcus aureus* (ATCC#25923), and *Escherichia coli* (ATCC#25922). Unless mentioned otherwise only these bacterial strains were used to test the wound dressings in other examples.

The zone of inhibition (ZOI) for (i) and (ii) were equivalent for all three microbes. The ZOI for (iii) was larger than both (i) and (ii) for all three microbes. There was no ZOI for (iv) for *Pseudomonas aeruginosa* and *Escherichia coli*, however, there was a ZOI smaller than (i) or (ii) against *Staphylococcus aureus*.

Example 61

Preparation and Testing of Wound Dressings a) Preparation of Copper Iodide Wound Dressing 0.133 g copper iodide powder as described in Example 57a (90% CuI, 1% NaI, 9% PVPK17), 1.266 g PVP K17, 0.20 g trisodium citrate, 0.40 g ascorbic acid, and 6 mL deionized water were mixed form wound dressings as in Example 33c. The loading of solids was at 0.50 g per 4 sq in.

b) Preparation of Control Wound Dressing 1.333 g PVP K17, 0.20 g trisodium citrate, 0.40 g ascorbic acid, and 6 mL deionized water mixed to form wound dressings as in Example 33c. The loading of solids was at 0.50 g per 4 sq in. This sample had no copper.

c) Testing of Wound Dressings

Copper iodide and Standard wound dressings were tested along with Aquacel Ag (silver containing commercial wound dressing) as described in Example 55 using *Pseudomonas aeruginosa* (ATCC#9027), *Staphylococcus aureus* (ATCC#25923), and *Escherichia coli* (ATCC#15597). Zone of inhibition results are described in the table below.

TABLE 34

| Plate # | Organism | Sample | ZOI (mm) |
|---|---|---|---|
| 1 | *Psudomonas aeruginosa* (ATCC# 9027) | Control | 0.0 |
|  |  | Aquacel Ag | 1.6 |

TABLE 34-continued

| Plate # | Organism | Sample | ZOI (mm) |
|---|---|---|---|
| 2 | *Psudomonas aeruginosa* (ATCC# 9027) | CuI | 1.6 |
|  |  | Aquacel Ag | 1.6 |
| 3 | *Staphylococcus aureus* (ATCC# 25923) | CuI | 1.6 |
|  |  | Aquacel Ag | 1.6 |
| 4 | *Escherichia coli* (ATCC# 15597) | CuI | 1.6 |
|  |  | Aquacel Ag | 1.6 |

Example 62

Wound Dressings Prepared with Alternative Polymers 0.133 g copper iodide powder as described in Example 57a (90% CuI, 1% NaI, 9% PVPK17), 1.266 g of polymer as described in the table below, 0.20 g trisodium citrate, 0.40 g ascorbic acid, and 6 mL deionized water were mixed form wound dressings as in (a) at 0.75 g per 4 sq inch. These wound dressings were tested against *Pseudomonas aeruginosa* (ATCC#9027) as described in Example 55. All samples had equivalent zones of inhibition as described in the table below.

TABLE 35

| Polymer | Zone of Inhibition (mm) |
|---|---|
| PVP K17 | 1.5 |
| PVP MW = 55,000 | 1.5 |
| VA64 Copolymer | 1.5 |
| 80% PVP K17, 20% Carboxymethylcellulose | 1.5 |
| PEG MW = 8,000 | 1.5 |
| None | 1.5 |

Example 63

Wound Creams a) Antimicrobial wound creams were prepared by sodium carboxymethycellulose, trisodium citrate, and copper iodide powder as prepared in Example 57a as 90% CuI, 9% PVP, and 1% NaI. These creams were prepared at 6% sodium carboxymethycellulose, 10% trisodium citrate, and copper levels of 0.00%, 0.25%, 0.50%, 1.00%, and 5.00%.

b) These wound creams were tested using a zone of inhibition method. A 6 mm well was formed in the center of an inoculated agar plate and filled with the wound cream. Each cream was run in triplicate on three separate plates. Each plate was allowed to incubate overnight at 37° C. and then the zone of inhibition was measured. Each cream was tested against *Pseudomonas aeruginosa* ATCC#9027) and *Staphylococcus aureus* (ATCC#25923).

c) The zone of inhibition measured results of wound creams described in (a) along with commercial bacitracin ointment tested as in (b). These measurements are in cm for the diameter of the zone of inhibition including the well.

TABLE 36

|  | 0.00% Cu | 0.25% Cu | 0.50% Cu | 1.00% Cu | 5.00% Cu | Bacitracin |
|---|---|---|---|---|---|---|
| *P. aeruginosa* | 1.0 ± 0.3 | 1.2 ± 0.2 | 1.1 ± 0.0 | 1.4 ± 0.2 | 2.1 ± 0.0 | 0.6 ± 0.1 |
| *S. aureus* | 1.5 ± 0.1 | 1.6 ± 0.1 | 1.8 ± 0.1 | 2.2 ± 0.2 | 4.4 ± 0.4 | 0.6 ± 0.1 |

Example 64

Functionalization of CuI with SiO$_2$ and its Use in a Coating

To a one liter flask was added 200 mL deionized water (18 mΩ-cm) with pH adjusted to 2.0 using dilute HCl and 10.0 g (0.05251 m) of cuprous iodide. The mixture was stirred using a high shear mixer (Ross LSK Mixer) at a maximum speed of 20,000 rpm. While mixing at 15,000 rpm 4.75 g (0.228 m) of tetraethylorthosilicate (Aldrich, 99%) was added dropwise. This resulted in a fine white dispersion. This mixture was processed in a Minicer® mill (see Example 15 for mill description) using 100 micron grinding media (3M™ Micro Milling Media ZGC) at a mill speed of 4200 RPM and recirculation pump speed of 600 RPM for 1300 minutes. After 4 hours of milling the pH had increased to 4.0, after 6 hours of milling the pH had increased to 5.6, and after completion of milling (1300 min) the pH had increased to 6.3. The dispersion had developed an opaque white appearance with pink foam.

This dispersion was then removed from the mill and placed under high speed stirring at 3000 rpm; 0.2 mL of dilute ammonia (3 ml of 28% ammonia solution in 25 ml of deionized water) was added and allowed to mix for 1 hour. The pH initially went basic and then decreased to a steady value of 6.0. This dispersion was heated to reflux under magnetic stirring for 2 hours cooled to room temperature and left stirring overnight.

This dispersion was filtered on a 0.8 micron nylon filter (Osmonics) and washed with excess water and ethanol. The filtrate was clear and without color. The dry product was cured in a convection oven at 200° C. overnight to give an off white fine powder of composition 12 wt % SiO$_2$ and 88 wt % CuI. This powder was dispersed in water and its efficacy tested against *P. aeruginosa* (ATCC#9027) at a copper concentration of 60 ppm. Table 37 shows the results after 15 minutes compared to the PBS control. The starting bacterial titer concentration was 2.4×10$^6$ cfu/ml.

TABLE 37

| Time | PBS Control | CuI/SiO2 |
| --- | --- | --- |
| 15 min | 0.07 ± 0.03 | 3.73 ± 0.07 |

The CuI/SiO$_2$ powder was added to Harmony White Paint (Sherwin Williams Interior Acrylic Latex semi gloss "green sure designation") at a copper concentration of 0.1 wt % stirred and stored for six days and the color coordinates (CIE 1931 color space) determined as shown below in the Table below.

TABLE 38

Liquid Paint color properties with and without CuI/SiO$_2$

| | | CIE Color Coordinates | | |
| --- | --- | --- | --- | --- |
| Sample | Storage time | L* | a* | b* |
| Harmony White Paint Liquid | Initial | 88.43 | −0.93 | 2.60 |
| Harmony White Paint Liquid | Six days | 88.39 | −0.93 | 2.57 |
| Harmony Paint Liquid with 0.1 wt % Cu | Initial | 87.77 | −2.30 | 3.86 |
| Harmony Paint Liquid with 0.1 wt % Cu | Six days | 87.16 | −2.59 | 3.60 |

The paint with and without CuI/SiO$_2$ as described in the above table was applied to a 2"×2" aluminum substrate and cured at 85° C. The color coordinates were determined for the painted substrates initially and after storage at 85° C. for six days. The results are listed below in the table.

TABLE 39

Cured paint on aluminum substrate with and without CuI/SiO$_2$ added

| | | CIE Color Coordinates | | |
| --- | --- | --- | --- | --- |
| Sample | Storage time | L* | a* | b* |
| Harmony White Paint Liquid | Initial | 93.98 | −0.84 | 1.80 |
| Harmony White Paint Liquid | Six days at 85° C. | 94.44 | −1.31 | 3.63 |
| Harmony Paint Liquid with 0.1 wt % Cu | Initial | 93.31 | −2.96 | 4.61 |
| Harmony Paint Liquid with 0.1 wt % Cu | Six days at 85° C. | 92.01 | −2.81 | 7.03 |

Paints with these antimicrobial additives may be used for building applications (e.g., indoor applications) for public areas such as hospitals, doctor's offices, restaurants, transit areas and many others.

Example 65

Silica Functionalized Copper Iodide a) 200 mL deionized water (18 mΩ-cm) with pH adjusted to 2.0 using Acetic Acid and 10.0 g (0.05251 m) of cuprous iodide were processed in a bead mill (see Example 15 for mill description) using 100 micron grinding media (3M™ Micro Milling Media ZGC) at a mill speed of 4200 RPM and recirculation pump speed of 600 RPM for 350 minutes. 4.75 g (0.228 m) of tetraethylorthosilicate (Aldrich, 99%) was added and milling was continued for another 10 minutes.

This dispersion was then removed from the mill and placed under high speed stirring at 3000 rpm; 0.2 mL of dilute sodium hydroxide was added and allowed to mix for 1 hour. This dispersion was heated to reflux under magnetic stirring for 1 hour and then cooled to room temperature and left stirring overnight.

This dispersion was filtered on a 0.8 micron nylon filter (Osmonics) and washed with excess water and ethanol. The filtrate was clear and without color. The dry product was cured in a convection oven at 120° C. overnight to give an off white fine powder of composition 12 wt % SiO$_2$ and 88 wt % CuI.

b) Another formulation was processed where 10.0 g of Copper iodide and 4.75 g of tetraethylorthosilicate were milled as in (a) using ethanol rather than deionized water. This dispersion was dried under reduced pressure at room temperature to give a fine powder. All of the other steps were similar.

c) Copper iodide was processed as in (b), where ammonia was used rather than sodium hydroxide.

Example 66

Disinfectant with Acids

Disinfectant solutions D1, D3 and D5 were respectively prepared in deionized water with 5% of ascorbic acid, 5% nitric acid and 5% citric acid as shown in the table below. In addition three additional formulations D2, D4 and D6 were also prepared with these respective acids along with CuI particles functionalized with sodium lauryl sulfate (SLS) to yield a final copper concentration of 60 ppm in these formulations. These were prepared by stirring the components for one hour in sure seal bottles. All of the samples with CuI/SLS were slightly hazy.

TABLE 40

| Ingredient | Formulations | | | | | | | |
|---|---|---|---|---|---|---|---|---|
| (g) | D1 | D2 | D3 | D4 | D5 | D6 | D7 | D8 |
| Water | 50 | 50 | 50 | 50 | 47.5 | 50 | | |
| Ascorbic acid | 2.63 | 2.63 | | | | | | |
| Citric acid | | | 2.63 | 2.63 | | | | |
| Acetic acid | | | | | 2.5 | 2.5 | | |
| CuI/SLS | | 0.0126 | | 0.0126 | | 0.0126 | | |

Ascorbic acid (>99%, Fluka, United Kingdom)
Citric acid, 99% (Sigma-Aldrich Corp., St. Louis, Mo.)
Acetic acid, ≥99.7% (Sigma-Aldrich Corp., St. Louis, Mo.)
CuI/SLS (75/25% by weight prepared as in Example 62)

The pH of both of the acetic acid containing formulation was measured and found to be 2.383 for D5 and 2.346 for D6. This was done using an Orion 290A+pH meter equipped with an Orion Ross Sure-flow Glass Combination pH Electrode. The pH meter was calibrated with pH standards 4, 7 and 10 (all pH standards from ACROS Organics, Geel, Belgium) to give a slope of 98.5.

All of the solutions above were analyzed for their antimicrobial properties by testing them against *Staph aureus*. A hard surface tile (10.8×10.8 cm) was inoculated with $10^9$ CFU *Staph aureus* and spread over the surface. After drying this tile was sprayed with the test solution to cover the tile completely (~2 ml) and was swabbed after a period of two minutes, and the swab was dropped in a DE neutralizing solution diluted 100 times with PBS buffer to ensure that the acidity of the spray solution did not change the pH of the neutralizing solution. These solutions were then cultured on agar plates as described earlier. The results are seen in the Table 41 below.

TABLE 41

Testing Results against *S. aureus* (2 minutes of contact time)
Testing against *S. aureus* ATCC 25923

| PBS Control $Log_{10}$ Reduction | 5% ascorbic acid solution (D1) $Log_{10}$ Reduction | 5% ascorbic acid + CuI/SLS (D2) $Log_{10}$ Reduction | 5% citric acid solution (D3) $Log_{10}$ Reduction | 5% citric acid + CuI/SLS (D4) $Log_{10}$ Reduction | 5% acetic acid solution (D5)* $Log_{10}$ Reduction | 5% acetic acid + CuI/SLS (D6)* $Log_{10}$ Reduction |
|---|---|---|---|---|---|---|
| 0.08 ± 0.07 | 0.65 ± 0.11 | 1.05 ± 0.14 | 0.65 ± 0.08 | 1.78 ± 0.19 | 0.91 ± 0.13 | 1.68 ± 0.14 |

Original titer = 6.80E+07 cfu/mL

*These tests were done separately, the PBS standards for this series read −0.24 ± 0.12

The results show superiority of the formulations in killing the microbes with functionalized CuI particles.

Example 67

Disinfectant with Chitosan

A water based disinfectant solution was prepared with 8% of acetic acid, 60 ppm Cu, 3% Isopropanol and 3400 ppm Chitosan as follows:

In a sure seal bottle equipped with a stir bar, 0.0131 g of copper (I) iodide (75%)/sodium lauryl sulfate (25%) powder, prepared in Example 28, was mixed with 0.186 g chitosan (Sigma-Aldrich Corp., St. Louis, Mo.), 1.65 g isopropanol, 99.5% (Sigma-Aldrich Corp., St. Louis, Mo.) and 48.35 g deionized water. Lastly, 4.4 g acetic acid, ≥99.7% (Sigma-Aldrich Corp., St. Louis, Mo.) was added. This solution was stirred at room temperature for one hour to give a translucent, slightly hazy, colorless solution. The pH of this solution was found to be 2.534 using an Orion 290A+pH meter equipped with an Orion Ross Sure-flow Glass Combination pH Electrode. The pH meter was calibrated with pH standards 4, 7 and 10 (all pH standards from ACROS Organics, Geel, Belgium) to give a slope of 97.9. This solution was also then sent for 2 minute contact testing against *Staph aureus* as in Example 66. The results showed that $Log_{10}$ reduction for the sample in two minutes was >4.25±0.00 and for the PBS buffer the result was 0.53±0.38. The original titer bacterial concentration was 8.85E+06 cfu/mL.

Example 68

Efficacy Against *A. Baumannii*

The CuI functionalized with PVP were prepared with a small amount of NaI added to help with processability (CuI/PVP/NaI weight ratio was 90/9/1). The preparation followed Example 57a excepting with different parameters (media size was 300 μm, milling time was 1,000 minutes and the speed was 2,000 rpm), The average particle size established by Dynamic light scattering (DLS) was 150 nm. CuI functionalized particles with SDS were prepared as in Example 28, and the weight ratio of CuI to SDS was 75:25. The average particle size established by DLS was 200 nm. The efficacy of these particles was evaluated in solution against bacteria *A. Baumannii* at 60 ppm Cu concentration (present as surface functionalized CuI particles). After 5 minutes of contact, the CuI/SLS reduced the bacterial count measured on a $Log_{10}$ scale by >5.08, and for CuI/PVP this was >5.34, i.e., in both cases we were below the detection limits when starting out with initial bacterial titer counts at $1.08×10^7$ CFU/ml of bacteria. $Log_{10}$ reductions for both at 15, 30 and 60 minutes were >5.34. Control samples with PVP or SDS did not show any reduction at 60 minutes.

Example 69

Body Cleaner (Shampoo) Include Color Change and Efficacy Results

A solution of body cleaner was prepared by combining 85.5 g Steol 4N (Stepan Company, Northfield, Ill.) with 29.04 g Amphosol HCG (Stepan Company, Northfield, Ill.) and 185.46 g deionized water in a glass bottle equipped with a stir bar. The solution was stirred for one hour at room temperature to give a clear, colorless, foamy solution.

After preparing the above body cleaner, the other ingredients were added and stirred for additional three hours at room temperature. The proportion of these is shown below. Each of these formulations were prepared with had 60 ppm copper concentration. Sodium citrate tribasic hydrate, ≥99% was obtained from Sigma-Aldrich Corp., St. Louis, Mo. CuI/SDS was 75/25 in weight proportion and made as in Example 28. CuI/Silica was 88% CuI and 12% silica made as in Example 64, and CuI/PVP/NaI was in 90/9/1% in weight proportion and made as in Example 57a.

TABLE 42

| Ingredients (g) | Formulation | | |
|---|---|---|---|
| | F1 | F2 | F3 |
| De-ionized water | 61.82 | | |
| Steol 4N | 28.5 | | |
| Amphosol HCG | 9.68 | | |
| Sodium citrate | 0.03 | 0.03 | 0.03 |
| CuI/SLS | 0.0241 | | |
| CuI/Silica | | 0.0205 | |
| CuI/PVP/NaI | | | 0.02 |

Antimicrobial testing results after 24 hours are shown below in the table below. In these tables the original titer for *P. aeruginosa* (ATCC#9027) was 3.43E+07 cfu/mL, and for *S. aureus* (ATCC#25923) 1.11E+07 cfu/mL.

TABLE 43

| Microbe | Solution Without CuI $Log_{10}$ Reduction | F1 $Log_{10}$ Reduction | F2 $Log_{10}$ Reduction | F3 $Log_{10}$ Reduction |
|---|---|---|---|---|
| P. aeruginosa | 1.53 ± 0.09 | 5.31 ± 0.16 | 5.76 ± 0.67 | 5.58 ± 0.07 |
| S. aureus | 1.39 ± 0.05 | 3.32 ± 0.03 | 3.27 ± 0.06 | 3.35 ± 0.30 |

Example 70

Solvent Based Nail Polish (Coating)

A solution of 0.05% Cu in the dried coating was prepared by mixing 0.0014 g CuI functionalized with silica powder (88% CuI and 12% by weight as prepared in Example 64) with 4 g Orly Bonder Rubberized nail polish Basecoat (orange color, available from Orly International Inc, Los Angeles, Calif.)) in a small glass vial equipped with a stir bar. Orly bonder is a solvent based nail polish base and comprises of butyl acetate, isopropyl alcohol, heptane, ethyl acetate, trimethyl pentanyl diisobutyrate, tosylamide/epoxy resin, polyvinyl butyral, nitrocellulose, benzophenone-1, red 17, violet 2, yellow 11 and upon drying at room temperature has a solid content of 20.3%. This solution was stirred at room temperature for 1 hour and was sonicated for 1 hour. It was then left to stir overnight at room temperature. The resulting solution is slightly hazy and orange in color. No precipitate is seen when sitting for several hours at room temperature. The coatings with and without the CuI/silica powder could not be distinguished by eye.

Functionalized CuI particles were made as described in Example 54 (Sample A), excepting that instead of PVP a PVP-olefin copolymer Ganex® V516 was used and the grinding medium was isopropanol. The composition by weight was CuI90%/9% V516 copolymer/1% NaI. This material was also compatible with solvent based Orly Bonder Rubberized nail polish Basecoat.

Example 71

Testing of Antimicrobial Properties Against *Mycobacterium smegmatis, Mycobacterium Fortuitum* and *Candida albicans* (Yeast)

a) Copper iodide powder was prepared as in Example 28 as 75% copper iodide and 25% sodium lauryl sulfate.

b) Copper iodide powder was prepared as in example 57a as 90% copper iodide, 9.75% polyvinylpyrrolidone, 0.25% sodium iodide.

c) Copper iodide powders as described in (a) and (b) were tested against the yeast *Candida albicans* (ATCC #10231), *Mycobacterium smegmatis* (ATCC #14468) and *M. fortuitum* (ATCC #6841) at 60 ppm Cu. $Log_{10}$ reductions in colony forming units are shown in the tables below (">" indicates no viable colony forming units). Both *M. Fortuitum* and *M. Smegmatis* were harvested after 48 hours of growth before subjecting them to the antimicrobial testing.

TABLE 44

| $Log_{10}$ Reductions against *C. albicans* | | | |
|---|---|---|---|
| Time | PBS Control | CuI/SLS | CuI/PVP/NaI |
| 1 min | — | 0.11 ± 0.04 | 0.05 ± 0.03 |
| 5 min | — | 3.21 ± 0.44 | 0.51 ± 0.03 |
| 15 min | 0.02 ± 0.04 | 4.12 ± 0.00 | 2.75 ± 0.05 |
| 1 hour | −0.01 ± 0.11 | >4.12 ± 0.00 | >3.89 ± 0.34 |
| 6 hour | 0.11 ± 0.16 | >4.12 ± 0.00 | 3.74 ± 0.12 |
| 24 hour | 0.14 ± 0.08 | >4.12 ± 0.00 | >4.12 ± 0.00 |
| 48 hour | 0.30 ± 0.13 | >4.12 ± 0.00 | >4.12 ± 0.00 |

Original titer = 6.65E+5 cfu/ml

TABLE 45

| $Log_{10}$ Reductions against *M. fortuitum* | | | |
|---|---|---|---|
| Time | PBS Control | CuI/SLS | CuI/PVP/NaI |
| 15 min | 0.03 ± 0.02 | 0.00 | 0.69 ± 0.03 |
| 1 hour | 0.06 ± 0.11 | 1.81 ± 0.04 | 1.76 ± 0.01 |
| 24 hour | 0.30 ± 0.30 | 4.24 ± 0.13 | 4.05 ± 0.20 |

Original titer = 1.40E+7 cfu/ml

TABLE 46

| $Log_{10}$ Reductions of against *M. smegmatis* | | | |
|---|---|---|---|
| Time | PBS Control | CuI/SLS | CuI/PVP/NaI |
| 15 min | | 1.12 ± 0.05 | 2.28 ± 0.17 |
| 1 hour | 0.7 ± 0.07 | 5.11 ± 0.28 | 4.78 ± 0.60 |
| 24 hour | 1.04 ± 0.22 | >5.42 ± 0.00 | >5.42 ± 0.00 |

Original titer = 1.33E+7 cfu/ml

These results on *M. smegmatis* and *M. fortuitum* suggest that the present functionalized particles would also be effective against *M. tuberculosis* (as *M. Smegmatis* is a surrogate typically used *M. tuberculosis*), and even against the strains of *M. tuberculosis* which are resistant to conventional antibiotics—since the mechanism of antimicrobial activity of the present antimicrobial agents is very different from the antimicrobial mechanisms of conventional antibiotics. Similarly, the results on *C. albicans* show the potential of these materials to control yeast infections.

Example 72

Antimicrobial Efficacy of an Aqueous Acrylic Indoor Paint (Coating)

The CuI/SLS powder (as prepared in Example 28 with a weight proportion of 75:25 of CuI and SLS), an antimicrobial (AM) additive was added to Harmony White Paint (Sherwin Williams (Cleveland, Ohio) Interior Acrylic Latex semi gloss "green sure designation") at a copper concentration of 0.1 wt % and at 0.25% wt. and stirred into the paint. The antimicrobial properties of these coatings were measured after exposing these coatings to growth culture as described earlier for 6 hours to *P. aeruginosa*. The results ($Log_{10}$ reduction) are in the table below.

TABLE 47

| Time | Paint without AM additive | Paint with 0.1% Cu | Paint with 0.25% Cu |
|---|---|---|---|
| 6 hours | 1.05 ± 0.15 | >6.06 ± 0.00 | >6.06 ± 0.00 |

Original Titer = 5.77E+06 cfu/mL

Example 73

Preparation of Polyurethane Foam with Copper Iodide a) Preparation of Copper Iodide Dispersion for Polyurethane Incorporation: Block copolymer functionalized copper iodide was prepared as in Example 45 as 90.9% CuI and 9.1% DisperBYK-190® in the solids. After grinding, 1,4 butanediol was added and water was removed under reduced pressure. The resultant dispersion in 1,4-Butanediol was at 38.96% solids as measured by thermogravimetric analysis.

b) Preparation of Standard Polyurethane Foam: Flex-Foam-iT!® 25 (Smooth-On, Inc. Easton, Pa.) was prepared by thoroughly mixing 1 part A (isocyanate component) and 2 parts B by weight. This was cast in a plastic dish to give an off-white foam.

c) Preparation of Antimicrobial Polyurethane Foam: 10 g of Part B of FlexFoam-iT!® 25 (from Smooth-On, Inc. Easton, Pa.) was mixed thoroughly with 0.66 g CuI/1,4-butanediol dispersion described in (a). This was then thoroughly mixed with 5 g Part A (isocyanate component). This was cast in a plastic dish to give an off-white foam that was similar to the standard foam described in (b).

Example 74

Antimicrobial Epoxy Coating

EPON SU-3 (Miller-Stephenson Chemical Company INC, Danbury, Conn.) and EPALLOY 9000 (CVC Thermoset Specialists Maple Shade, N.J.) were heated separately to 60° C. and while at temperature mixed to form a clear yellow resin. To this mixture was added the anhydride (4-Methyl-hexahydrophthalic anhydride obtained from Broadview Technologies INC. Newark, N.J.) and mixed well to form an opaque resin. To this mixture was added the CuI adduct and mixed well. The antimicrobial CuI functionalized particles (CuI adduct) were prepared by grinding in the following proportion—49.4% CuI, 49.5% Ganex WP-660 (polyvinylpyrrolidone with olefin or alkylated groups obtained from Ashland (New Milford, Conn.)), 1% NaI in isopropanol. After grinding, isopropanol was removed and the resulting powder was added to the resin. The CuI formulated powder dispersed very well in the epoxy medium to give a smooth free flowing resin. The curing agent (AJICURE MY-H an amine adduct obtained from AJINOMOTO CO., INC Japan) was then added and the mixture thoroughly mixed to give a red colored resin. This was degassed under vacuum at 25° C. until no bubbles were seen. The epoxy formulation was then brush coated onto cleaned aluminum substrates and pre-cured under ambient atmosphere at 85° C. for 30 minutes and complete cure at 150° C. for 45 minutes. Copper content in the final coatings was 0.1 weight % (based on 100% solids). The antimicrobial efficacy of the coatings was evaluated using JIS2801-2000 after exposing the microbe to the coating for a period of 24 hours. Coatings without antimicrobial additive were compared, and as shown below, the coatings with the additive were far superior in reducing the microbial population.

TABLE 48

| Log10 reduction of *P. aeruginosa* (ATCC # 9027) | | Log10 reduction of *S. aureus* (ATCC # 25923) | |
|---|---|---|---|
| Without antimicrobial additive | With antimicrobial additive | Without antimicrobial additive | With antimicrobial additive |
| −0.34 ± 0.14 | >3.61 ± 0.56 | 0.31 ± 0.04 | >4.44 ± 0.00 |

Example 75

Activity of CuI Particles Functionalized with PVP Against Polio Virus

The CuI particles functionalized with PVP were prepared in Example 68 (with a small amount of NaI added to help with processability (CuI/PVP/NaI weight ratio was 90/9/1). The average particle size established by Dynamic light scattering (DLS) was 150 nm. The efficacy against this virus was evaluated in an aqueous solution with 60 ppm Cu present as PVP functionalized CuI particles. The results are shown in Table 49. The initial titer concentration for the virus was $5.54 \times 10^6$ PFU/ml.

TABLE 49

| Time, Minutes | $Log_{10}$ reduction |
|---|---|
| 5 | 0.27 |
| 15 | 1.19 |
| 30 | 2.32 |
| 60 | 4.47 |
| 360 | >5.04 |

Example 76

Preparation of Wound Dressings and their Evaluation

Solutions to prepare wound dressings were made in a sure seal bottle equipped with a stir bar. Unless mentioned CuI (when used) was added as PVP functionalized particles containing copper (I) iodide, PVP and NaI in a proportion of 90%/9%/1% by weight. These particles were prepared as in Example 57a. All of the ingredients as shown below were mixed and the solution was stirred and sonicated at room temperature for 30 minutes. The pH of the above solutions was also checked using the Thermo Electron Corporation Orion 290A+pH meter. All copper iodide containing samples were optically translucent or milky (as indicated). Calibration for pH measurement was done using pH standards 4, 7 and 10. The resulting slope was 98.6. Wound dressing samples were then prepared by placing 0.1 ml of the above solution onto a round, ⅜" diameter piece of TX 1109, Technicloth II, hydroentangled, nonwoven polyester (45%)/cellulose (55%) (ITW Texwipe, Mahwah, N.J.). These gauze pieces were then dried in an oven at 60° C. for 30 minutes. For samples containing copper iodide, the nominal copper content was 63.8 mg of Cu/100 $cm^2$ of the wound dressing. The various chemicals used were DL-malic acid (MA); DL-tartaric acid (TA); sodium-L-lactate (NaLA); sodium carboxy methyl cellulose (CMC), molecular weight 700,000; all of which were obtained from Sigma Aldrich Corp, St. Louis, Mo.; ascorbic acid >99% (AA) obtained from Fluka, UK; DL-lactic acid (LA), obtained from Fluka, Japan. Approximate thickness of the gauzes before applying the antimicrobial material was 0.18 mm and after the application and drying it was 0.23 mm. The compostions of various suspensions, their pH to make the wound dressings and their colors are shown in Table 50.

TABLE 50

| Sample | CuI, g | Acid, g | Acid, g | Salt, g | Water, g | CMC, g | Suspension pH | Solution Color | Dressing color |
|---|---|---|---|---|---|---|---|---|---|
| A | 0.1667 | AA, 0.8333 | | | 10 | | 2.3 | TL, Y | Pale Y |
| B | 0.0417 | LA, 0.2083 | | | 2.5 | | 1.8 | Pi/Pu | Pu |
| C | 0.0417 | MA, 0.2083 | | | 2.5 | | 1.6 | Pi/Pu | Dark Br |
| D | 0.0417 | TA, 0.2083 | | | 2.5 | | 1.4 | Pi/Pu | Dark Br |
| E | 0.0417 | | | NaLA, 0.2083 | 2.5 | | 7.5 | Pale Y | Bl/G |
| F | | AA, 0.2083 | | | 2.54 | | — | None | W |
| G | | LA, 0.2083 | | | 2.54 | | — | None | W |
| H | | MA, 0.2083 | | | 2.54 | | — | None | W |
| I | | TA, 0.2083 | | | 2.54 | | — | None | W |
| J | 0.0834 | AA, 0.4166 | | | 5 | | 2.3 | TL, Y | Pale Y |
| K | 0.0834 | LA, 0.2816 | | NaLA, 0.1350 | 5 | | 3.3 | Pi/Pu | Pi/Pu |
| L | 0.0834 | MA, 0.2816 | | NaLA, 0.1350 | 5 | | 3.2 | Pi/Pu | Br |
| M | 0.0834 | TA, 0.2816 | | NaLA, 0.1350 | 5 | | 2.8 | Pale Pi | Br |
| N | 0.0834 | LA, 0.2647 | | NaLA, 0.1269 | 5 | 0.025 | 3.4 | Milky, Pale Y | Pi/Pu |
| O | 0.0834 | LA, 0.2748 | AA, 0.01 | NaLA, 0.1318 | 5 | | 3.3 | Pale Y | Pale Y |
| P | 0.0834 | LA, 0.2748 | | NaLA, 0.1318 + NaAs, 0.01 | 5 | | 3.4 | Pale Y | Pale Y |
| Q | 0.0834 | LA, 0.2748 | TA, 0.01 | NaLA, 0.1318 | 5 | | 3.3 | Pale Y | Pi/Pu |
| R | 0.0834 | LA, 0.3916 | | | 5 | 0.025 | 2 | Milky, Pi/Pu | Pi/Pu |
| S | 0.0834 | AA, 0.3916 | | | 5 | 0.025 | 2.4 | Pale Y | Pale Y |
| T | 0.0834 | MA, 0.2647 | | | 5 | 0.025 | 3.1 | Milky, Pi/Pu | Pi/Pu |
| U | 0.0834 | TA, 0.2647 | | NaLA, 0.1269 | 5 | 0.025 | 2.8 | Milky, Pale Pi | Pi/Pu |
| V | 0.0834 | LA, 0.2623 | AA, 0.01 | NaLA, 0.1193 | 5 | 0.025 | 3.2 | Milky, Pale Y | Pale Y |
| W | 0.0834 | LA, 0.2623 | TA, 0.01 | NaLA, 0.1193 + NaAs, 0.01 | 5 | 0.025 | 3.3 | Milky, Pale Y | Pale Y |
| X | 0.0834 | LA, 0.2623 | | NaLA, 0.1193 | 5 | 0.025 | 3.2 | Milky, Pi/Pu | Pi/Pu |
| Y | 0.0834 | LA, 0.3666 | | | 5 | 0.05 | 2.2 | Milky, Pale Pi | Pi/Pu |

Color Codes: Br = Brown; Bl = Blue, Pu = Purple, Pi = Pink; Y = Yellow; G = Green, W = White
Acid codes- AA = Ascorbic acid, LA = Lactic acid, MA = Malic acid, TA = Tartaric acid,
Salt codes-NaLA = sodium Lactate, NaAs = Sodium ascorbate The dressings were evaluated by looking at the zone of inhibition on an agar plate and also by looking at their staining potential on pig skin.

Zone of inhibition (ZOI) testing was done on the above gauze pieces using both *Staph Aureus* and *Pseudomonas Aeruginosa*. A volume of 300 μl of diluted bacteria solution (cultured overnight, the bacterial concentrations measured as turbidity on McFarland scale were 4 for *S. aureus* and *P. aeruginosa*; and 3 for *A. baumannii* and *E. coli*)) was pipetted onto the surface of a tryptic soy agar (TSA) plate and spread with a sterile glass rod until it was almost completely absorbed into the agar. The gauze samples were placed onto the agar surface and gently pressed with tweezers until complete wetting occurred between the TSA and the gauze. The plates were inverted and incubated at 37° C. overnight (~16 hours). After 16 hours, the plates were examined for a halo (ZOI) around the wound dressing.

A pig skin staining experiment was done on the gauze pieces above. Thin pieces of frozen pig skin were purchased from a local butcher and cut into ~1.5"×1.5" squares after thawing. The epidermis was removed from the center of the pig skin pieces using a sharp razor blade and each pig skin piece was placed in a separate sterile container. The wound dressings were then placed on the pig skin pieces in the spot where the epidermis was removed. One drop of deionized water was placed on the wound dressing to ensure good contact. The sterile containers were then capped and left to sit on the lab bench overnight at room temperature. They were then periodically observed for discoloration. These results are summarized in the table below. The ZOI results for both *Staph aureus* and *Pseudomonas aeruginosa* were similar. Results on ZOI and pig skin staining (along with solution pH to make the dressings) are shown in Table 51. The color codes for skin staining are the same as in Table 50.

TABLE 51

| Sample | CuI | Solution pH | Relative ZOI size | Skin Staining, one day | Skin Staining, 7 days |
|---|---|---|---|---|---|
| A | Yes | 2.3 | 3.5-4 mm | Br/Or around dressing | Dark Br, around and through the skin underneath dressing, not removable |
| B | Yes | 1.8 | 3-3.5 mm | Pale Bl around dressing | Concentric Br circling Pale Bl around dressing, and Pale Bl through the skin underneath dressing, Br removable upon wiping |
| C | Yes | 1.6 | 3-3.5 mm | Pale Bl around dressing | Concentric Br circling Pale Bl around dressing, and Pale Bl through the skin underneath dressing, Br removable upon wiping |
| D | Yes | 1.4 | 3-3.5 mm | Pale Bl around dressing | Concentric light Br circling Pale Bl around dressing, and Pale Bl through the skin underneath dressing, Br removable upon wiping |
| E | Yes | 7.5 | 1-1.5 mm | | |
| F | No | — | None | Light Br around dressing | Dark Br, around and underneath dressing, not removable |
| G | No | — | None | None | Concentric Br circling very Pale Bl around dressing, and very Pale Bl through the skin underneath dressing, Stain removable upon wiping |
| H | No | — | 3.5-4 mm | None | Concentric Br circling very Pale Bl around dressing, and very Pale Bl through the skin underneath dressing, Stain removable upon wiping |
| I | No | — | 3.5-4 mm | None | Concentric Br circling very Pale Bl around dressing, and very Pale Bl through the skin underneath dressing, Stain removable upon wiping |
| J | Yes | 2.3 | 3.5-4 mm | Light Br around/underneath dressing | Dark Br, around and underneath dressing, not removable |
| K | Yes | 3.3 | 3.5-4 mm | Pale Bl stain around dressing, pale Bl/Gr underneath at skin bottom | Br around dressing, and very Pale Bl through the skin underneath dressing, Pale Bl Stain not removable upon wiping |

TABLE 51-continued

| Sample | CuI | Solution pH | Relative ZOI size | Skin Staining, one day | Skin Staining, 7 days |
|---|---|---|---|---|---|
| L | Yes | 3.2 | 3.5-4 mm | Very Pale Bl stain around dressing, very pale Bl/Gr underneath at skin bottom | Concentric Dark Br circling very Pale Bl around dressing, and very Pale Bl through the skin underneath dressing, Pale Bl Stain not removable upon wiping |
| M | Yes | 2.8 | 3.5-4 mm | Very Pale Bl stain around dressing, very pale Bl/Gr underneath at skin bottom | Concentric Dark Br circling very Pale Bl around dressing, and very Pale Bl through the skin underneath dressing, Pale Bl Stain not removable upon wiping |
| N | Yes | 3.4 | — | Pale Bl stain around dressing and underneath at skin bottom | Concentric Dark Br circling Pale Bl around dressing, and Pale Bl/Gray through the skin underneath dressing, Pale Bl Stain not removable upon wiping |
| O | Yes | 3.3 | — | Pale Bl stain around dressing and underneath at skin bottom | Concentric Dark Br circling Pale Bl around dressing, and Pale Bl/Gray through the skin underneath dressing, Pale Bl Stain not removable upon wiping |
| P | Yes | 3.4 | — | Pale Bl stain around dressing and underneath at skin bottom | Concentric Dark Br circling Pale Bl around dressing, and Pale Bl/Gray through the skin underneath dressing, Pale Bl Stain not removable upon wiping |
| Q | Yes | 3.3 | — | Pale Bl stain around dressing and underneath at skin bottom | Pale Bl around dressing, and Pale Y/Bl/Gray through the skin underneath dressing, Pale Bl Stain not removable upon wiping |
| R | Yes | 2 | 3-3.5 mm | Very Pale Bl stain around dressing and underneath at skin bottom | Concentric Dark Br circling Pale Bl/Gray around dressing, and Pale Bl/Gray through the skin underneath dressing, Pale Bl Stain not removable upon wiping |
| S | Yes | 2.4 | — | Light Br around/underneath dressing | Dark Br underneath and through the skin. |
| T | Yes | 3.1 | 3.5-4 mm | Pale Bl around and through the skin underneath dressing | Concentric Pale Gray circling Bl underneath dressing, Bl through skin underneath dressing |
| U | Yes | 2.8 | 3.5-4 mm | None | Pale Bl underneath dressing and bottom of pig skin |
| V | Yes | 3.2 | 3.5-4 mm | Very Pale Bl around and through the skin underneath dressing | Concentric Pale Gray circling Bl underneath dressing, Pale Bl through skin underneath dressing |
| W | Yes | 3.3 | 3.5-4 mm | Very Pale Bl around and through the skin underneath dressing | Concentric Pale Gray circling Bl underneath dressing, Bl through skin underneath dressing |

TABLE 51-continued

| Sample | CuI | Solution pH | Relative ZOI size | Skin Staining, one day | Skin Staining, 7 days |
|---|---|---|---|---|---|
| X | Yes | 3.2 | 3.5-4 mm | Very Pale Bl around and through the skin underneath dressing | Concentric Pale Gray circling Bl underneath dressing, Bl through skin underneath dressing |
| Y | Yes | 2.2 | 3.5-4 mm | None | Pale Bl underneath dressing, Bl/Gr/tan through skin underneath dressing |

These results show that use of ascorbic acid and its salt lead to higher potential for skin staining Use of malic acid, tartaric acid and lactic acid and their salts reduce skin staining with high zone of inhibitions. Although ZOI was seen for samples with pH up to 7.5, but it appears that a larger ZOI was observed in acidic pH range, as acidic pHs also resist bacterial colonization.

Example 77

Efficacy of Wound Dressings Against Bacteria: Results Measured in Growth Medium Solution The following wound dressings were made as described in Example 76. The composition of the solutions to make the wound dressings, their pH and color along with the color of dried dressings is shown in Table 52.

killed. For this reason, an inhibition versus kill experiment was done to determine if the wound dressings were completely killing the bacteria or just inhibiting bacterial growth. First, each dressing was placed in the bottom of a separate sterile container. The dressings were then each inoculated with 10 µl of bacterial solution (cultured overnight) either *S. aureus, P. aeruginosa* or *A. baumannii*. The sterile containers were capped and left at room temperature for one hour. After one hour, 20 ml of tryptic soy broth (growth medium) was added to each container. The containers were capped, shaken and then placed at 37° C. The solutions were monitored for 11 days (264 hours) to see if they remained clear, which indicates a complete bacterial kill, or if they turned cloudy, which indicates that the bacteria were only inhibited and are again growing. As a comparison, commercial wound dressings with silver (Acticoat® from Smith & Nephew, UK and Aquacel® from Convatec, Bridgewater, N.J.) were also tested. The results are summarized in the Table 53.

TABLE 52

| Sample | CuI, g | Acid, g | Acid, g | Salt, g | Water, g | CMC, g | Soln pH | Soln color | Dressing color |
|---|---|---|---|---|---|---|---|---|---|
| A2 control | | | | | | | | | |
| B2 | 0.0835 | 0.2833 AA | | 0.1333 NaAs | 5 | | 3.7 | Milky Y | Pale Y |
| C2 | 0.0835 | 0.2083 LA | | 0.2083 NaLA | 5 | 0.011 | 3.7 | Milky Y | Pi/Pu |
| D2 | 0.0417 | 0.2083 LA | | 0.2083 NaLA | 5 | 0.011 | 3.6 | Pale Y | Pi/Pu |
| E2 | 0.0209 | 0.2083 LA | | 0.2083 NaLA | 5 | 0.011 | 3.7 | Pale Y | Ow |
| F2 | | 0.2083 LA | | 0.2083 NaLA | 5 | 0.011 | 3.7 | Cl | Ow |
| G2 | 0.0835 | 0.1042 LA | 0.1042 MA | 0.2083 NaLA | 5 | 0.011 | 3.6 | Pale Y/Pi | Pi/Pu |
| H2 | 0.0209 | 0.1042 LA | 0.1042 MA | 0.2083 NaLA | 5 | 0.011 | 3.6 | Pale Y | Pale Y/T |
| I2 | | 0.1042 LA | 0.1042 MA | 0.2083 NaLA | 5 | 0.011 | 3.6 | Cl | Ow |
| J2 | 0.0835 | 0.1042 LA | 0.1042 TA | 0.2083 NaLA | 5 | 0.011 | 3.5 | Pale Pi | Pi/Pu |
| K2 | 0.0209 | 0.1042 LA | 0.1042 TA | 0.2083 NaLA | 5 | 0.011 | 3.5 | Pale Y | Pale Y/T |
| L2 | | 0.1042 LA | 0.1042 TA | 0.2083 NaLA | 5 | 0.011 | 3.5 | Cl | Ow |
| M2 | 0.0834 | 0.2730 LA | | 0.1311 NaLA | 5 | 0.0125 | 3.3 | Pale Y | Pi/Pu |

Color Codes: Pu = Purple, Pi = Pink; Y = Yellow; W = White, Ow = Off-white, Cl = Clear/Colorless, T = Tan
Acid codes- AA = Ascorbic acid, LA = Lactic acid, MA = Malic acid, TA = Tartaric acid,
Salt codes-NaLA = sodium Lactate, NaAs = Sodium ascorbate A good result on the zone of inhibition (ZOI) test on a tryptic soy agar plate inoculated with bacteria may not necessarily mean that the bacteria are being completely

TABLE 53

| Sample | CuI | pH of soln | Bacteria | Results 16 hrs | Results 24 hours | Results 88 hours | Results 168 hours | Results 264 hours |
|---|---|---|---|---|---|---|---|---|
| A2 | No | | S. aureus | Cloudy | Cloudy | Cloudy | Cloudy | Cloudy |
| | | | P. aeruginosa | Cloudy | Cloudy | Cloudy | Cloudy | Cloudy |
| | | | A. baumannii | Cloudy | Cloudy | Cloudy | Cloudy | Cloudy |
| B2 | Yes | 3.7 | S. aureus | Clear | Clear | Clear | Clear | Clear |
| | | | P. aeruginosa | Clear | Clear | Clear | Clear | Clear |
| | | | A. baumannii | Clear | Clear | Clear | Clear | Clear |
| C2 | Yes | 3.7 | S. aureus | Clear | Clear | Clear | Clear | Clear |
| | | | P. aeruginosa | Clear | Clear | Clear | Clear | Clear |
| | | | A. baumannii | Clear | Clear | Clear | Clear | Clear |
| D2 | Yes | 3.6 | S. aureus | Clear | Clear | Clear | Clear | Clear |
| | | | P. aeruginosa | Clear | Clear | Clear | Clear | Clear |
| E2 | Yes | 3.7 | S. aureus | Clear | Clear | Clear | Clear | Clear |
| | | | P. aeruginosa | Clear | Clear | Clear | Clear | 50% Cloudy |
| F2 | No | 3.7 | S. aureus | Clear | Cloudy | Cloudy | Cloudy | Cloudy |
| | | | P. aeruginosa | Clear | Clear | Cloudy | Cloudy | Cloudy |
| G2 | Yes | 3.6 | S. aureus | Clear | Clear | Clear | Clear | Clear |
| | | | P. aeruginosa | Clear | Clear | Clear | Clear | Clear |
| H2 | Yes | 3.6 | S. aureus | Clear | Clear | Clear | Clear | Clear |
| | | | P. aeruginosa | Clear | 50% Cloudy | 50% Cloudy | 50% Cloudy | 50% Cloudy |
| I2 | No | 3.6 | S. aureus | Clear | 50% Cloudy | 50% Cloudy | 50% Cloudy | 50% Cloudy |
| | | | P. aeruginosa | Clear | 50% Cloudy | Cloudy | Cloudy | Cloudy |
| J2 | Yes | 3.5 | S. aureus | Clear | Clear | Clear | Clear | Clear |
| | | | P. aeruginosa | Clear | Clear | Clear | Clear | Clear |
| K2 | Yes | 3.5 | S. aureus | Clear | 50% Cloudy | 50% Cloudy | 50% Cloudy | 50% Cloudy |
| | | | P. aeruginosa | 50% Cloudy | 50% Cloudy | 50% Cloudy | 50% Cloudy | 50% Cloudy |
| L2 | No | 3.5 | S. aureus | Clear | Clear | Clear | Clear | Clear |
| | | | P. aeruginosa | Clear | 50% Cloudy | Cloudy | Cloudy | Cloudy |
| M2 | Yes | 3.3 | S. aureus | Clear | Clear | Clear | Clear | Clear |
| | | | P. aeruginosa | Clear | Clear | Clear | Clear | Clear |
| | | | A. baumannii | Clear | Clear | Clear | Clear | Clear |
| Acticoat (silver) | No, | | S. aureus | Cloudy | Cloudy | Cloudy | Cloudy | Cloudy |
| | | | P. aeruginosa | Clear | Cloudy | Cloudy | Cloudy | Cloudy |
| | | | A. baumannii | Clear | Clear | Cloudy | Cloudy | Cloudy |
| Aquacel (silver) | No | | S. aureus | Cloudy | Cloudy | Cloudy | Cloudy | Cloudy |
| | | | P. aeruginosa | Cloudy | Cloudy | Cloudy | Cloudy | Cloudy |
| | | | A. baumannii | Cloudy | Cloudy | Cloudy | Cloudy | Cloudy |

50% Cloudy = 50% of the samples are cloudy and 50% are clear

These results show that CuI is needed in the wound dressings to produce a complete bacterial kill. They also show that for a one hour bacterial inoculation time, the CuI dressings produce a complete kill and the silver dressings do not.

Example 78

Efficacy of Wound Dressing Compositions Including Commercial Products as Evaluated by Measuring ZOI The following wound dressings were prepared following the procedure in Example 76. Please note that the composition of the formulations C3 and D3 is identical, other than the average particle size of CuI in C3 was 120 nm (by DLS), and was made largely by using the parameters given in Example 57a, excepting that a larger media was used. In this case the media used for grinding was 300 μm in diameter. In all of the other samples if CuI was used, then it was made following the procedure in Example 57a with an average CuI particle size of about 10-30 nm. Since by many regulatory agencies particle sizes below 100 nm are considered nanosized, and particles above this size are in a range considered to be microsized. This is indicated in the description of sample C3. The compositions of the solutions to make the wound dressings, their pH and color along with the color of dried dressings is shown in Table 54.

TABLE 54

| Sample | CuI, g | Acid, g | Acid, g | Salt, g | Water, g | CMC, g | Soln pH | Soln Color | Dressing Color |
|---|---|---|---|---|---|---|---|---|---|
| A3 | | | | | | | | | W |
| B3 | 0.1668 | 0.5666 AA | | 0.2666 NaAsc | 10 | | 3.7 | Pale Y | Pale Y/Br |
| C3 | 0.0834 Micro | 0.273 LA | | 0.1311 NaLA | 5 | 0.0125 | 3.3 | Pale Y | Pi/Pu |

TABLE 54-continued

| Sample | CuI, g | Acid, g | Acid, g | Salt, g | Water, g | CMC, g | Soln pH | Soln Color | Dressing Color |
|---|---|---|---|---|---|---|---|---|---|
| D3 | 0.0834 | 0.273 LA | | 0.1311 NaLA | 5 | 0.0125 | 3.3 | Pale Y | Pi/Pu |
| E3 | 0.0834 | 0.2083 LA | | 0.2083 NaLA | 5 | 0.011 | 3.7 | Pale Y | Pi/Pu |
| F3 | 0.0417 | 0.2083 LA | | 0.2083 NaLA | 5 | 0.011 | 3.6 | Pale Y Pi/Pu | Pale |
| G3 | 0.0835 | 0.1042 LA | 0.1042 MA | 0.2083 NaLA | 5 | 0.011 | 3.6 | Pale Y/Pi | Pi/Pu |
| H3 | 0.0835 | 0.1042 LA | 0.1042 TA | 0.2083 NaLA | 5 | 0.011 | 3.5 | Pale Pi | Pi/Pu |
| I3 | 0.1668 | 0.5460 LA | | 0.2622 NaLA | 10 | 0.025 | 3.3 | Pi/Pu | Pi/Pu |

Color Codes: Pu = Purple, Pi = Pink; Y = Yellow; W = White, Br = brown
Acid codes- AA = Ascorbic acid, LA = Lactic acid, MA = Malic acid, TA = Tartaric acid,
Salt codes-NaLA = sodium Lactate, NaAs = Sodium ascorbate Zone of inhibition (ZOI) testing was done on the above gauze pieces using *Staph Aureus, Pseudomonas Aeruginosa* and *Acinetobacter Baumannii*. As a comparison, commercial wound dressings with silver (Acticoat® from Smith & Nephew, UK and Aquacel® from Convatec, Bridgewater, N.J.) were also tested.

ZOI test was conducted following the procedure in Example 76. The ZOI results are seen in the Table 55 below.

TABLE 55

| Sample | CuI or Ag | Soln pH | S. aureus relative ZOI | P. aeruginosa relative ZOI | A. baumannii relative ZOI |
|---|---|---|---|---|---|
| A3 | | | None | None | None |
| B3 | CuI | 3.7 | 2.5 mm | 3 mm | 2 mm |
| C3 | CuI | 3.3 | 2.5 mm | 3 mm | 3 mm |
| D3 | CuI | 3.3 | 2.5 mm | 3 mm | 3 mm |
| E3 | CuI | 3.7 | 2.5 mm | 3 mm | 2.5 mm |
| F3 | CuI | 3.6 | 2-2.5 mm | 3 mm | 2.5 mm |
| G3 | CuI | 3.6 | 2.5 mm | 3 mm | 2.5 mm |
| H3 | CuI | 3.5 | 3 mm | 3 mm | 2.5 mm |
| I3 | CuI | 3.3 | 2.5-3 mm | 3.5-4 mm | 3 mm |
| Acticoat | Ag | | 1.5 mm | 1 mm | 1 mm |
| Aquacel | Ag | | 1.5 mm | 1 mm | 1.5 mm |

Figure 4:
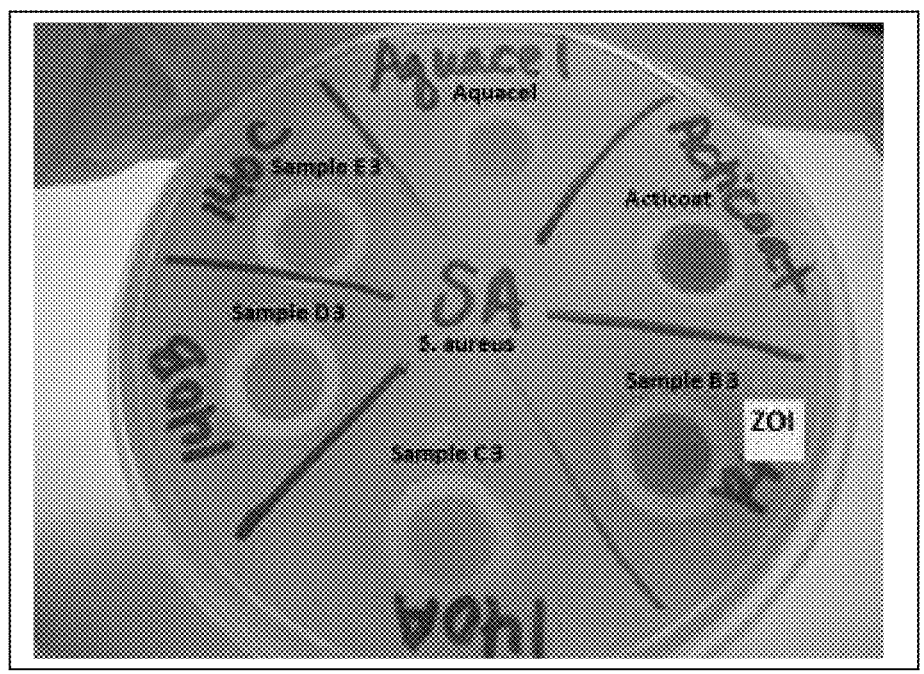
FIG. 4: Zone of inhibition testing results on *S. aureus*; antimicrobial dressings of current invention compared with select commercial dressings.
Figure 5:
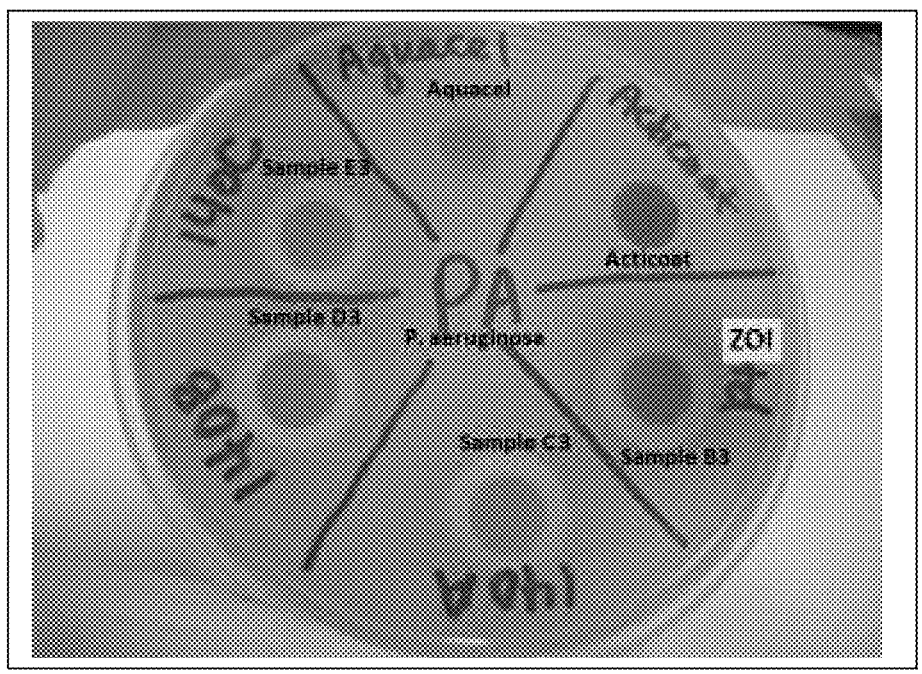
FIG. 5: Zone of inhibition testing results on *P. aeruginosa*; antimicrobial dressings of current invention compared with select commercial dressings.
Figure 6:
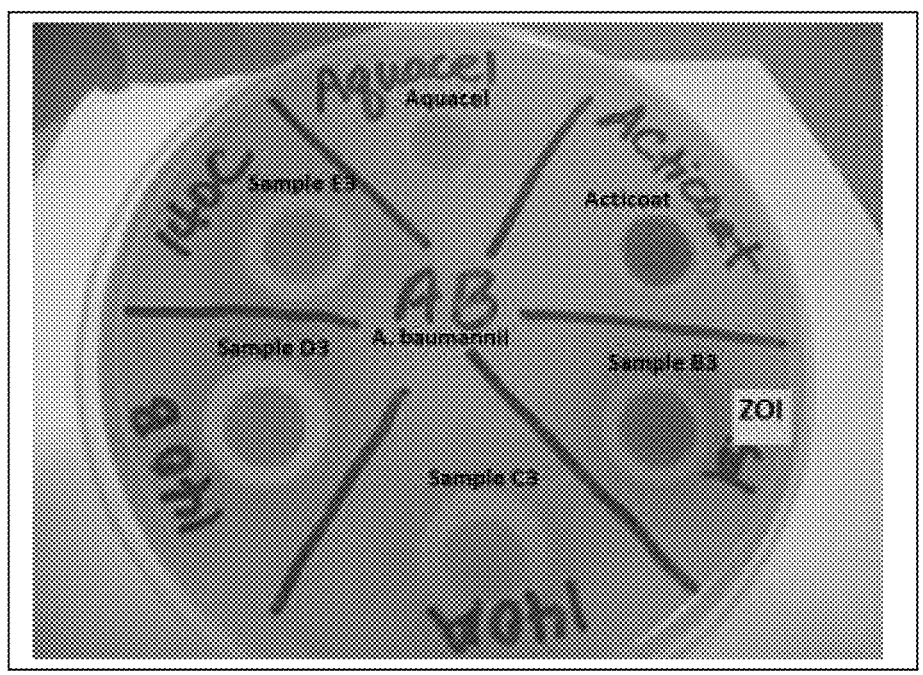
FIG. 6: Zone of inhibition testing results on *A. baumannii*; antimicrobial dressings of current invention compared with select commercial dressings.

The ZOI results indicate that the CuI wound dressings are more effective against *S. aureus, P. aeruginosa* and *A. baumannii* than the commercial silver based wound dressings, Acticoat and Aquacel. In addition, both C3 and D3 (which use different particle sizes), provide similar ZOI results. Photographs of the ZOI plates are shown in FIGS. 4, 5 and 6 for each of the microbes S. *Aureus, P. aeroginosa* and *A. baumannii* respectively.

Example 79

Efficacy of Wound Dressings Against Bacteria in Preformed Biofilms

Wound dressings were made as described in Example 76, using the CuI particles as described also in this example. An aqueous dispersion was made with 1.066 g of PVP/NaI functionalized CuI particles with 4.8 g of ascorbic acid and 0.32 g of sodium hydroxide (used to convert some of the ascorbic acid to its sodium salt, or ascorbate). The copper loading on the dried wound dressing was 63.8 mg/100 $cm^2$ of area. As a comparison, commercial wound dressings with silver (Acticoat® from Smith & Nephew, UK and Aquacel® from Convatec, Bridgewater, N.J.). Biofilms of *P. aeruginosa* or *S. aureus*, were grown on sterilized 25 mm diameter, 0.2 µm membrane filters (polycarbonate membrane filters from Whatman #110606), These filters were placed on tryptic soy agar (TSA). *Psuedomonas aeruginosa* (or *S. aureus*) was grown overnight at 37° C. overnight in tryptic soy broth. The overnight culture was diluted 1:10,000 in phosphate buffered saline (PBS) and 10 µl spots of the diluted culture were placed on the filter disks. Biofilms were allowed to grow on the filter disks for 24 h at 37° C. After 24 h the disks were transferred to fresh TSA plates and biofilms were covered in disks of the wound dressings as described in Example 76 that had been moistened with deionized water. The covered biofilms were allowed to incubate at 37° C. for 18 h. The filter disks and the wound dressings were transferred together to neutralizing broth and sonicated for 1 min followed by vortexing for 1 min. The resulting bacterial suspensions were diluted and plated on growth medium. After incubation at 37° C., the resulting number of surviving colony forming units was calculated.

Ten samples of each type were evaluated including three blank gauzes. The microbial reduction measured as $Log_{10}$ reduction and the standard deviation in this reduction was 7.63±0.00 on the CuI containing gauzes. On Acticoat® this reduction was 3.12±3.18 and on Aquacel® this was 0.64±0.37, again demonstrating the marked superiority of the present antimicrobial materials compared with the commercial silver-based products. No microbial reduction was seen on blanks (−0.42±0.03). In another experiment, dressings were made as in Sample N of Example 76 and evaluated on both *P. aeruginosa* and *S. aureus* biofilms. In both cases the bacterial count after the treatment with the dressings dropped below the experimental detection limits.

Example 80

Processing and Efficacy of Functionalized Cuprous Oxide

Cuprous oxide nanoparticles were prepared on Minicer® mill by grinding 7 grams $Cu_2O$ (obtained from Sigma-Aldrich, St. Louis, Mo., catalogue number 208825, size less than 5 µm), 1 gram sodium lauryl sulfate (SLS), 1 gram, polyacrylamide (MW=10,000), and 1 g ascorbic acid together in 200 ml of water and the final particle size was close to 100 nm. The functionalization agents comprised of all the three organic components, i.e., SLS, polyacrylamide and ascorbic acid. The mill parameters were: 4200 RPM, Pump=600 RPM, Media used=300 µm diameter YTZ, Grinding time=1000 minutes. More information on milling and the mill is provided in Examples 15 and 57. These particles were dried on a rotary evaporator and then stored as a powder. These powders were redispersed in water for testing antimicrobial effectiveness.

Non-functionalized copper oxide particles were prepared by mixing the various ingredients in the same proportions. 0.35 grams of as received $Cu_2O$ powder, 0.05 gram SLS, 0.05 gram, polyacrylamide (MW=10,000), and 0.05 g ascorbic acid were mixed together in 30 ml of water and then subjected to an ultrasonic mixer for 30 minutes at room temperature.

The antimicrobial properties of both dispersions were evaluated as 60 ppm Cu against *Pseudomonas aeruginosa* ATCC #9027. The experiments were conducted in triplicate. The bacteria were exposed to the dispersions for 15 minutes before neutralization. The functionalized particles showed a >4.16±0.00 log reduction and the non-functionalized particles showed a 0.50±0.10 log reduction.

Example 81

Efficacy of Functionalized and Nonfunctionalized Cuprous Oxide

Functionalized cuprous oxide was prepared by forming a slurry of 8 g of cuprous oxide, 1 g of Ganex-V516 (a PVP copolymer) from Ashland (New Milford, Conn.), and 1 g of ascorbic acid (Sigma-Aldrich) in 300 mL of ethanol. This slurry was processed through a Netzsch Minicer bead mill at 4200 RPM for 320 minutes using 0.1 mm media. The resultant dispersion was dried under vacuum and subsequently heated to 70° C. under vacuum to ensure complete solvent removal. Non-functionalized cuprous oxide was prepared by combining 8 g of cuprous oxide with 300 mL ethanol and processing under identical conditions but without the functionalizing agents (i.e., Ganex-V516 and ascorbic acid).

Dispersions containing 2000 ppm Cu were prepared by dispersing the prepared dry cuprous oxide powders in deionized-water. These dispersions were diluted in phosphate buffered saline (PBS) to 60 ppm Cu and distributed in 1 mL aliquots for antimicrobial testing. In this testing, 50 μL of *Pseudomonas aeruginosa* (ATCC #9027) of >5 McFarland (>15×$10^8$ CFU/mL) was added to each 1 mL aliquot of 60 ppm Cu and agitated. After 1 hour of exposure, 100 μL of each sample was neutralized in 900 μL of Dey-Engley neutralizing broth. These neutralized samples were subsequently diluted in PBS to 100× and 1000× total dilution. 100 μL of each diluted sample was dropped on an agar plate and allowed to grow overnight. This procedure was repeated in duplicate for both the functionalized and non-functionalized samples of cuprous oxide.

Figure 14:
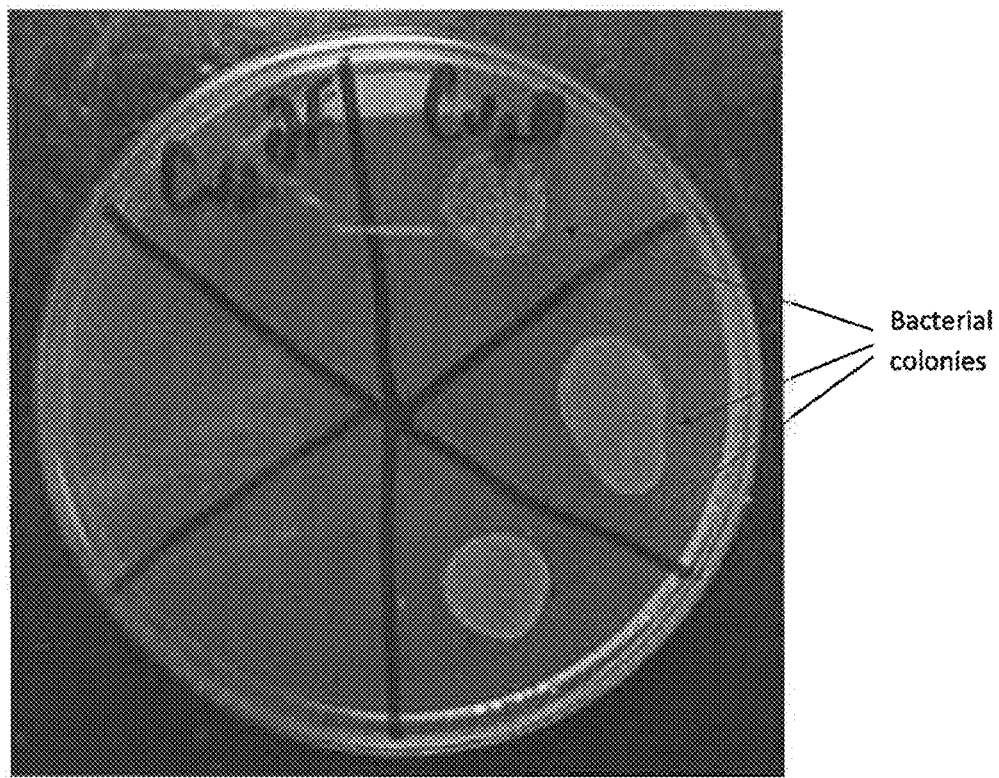
FIG. 14: antibacterial efficacy of functionalized particles of cuprous oxide compared with nonfunctionalized particles of the same.

As shown in the appended figure (FIG. 14), heavy growth of the bacteria (bacterial colonies) was observed for all samples of non-functionalized cuprous oxide and zero growth was observed for the functionalized cuprous oxide. This corresponds to >3 $log_{10}$ kill for functionalized cuprous oxide and <1 $log_{10}$ kill for non-functionalized cuprous oxide. As a control, only the functionalizing agents (without cuprous oxide), Ganex-V516 and ascorbic acid, were tested together at 8.5 ppm each and did not show any antimicrobial activity.

In summary, this invention teaches antimicrobial wound care products such as wound dressings, topical creams and lotions and wound closure products.

These products comprise of antimicrobial materials containing particles of low water solubility copper salts, wherein the solubility of the salts is lower than about 100 mg/liter at room temperature. These particles preferably are in a size of about less than 1000 nm and are surface functionalized. In addition it is preferred that the surface functionalization agents should have a molecular weight of at least 60, preferably 80 and more preferably 100. Some preferred examples of low water solubility copper salts are cuprous halides (e.g., chlorides, bromides and iodides), cuprous thiocyanate and cuprous oxide and the most preferred salt is cuprous iodide. These products further comprise organic acids and/or salts of organic acids. Examples of preferred functionalization agents are one or more of anionic surfactants, polyvinylpyrrolidone, poly vinyl acetate, chitosan, polyethyleneglycol, carboxymethylcellulose, polyacrylamide, and copolymers comprising at least one of an anionic polymer or the above polymers. The acids and their salts described below may also be used as functionalization agents.

Some of the preferred organic acids are hydroxy acids, amino acid, acetic acid, ascorbic acid, erythorbic acid and hyaluronic acid. Of these preferred hydroxyl acids are α or β hydroxyl acid such as lactic acid, malic acid, tartaric acid, glycolic acid, mandelic acid, benzoic acid, hydroxy propionic acid and hydroxy butyric acid and the preferred amino acids are aspartic acid, glutamic acid, arginine and lysine. The preferred salts of these acids are formed using cations of lithium, sodium, potassium, calcium, copper, zinc and silver.

These products may further comprise additional antimicrobial agents, antibiotics, anti-fungal agents, anti-thrombogenic agents, anesthetics, anti-inflammatory agents, analgesics, anticancer agents, vasodilation substances, wound healing agents, angiogenic control agents, antipruritic agents, immune boosting agents and nutrients.

In a preferred embodiment the antimicrobial wound care product having copper releasing composition comprises (a) particles of CuI; (b) an acid selected from at least one of hydroxy acid, amino acid, acetic acid, ascorbic acid, erythorbic acid, hyaluronic acid; and (c) a material selected from at least one of a salt or an ester of an organic acid; wherein the pH of the composition is in the range of about 3 and 6. The pH may be measured of the liquid phase, if all of these components are added in a liquid phase to form the product. Alternatively, one can extract the materials from a finished solid product (antimicrobial bandage or bandage layer) into an aqueous media and then its pH is measured. According to this embodiment any one of these methods may be used to determine the pH, thus in either one or both of these cases the pH may be between 3 and 6.

This invention also teaches antimicrobial wound care products which derive their antimicrobial properties by release of ions including copper, where these products comprise compositions containing porous particles containing nanopores with low solubility copper salts deposited in these pores. Some of the preferred salts are cuprous halides—particularly cuprous iodide, copper thiocyanate and copper oxide. These compositions or products further comprise organic acids and/or their salts. The above incorporation or deposition of such salts in the porous particles is NOT carried out by exchanging ions (ion-exchange) from the matrix of the porous particles, but rather by depositing the salts within the nanopores of the particles. Cuprous iodide is a particularly preferred copper salt. Some of the preferred acids and salts are listed in the previous embodiments. Preferably such compositions or products have a pH in the range of 3 and 6. If these are solid products or coatings then one can measure the pH by extracting the extractable materials in an aqueous media and measuring its pH. Alternatively, the pH is measured of the liquid with particles which is used to form the product or a coating on the product. According to this embodiment in any one of these cases the pH is between 3 and 6.

This invention also teaches wound care products containing compositions of copper ion releasing low water solubility copper salt particles. The surfaces of these particles are modified by functionalization agents. A preferred low solubility copper salt is copper iodide. The pH of the compositions or the products is preferably in the range of about 1.5 and 8. For solid wound care products one can measure the pH as described in the previous embodiment. These compositions may also have organic acids and/or their salts. These products may also have one or more other additives to help with wound healing, where these other additives are selected from other antimicrobial materials, antibiotics, anti-fungal agents, anti-thrombogenic agents, anesthetics, anti-inflammatory agents, analgesics, anticancer agents, vasodilation substances, wound healing agents, angiogenic control agents, antipruritic agents, immune boosting agents and nutrients.

The antimicrobial wound care products including topical products of this invention comprise compositions of low water solubility copper salts which have the ability to release copper ions. The size of such particles is preferably below 1,000 nm, and the concentration of the copper salt in these compositions is at or below 5 weight %. For example if a liquid (or a lotion), cream, ointment product is used then according to this embodiment the concentration of the copper salt in the product is at or below 5 wt %. If copper salt is incorporated by infusing within a solid or only as a coating, then 5 wt % in this embodiment refers to the concentration within the solid or the coating respectively. These products may also have other additives as disclosed in the previous embodiments.

When antimicrobial bandage products are made following this innovation, the preferred copper releasing materials are CuI and $Cu_2O$ in a size of about 1,000 nm or smaller. The concentration of copper (incorporated as copper salt) in these bandages is typically less than about 200 $mg/cm^2$ of the bandage area. Since bandages may comprise of several layers and only one or more of these layers of the bandage may have antimicrobial additives, this concentration will refer to any layer in the bandage which contains the antimicrobial additives of this invention. The area normally refers to the area of contact of the bandage to the skin/wound of the patient or the area projected on to the body part (skin/wound) of the patient. The pH of the liquid compositions used to impart the antimicrobial characteristics (e.g., by coating a substrate material) or infusing the antimicrobial material into a solid (e.g., a foam layer) is preferably in the range of about 3 and 6. Alternatively, one may also extract materials into an aqueous media from an antimicrobial bandage (or bandage layer) and then its pH measured. According to this embodiment any one of these measures may be used to determine the pH, and in at least of these cases the pH may be between 3 and 6. The bandage may optionally comprise of other additives mentioned in previous embodiments.

Some examples of wound care products are listed in Table 2, such as dressings, wound closure products, creams and lotions, cleaning compositions and coated products.

The functionalized particles of this invention can be made very economically by forming the particles in the presence of functionalizing agents prior to their incorporation into the products. These methods include synthesis, precipitation from solutions and by grinding larger particles.

It will be understood that various modifications may be made to the embodiments disclosed herein. Hence the above description should not be construed as limiting, but merely as exemplifications of preferred embodiments. Those skilled in the art will envision other modifications that come within the scope and spirit of the claims appended hereto. All patent applications cited as priority (related applications) are explicitly incorporated herein by reference in their entirety.

The invention claimed is:

1. An antimicrobial wound care bandage product having a copper releasing composition comprising:
   (a) copper releasing particles of a copper halide with water solubility at room temperature of less than about 100 mg/liter,
   wherein the surfaces of said particles are modified by at least one functionalizing agent; and
   (b) at least one material selected from an organic acid or a salt of an organic acid, and wherein the pH of the copper releasing composition is in the range between about 3 and about 6.

2. The antimicrobial wound care product as in claim 1, wherein the said copper halide is cuprous iodide.

3. The antimicrobial wound care product as in claim 1, wherein the average size of the said particles is below 1,000 nm.

4. The antimicrobial wound care product as in claim 1, wherein the molecular weight of the said functionalization agent is at least 60.

5. The antimicrobial wound care product as in claim 1, wherein the salt of the organic acid comprises a cation selected from the group consisting of lithium, sodium, potassium, calcium, copper, zinc and silver.

6. The antimicrobial wound care product as in claim 1, wherein the composition further contains at least one of an additional antimicrobial agent, antibiotic, anti-fungal agent, anti-thrombogenic agent, anesthetic, anti-inflammatory agent, analgesic, anticancer agent, vasodilation substance, wound healing agent, angiogenic control agent, antipruritic agent, immune boosting agent and a nutrient.

7. An antimicrobial wound care bandage product having a copper releasing composition comprising:
   (a) copper releasing particles containing CuI;
   (b) an acid selected from at least one of hydroxy acid, amino acid, acetic acid, erythorbic acid, and hyaluronic acid;
   (c) a material selected from at least one of a salt or an ester of an organic acid; and
   (d) the pH of the composition in the range between about 3 and about 6.

8. An antimicrobial wound care bandage product having a copper releasing composition comprising:
   copper-releasing particles containing copper halide with a water solubility at room temperature of less than about 100 mg/liter,
   wherein the surfaces of the copper-releasing particles are modified by at least one functionalizing agent, and
   wherein the pH of the said composition is between about 3 and about 6.

9. The antimicrobial wound care product as in claim 8, wherein said halide is cuprous iodide.

10. The antimicrobial wound care product as in claim 7, wherein the concentration of CuI in said product is at or below 5 weight %.

11. The antimicrobial wound care product as in claim 8, wherein the concentration of copper halide in said product is at or below 5 weight %.

* * * * *